US012605432B2

(12) United States Patent (10) Patent No.: US 12,605,432 B2
Essen-Möller et al. (45) Date of Patent: Apr. 21, 2026

(54) COMBINATIONS FOR ANTIGEN BASED THERAPY

(71) Applicant: Diamyd Medical AB, Stockholm (SE)

(72) Inventors: Anders Essen-Möller, Stockholm (SE); Johnny Ludvigsson, Linköping (SE)

(73) Assignee: DIAMYD MEDICAL AB, Stockholm (SE)

( * ) Notice: Subject to any disclaimer, the term of this patent is extended or adjusted under 35 U.S.C. 154(b) by 0 days.

(21) Appl. No.: 16/566,610

(22) Filed: Sep. 10, 2019

(65) Prior Publication Data

US 2020/0138920 A1 May 7, 2020

Related U.S. Application Data

(63) Continuation-in-part of application No. 15/315,557, filed as application No. PCT/SE2015/050651 on Jun. 4, 2015.

(30) Foreign Application Priority Data

Jun. 4, 2014 (SE) .................................... 1450678-6
Nov. 4, 2014 (SE) .................................... 1451315-4

(51) Int. Cl.
A61K 35/12 (2015.01)
A61K 31/59 (2006.01)
A61K 38/51 (2006.01)
A61K 39/00 (2006.01)
A61K 39/395 (2006.01)
A61P 3/10 (2006.01)
C12N 9/88 (2006.01)

(52) U.S. Cl.
CPC .............. *A61K 38/51* (2013.01); *A61K 31/59* (2013.01); *A61K 39/0008* (2013.01); *A61K 39/001* (2013.01); *A61K 39/3955* (2013.01); *A61P 3/10* (2018.01); *C12N 9/88* (2013.01); *C12Y 401/01015* (2013.01); *A61K 2035/122* (2013.01)

(58) Field of Classification Search
None
See application file for complete search history.

(56) References Cited

U.S. PATENT DOCUMENTS

| | | | |
|---|---|---|---|
| 5,853,723 A | 12/1998 | Jacobs et al. | |
| 2002/0107210 A1 | 8/2002 | Herrath | |
| 2002/0131963 A1 | 9/2002 | Baekkeskov et al. | |
| 2005/0152914 A1 | 7/2005 | Harris et al. | |
| 2006/0199228 A1 | 9/2006 | Peakman | |
| 2007/0190045 A1 | 8/2007 | Herold et al. | |
| 2007/0255237 A1* | 11/2007 | Lobl .................. | A61M 39/105 |
| | | | 604/288.01 |

FOREIGN PATENT DOCUMENTS

| | | |
|---|---|---|
| CN | 101678090 A | 3/2010 |
| WO | WO 1995/07992 | 3/1995 |
| WO | WO 1997/12034 | 4/1997 |
| WO | WO 98/47529 A1 | 10/1998 |
| WO | WO 03/045316 A2 | 6/2003 |
| WO | WO 2005/102374 | 11/2005 |
| WO | WO 2007/044394 A2 | 4/2007 |
| WO | WO 2008/083331 A2 | 7/2008 |
| WO | WO 2008/129426 | 10/2008 |
| WO | WO 2009/051837 | 4/2009 |
| WO | WO 2009/078796 A1 | 6/2009 |
| WO | WO 2012/050907 A2 | 4/2012 |
| WO | WO 2012/062697 A1 | 5/2012 |
| WO | WO 2012/146364 A1 | 11/2012 |
| WO | WO 2013/113501 A1 | 8/2013 |
| WO | WO 2014/004866 A1 | 1/2014 |

OTHER PUBLICATIONS

Casas, R., et al. Front. Immunol 2020;11:1-11.*
Trepel, M., et al. Cancer Res. 61;8119-8112 (Year: 2001).*
Puente-Martin, S., et al. Front. Immunol.;14:1112570 (Year: 2023).*
Martinez-Gomez et al ( Archive of Allergy and Immunol., 2009, v. 150,p. 59-62.*
Guan et al., "Vaccination with IA-2 autoantigen can prevent late prediabetic nonobese diabetic mice from developing diabetes mellitus", Diaetes Research and Clinical Practice, 2011, 95(1): 93-97.
Norman et al., "Faster pharmacokinetics and increased patient acceptance of intradermal insulin delivery using a single hollow microneedle in children and adolescents with type 1 diabetes", Pediatric Diabetes, 2013, 14: 459-465.
Woodfolk, "Molecular mechanisms in allergy and clinical immunology, T-cell responses to allergens", J. Allergy Clin. Immunol., 2007, 119(2): 280-294.
Serreze et al., "Loss of Intra-Islet CD20 Expression May Complicate Efficacy of B-Cell-Directed Type 1 Diabetes Therapies", Diabetes, 2011, 60: 2914-2921.
Kundig et al., "Intralymphatic immunotherapy: Time interval between injections is essential", J. Allergy Clin. Immunol., 2014, 133(3): 930-931.
Senti et al., "Intralymphatic allergen administration renders specific immunotherapy faster and safer: A randomized controlled trial", Proc. Nat'l. Acad. Sci., 2008, 105(46): 17908-17912.
Haller et al., "More on Intralymphatic Injection of Autoantigen in Type 1 Diabetes", N. Engl. J. Med., 377(4), pp. 403-405 (Jul. 27, 2017).
Johansen et al., Direct intralymphatic injection of peptide vaccines enhances immunogenicity,: Eur. J. Immunol., 35, pp. 568-574 (2005).

(Continued)

*Primary Examiner* — Michail A Belyavskyi
(74) *Attorney, Agent, or Firm* — James S. Keddie; Bozicevic, Field & Francis LLP

(57) ABSTRACT

Provided herein, among other things, is a method for prevention and/or treatment of an autoimmune disease. In some embodiments, the method may comprise administering to a subject a composition, said composition comprising at least one β cell autoantigen, by intralymphatic injection or injection directly into a lymph node.

17 Claims, No Drawings

(56) References Cited

OTHER PUBLICATIONS

Ludvigsson et al., "GAD Treatment and Insulin Secretion in Recent-Onset Type 1 Diabetes," N. Engl. J. Med., 359 (18), pp. 1909-1920 (2008).

Ludvigsson et al., "Intralymphatic Injection of Autoantigen in Type 1 Diabetes," N. Engl. J. Med., 376(7), pp. 697-699 (Feb. 16, 2017).

Correction of Ludvigsson et al., "Intralymphatic Injection of Autoantigen in Type 1 Diabetes," N. Engl. J. Med., 376 (7), pp. 697-699 (Feb. 16, 2017); Published in N. Engl. J. Med., 377(4), p. 405 (Jul. 27, 2017).

Tavira et al., "Intralymphatic Glutamic Acid Decarboxylase-Alum Administration Induced Th2-Like-Specific Immunomodulation in Responder Patients: A Pilot Clinical Trial in Type 1 Diabetes," Journal of Diabetes Research, vol. 2018, Article ID 9391845, 11 pages (2018).

Wherrett et al., "Antigen-Based Therapy with Glutamic Acid Decarboxylase (GAD) Vaccine in Patients with Recent-Onset Type 1 Diabetes: A Randomised Double-Masked Controlled Trial," Author manuscript, published in final edited form as Lancet, 378(9788), pp. 319-327 (2011) (18 pages).

Trani, et al., "CD25+ Immunoregulatory CD4 T Cells Mediate Acquired Central Transplantation Tolerance", J. Immunol., 2003, 170: 279-286.

EU Clinical Trials, "Open label trial to evaluate the tolerability of a combination therapy consisting of GAD-alum (Diamyd, etanercept and vitamin D in children and adolescents newly diagnosed with type 1 diabetes," EcdraCT No. 2014-001323-76, EDCR (Etanercept Diamyd Comination Regimen), retrieved online from: <https://www.clinicaltrialsregister.eu/ctr-search/trial/2014-001323-76/SE>, date first entered into EudraCT database Jun. 5, 2014 (10 pages).

EU Clinical Trials, "Pilot trial to preserve residual insulin secretion in children and adolescents with recent onset Type 1 diabetes by using GAD-antigen (Diamyd) therapy in combination with vitamin D and ibuprogen," EudraCT No. 2012-003251-11, DIABGAD-1, retrieved online from: <https://www.clinicaltrialsregister.eu/ctr-search/trial/2012-003251-11/SE>, first entered in the EudraCT database Jul. 25, 2012 (9 pages).

Ludvigsson, "Novel therapies in the management of type 1 diabetes mellitus," Panminerva Med., vol. 54, No. 4, pp. 257-270 (2012).

Press Release, "New clinical study with Diamyd diabetes vaccine," retrieved from: <http://www.diamyd.com/docs/pressClip.aspx?section=investor&ClipID=738265>, 5 pages (Jan. 30, 2013).

Bach and Chatenoud, "Tolerance to Islet Autoantigens in Type 1 Diabetes," Annu. Rev. Immunol., 19, pp. 131-161 (Apr. 2001).

Gerling et al., "The Thymus as a Site for Evaluating the Potency of Candidate β Cell Autoantigens in NOD Mice," Journal of Autoimmunity, 7(6), pp. 851-858 (Dec. 1994).

Lin et al., "Reversal of type 1 diabetes by a new MHC II-peptide chimera: "Single-epitope-mediated suppression" to stabilize a polyclonal autoimmune T-cell process," European Journal of Immunology, 40(8), pp. 2277-2288 (Jun. 2010).

Ludvigsson, "The latest pharmacotherapy options for type 1 diabetes," Expert Opinion On Pharmacotherapy, 15(1), pp. 37-49 (Nov. 2013).

Robert et al., "Oral Delivery of Glutamic Acid Decarboxylase (GAD)-65 and IL 10 by Lactococcus lactis Reverses Diabetes in Recent-Onset NOD Mice," Diabetes, 63(8), pp. 2876-2887 (Mar. 2014).

Tian et al., "Combining Antigen-Based Therapy with GABA Treatment Synergistically Prolongs Survival of Transplanted β-Cells in Diabetic NOD Mice," PLOS One, 6(9), (Sep. 2011) (5 pages).

Tisch et al., "Immune Response to Glutamic Acid Decarboxylase Correlates With Insulitis in Non-Obese Diabetic Mice," Nature, 366, pp. 72-75 (Nov. 1993).

Farias et al., "Vitamin D3 Induces IDO+ Tolerogenic DCs and Enhances Treg, Reducing the Severity of EAE", CNS Neuroscience & Therapeutics, 2013, 19: 269-277.

Adorini, "Tolerogenic dendritic cells induced by vitamin D receptor ligands enhance regulatory T cells inhibiting autoimmune diabetes" Ann N Y Acad Sci. 2003, 987: 258-61.

Agardh et al, "Clinical evidence for the safety of GAD65 immunomodulation in adult-onset autoimmune diabetes", Journal of Diabetes and Its Complications, 2005; 19: 238-246.

Agostino et al, "Effect of the tyrosine kinase inhibitors (sunitinib, sorafenib, dasatinib, and imatinib) on blood glucose levels in diabetic and nondiabetic patients in general clinical practice" J Oncol Pharm Pract. 2011 17: 197-202.

Axelsson et al, "Early induction of GAD(65)-reactive Th2 response in type 1 diabetic children treated with alum-formulated GAD(65)." Diabetes Metab Res Rev. 2010 26: 559-68.

Baekkeskov et al, "Autoantibodies in newly diagnosed diabetic children immunoprecipitate human pancreatic islet cell proteins" Nature 1982 298:167-169.

Baekkeskov et al, "Identification of the 64K autoantigen in insulin-dependent diabetes as the GABA-synthesizing enzyme glutamic acid decarboxylase" Nature 1990 347: 151-156.

Calcinaro et al, "Oral probiotic administration induces interleukin-10 production and prevents spontaneous autoimmune diabetes in the non-obese diabetic mouse." Diabetologia 2005 48:1565-75.

Chen et al, "Evidence that a peptide spanning the B—C junction of proinsulin is an early Autoantigen epitope in the pathogenesis of type 1 diabetes" J. Immunol. 2001 167: 4926-4935.

Cheramy et al, "GAD-alum treatment in patients with type 1 diabetes and the subsequent effect on GADA IgG subclass distribution, GAD65 enzyme activity and humoral response." Clin Immunol. 2010 137: 31-40.

Coutant et al, "Low dose linomide in Type I juvenile diabetes of recent onset: a randomised placebo-controlled double blind trial" Diabetologia 1998 41: 1040-1046.

Daniel et al, "Protection of nonobese diabetic mice from diabetes by intranasal or subcutaneous administration of insulin peptide B-(9-23)." Proc. Natl. Acad. Sci. USA 1996 93: 956-960.

DCC Trial Research Group "Effect of intensive therapy on residual beta-cell function in patients with type 1 diabetes in the diabetes control and complications trial. A randomized, controlled trial" Ann Intern Med 1998 128: 517-523.

Denes et al, "Autoantigens plus interleukin-10 suppress diabetes autoimmunity." Diabetes Technol Ther. 2010 12: 649-61.

DPT-Type 1 Diabetes Study Group, "Effects of Insulin in Relatives of Patients With Type 1 Diabetes Mellitus", N Engl J Med. 2002 346: 1685-1691.

Dupre et al, "Clinical trials of cyclosporin in IDDM" Diabetes Care 1988 1: 37-44.

Eisenbarth et al, "Anti-thymocyte globulin and prednisone immunotherapy of recent onset type 1 diabetes mellitus" Diabetes Res 1985 2:271-276.

Elias et al, "The hsp60 peptide p277 arrests the autoimmune diabetes induced by the toxin streptozotocin" Diabetes 1996 45: 1168-1172.

Elliot et al, "Prevention or delay of type 1 (insulin-dependent) diabetes mellitus in children using nicotinamide" Diabetologia 1991 34:362-365.

Faresjo et al, "The immunological effect of photopheresis in children with newly diagnosed type 1 diabetes" J. Pediatr Res 2005 58: 459-466.

Gribben et al, "CTLA4 mediates antigen-specific apoptosis of human T cells" Proc Natl Acad Sci 1995 92: 811-815.

Heine et al, "1,25-dihydroxyvitamin D(3) promotes IL-10 production in human B cells" Eur J Immunol. 2008 38: 2210-8.

Heinze, "Immunoglobulins in children with autoimmune diabetes mellitus" Clin Exp Rheumatol 1996 15:S99-102.

Homann et al, "Insulin in oral immune "tolerance": a one-amino acid change in the B chain makes the difference." J. Immunol. 1999 163: 1833-8.

Johansen et al, "Direct intralymphatic injection of peptide vaccines enhances immunogenicity" Eur J Immunolo. 2005 35: 568-574.

Johansen et al, "New routes for allergen immunotherapy" Human Vaccines & Immunotherapeutics 2012 8: 1525-1533.

Jun et al, "Prevention of autoimmune diabetes by immunogene therapy using recombinant vaccinia virus expressing glutamic acid decarboxylase." Diabetologia 2002 45: 668-676.

(56)        References Cited

OTHER PUBLICATIONS

Kaufman et al, "Spontaneous loss of T-cell tolerance to glutamic acid decarboxylase in murine insulin-dependent diabetes" Nature 1993 366:69-72.

Keller et al, "Insulin prophylaxis in individuals at high risk of type 1 diabetes" Lancet 1993 10: 927-928.

Keymeulen et al, "Insulin needs after CD3-antibody therapy in new-onset type 1 diabetes" N Engl J Med 2005 352: 2598-2608.

Kim et al, "Cyclooxygenase Inhibitors, Aspirin and Ibuprofen, Inhibit MHC-restricted Antigen Presentation in Dendritic Cells." Immune Netw. 2010 10: 92-8.

Lieb, "Antidepressants, prostaglandins and the prevention and treatment of cancer" Med Hypotheses 2007 69:684-9.

Louvet et al, "Tyrosine kinase inhibitors reverse type 1 diabetes in nonobese diabetic mice." Proc Natl Acad Sci U.S.A. 2008 105: 18895-900.

Ludvigsson et al, "Beta-cell function in children with diabetes" Diabetes 1978 1:230-234.

Ludvigsson et al, "C-peptide in juvenile diabetics beyond the postinitial remission period. Relation to clinical manifestations at onset of diabetes, remission and diabetic control" Acta Paediatrica Scand 1977 66: 177-184.

Ludvigsson et al, "Extended evaluation of the safety and efficacy of GAD treatment of children and adolescents with recent-onset type 1 diabetes: a randomised controlled trial" Diabetologia 2011 54: 634-40.

Ludvigsson et al, "GAD treatment and insulin secretion in recent-onset type 1 diabetes" N Engl J Med. 2008 359: 1909-1920.

Ludvigsson et al, "GAD65 antigen therapy in recently diagnosed type 1 diabetes mellitus." New Engl J Med 2012 366: 433-42.

Ludvigsson et al, "Photopheresis at onset of type 1 diabetes: a randomised, double blind, placebo controlled trial" Arch Dis Child 2001 85: 149-154.

Ludvigsson et al, "Plasmapheresis in the initial treatment of insulin-dependent diabetes mellitus in children." Br Med J 1983 286: 176-178.

Ludvigsson et al, "Treatment with antioxidants at onset of type 1 diabetes in children: a randomized, double-blind placebo-controlled study" Diabetes Metab Res Rev 2001 17:131-136.

Ludvigsson, "Adequate doses of autoantigen administered using the appropriate route may create tolerance and stop autoimmunity" Diabetologia 2009 52: 175-176.

Madsbad et al, "Role of residual insulin secretion in protecting against ketoacidosis in insulin-dependent diabetes." Br Med J 1979; 2: 1257-1259.

Maloy et al, "Intralymphatic immunization enhances DNA vaccination" PNAS 2001 98: 3299-3303.

Mastrandrea et al, "Etanercept treatment in children with new-onset type 1 diabetes: pilot randomized, placebo-controlled, double-blind study" Diabetes Care 2009 32: 1244-1249.

Mocellin et al, "The multifaceted relationship between IL-10 and adaptive immunity: putting together the pieces of a buzzle" Cytokine Growth Factor Rev. 2004 15: 61-76.

Schloot et al, "Effect of heat shock protein peptide DiaPep277 on ß-cell function in paediatric and adult patients with recent-onset diabetes mellitus type 1: two prospective, randomized, double-blind phase II trials", Diabetes Metab Res Rev. 2007; 23: 276-285.

Niiro et al, "MAP kinase pathways as a route for regulatory mechanisms of IL-10 and IL-4 which inhibit COX-2 expression in human monocytes" Biochem Biophys Res Commun. 1998 250: 200-5.

Obermajer et al, "Positive feedback between PGE2 and COX2 redirects the differentiation of human dendritic cells toward stable myeloid-derived suppressor cells." Blood. 2011 118: 5498-505.

Orban et al, "Costimulation modulation with abatacept in patients with recent-onset type 1 diabetes: follow-up 1 year after cessation of treatment." Diabetes Care 2014 37: 1069-75.

Orban et al, "Co-stimulation modulation with abatacept in patients with recent-onset type 1 diabetes: a randomised, double-blind, placebo-controlled trial." Lancet 2011 378: 412-419.

Ortqvist et al, "Temporary preservation of beta-cell function by diazoxide treatment in childhood type 1 diabetes" Diab Care 2004 27: 2191-2197.

Palmer et al, "Insulin antibodies in insulin-dependent diabetics before insulin treatment" Science 1983 222: 1337-1339.

Patakas et al, Abstract #723 ACR/ARHP Annual Meeting, 2013, "Abatacept is Highly Effective at Inhibiting T cell Priming and Induces a Unique Transcriptional Profile in CD4+ T Cells".

Petersen et al, Neonatal tolerization with glutamic acid decarboxylase but not with bovine serum albumin delays the onset of diabetes in NOD mice Diabetes 1994 44:1478-1484.

Pleau et al, "Prevention of autoimmune diabetes in nonobese diabetic female mice by treatment with recombinant glutamic acid decarboxylase (GAD 65)" Clinical Immunology and Immunopathology, 1995 76: 90-95.

Plesner et al, "Immunization of diabetes-prone or non-diabetes-prone mice with GAD65 does not induce diabetes or slet cell pathology" J Autoimmunity 1998 11:335-341.

Posadas et al, "Abatacept in the treatment of rheumatoid arthritis" Expert Rev Clin Immunol. 2009 5: 9-17.

Pozzilli et al, "Glucose evaluation trial for remission (GETREM) in type 1 diabetes: a European multicentre study" Diabetes Res Clin Pract 2005 68: 258-264.

Rabin et al, "Islet cell antigen 512 is a diabetes-specific islet autoantigen related to protein tyrosine phosphatases" J. Immunol. 1994 152: 3183-3188.

Raz et al, "Beta-cell function in new-onset type 1 diabetes and immunomodulation with a heat-shock protein peptide (DiaPep277): a randomised, double-blind, phase II trial" Lancet 2001 358: 1749-1753.

Rigby et al, "Targeted immune interventions for type 1 diabetes: not as easy as it looks!" Current Opinion Endocrinol Diabetes Obes 2014, 21:271-278.

Robert et al, "Oral delivery of glutamic acid decarboxylase (GAD)-65 and IL 10 by Lactococcus lactis reverses diabetes in recent-onset NOD mice" Diabetes 2014 63: 2876-87.

Rudy et al, "Similar peptides from two beta cell autoantigens, proinsulin and glutamic acid decarboxylase, stimulate T cells of individuals at risk for insulin-dependent diabetes" Mol. Med., 1995 1: 625-633.

Russel et al, "The impact of anti-inflammatory cytokines on the pancreatic β-cell" Islets 2014 6: e950547.

Senti et al, "Intralymphatic allergen administration renders specificimmunotherapy faster and safer: a randomized controlled trial" PNAS 2008 105: 17908-17912.

Shah et al, "A randomized trial of intensive insulin therapy in newly diagnosed insulin-dependent diabetes mellitus" N Engl J Med 1989 320:550-554.

Sherry et al, "Teplizumab for treatment of type 1 diabetes (Protege study): 1-year results from a randomised, placebo-controlled trial" Lancet. 2011 378: 487-97.

Silverstein et al, "Immunosuppression with azathioprine and prednisone in recent-onset insulin-dependent diabetes mellitus" N Engl J Med 1988 319: 599-604.

Skoglund et al, "GAD autoantibody epitope pattern after GAD-alum treatment in children and adolescents with type 1 diabetes." Pediatr Diabetes. 2012 13: 244-250.

Diabetes Prevention Trial—Type I Study Group, "Effects of oral insulin in relatives of patients with type 1 diabetes: The Diabetes Prevention Trial—Type 1." Diabetes Care 2005 28: 1068-1076.

Skyler et al, "Stopping type 1 diabetes: attempts to prevent or cure type 1 diabetes in man." Diabetes 2011 60: 1-8.

Skyler, "Immune Intervention for Type 1 Diabetes, 2012-2013", Diabetes Tech. and Ther., 2014, 16: Supp 1, S85-S91.

Steffes et al, "Beta-cell function and the development of diabetes-related complications in the diabetes control and complications trial" Diabetes Care 2003 26: 832-836.

Tian et al, "Modulating autoimmune responses to GAD inhibits disease progression and prolongs islet graft survival in diabetes-prone mice." Nature Medicine 1996 2: 1348-1353.

Tian et al, "Nasal administration of glutamate decarboxylase (GAD65) peptides induces Th2 responses and prevents murine insulin-dependent diabetes." J Exp Med 1996 183: 1561-1567.

(56) References Cited

OTHER PUBLICATIONS

Tisch et al, "Antigen-specific mediated suppression of beta cell autoimmunity by plasmid DNA vaccination." Immunol 2001 166: 2122-2132.

Tisch et al, "Immune response to glutamic acid decarboxylase correlates with insulitis in non-obese diabetic mice." Nature 1993 366: 72-75.

Tisch et al, "Induction of GAD65-specific regulatory T-cells inhibits ongoing autoimmune diabetes in nonobese diabetic mice." Diabetes 1998 47: 894-899.

Van Dongen et al, "Anti-inflammatory M2 type macrophages characterize metastasized and tyrosine kinase Inhibitor-treated gastrointestinal stromal tumor" Int J Cancer 2010 127: 899-909.

Verhagen et al, "Ctla-4 modulates the differentiation of inducible Foxp3+ Treg cells but IL-10 mediates their function in experimental autoimmune encephalomyelitis" PLOS One 2014 9:e108023.

Von Beust et al, "Improving the therapeutic index for CpG oliogdeoxynucleotides by intralymphatic administration" Eur J immunol 2005 35: 1869-1876.

Wahren et al, "C-peptide is a bioactive peptide" Diabetologia 2007 50: 503-509.

Wong et al, "Identification of an MHC class I-restricted autoantigen in type 1 diabetes by screening an organ-specific cDNA library" Nat. Med. 1999 5: 1026-1031.

Yoon et al, "Control of autoimmune diabetes in NOD mice by GAD expression or suppression in beta cells" Science 1999 284:1183-1187.

Axelsson et al, "Long-lasting immune responses 4 years after GAD-alum treatment in children with type 1 diabetes" PLoS One. 2011 6:e29008.

Witten et al, "Is intralymphatic immunotherapy ready for clinical use in patients with grass pollen allergy?" J. Allergy Clin. Immunol. 2013 132: 1248-1252.

Beam et al., "GAD vaccine reduces insulin loss in recently diagnosed type 1 diabetes: findings from a Bayesian meta-analysis", Diabetologia, Jan. 2017, 60(1): 43-49.

Bizzarri et al., "No Protective Effect of Calcitriol on β-Cell Function in Recent-Onset Type 1 Diabetes", Diabetes Care, Sep. 2010, 33(9): 1962-1963.

Ludvigsson et al., "Intralymphatic Glutamic Acid Decarboxylase With Vitamin D Supplementation in Recent-Onset Type 1 Diabetes: A Double-Blind, Randomized, Placebo-Controlled Phase IIb Trial", Diabetes Care, Jul. 2021, 44: 1604-1612.

Marrack et al., "Towards an understanding of the adjuvant action of aluminium", Nat Rev Immunol., Apr. 2009, 9 (4): 287-293.

Singh et al., "The Paradigm of Th1 and Th2 Cytokines", Immunologic Research, 1999, 20: 147-161.

Tavira et al., "Effect of simultaneous vaccination with H1N1 and GAD-alum on GAD65-induced immune response", Diabetologia, 2017, 60: 1276-1283.

Hannelius et al., "Efficacy of GAD-alum immunotherapy associated with HLA-DR3-DQ2 in recently diagnosed type 1 diabetes", Diabetologia, Aug. 5, 2020, 63: 2177-2181.

Martinez-Gomez et al., "Intralymphatic Injections as a New Administration Route for Allergen-Specific Immunotherapy", International Archives of Allergy and Immunology, 2009, 150: 59-65.

Mayer et al., "Defined Intestinal Regions Are Drained by Specific Lymph Nodes That Mount Distinct Th1 and Th2 Responses Against Schistosoma mansoni Eggs", Frontiers in Immunology, Oct. 23, 2020, vol. 11, Article 592325, pp. 1-15.

Van Wilsem et al., "Oral Tolerance is Determined at the Level of Draining Lymph Nodes", Immunobiol., 1995, 194: 403-414.

Herold et al., "A Single Course of Anti-CD3 Monoclonal Antibody hOKT3γ1(Ala-Ala) Results in Improvement in C-Peptide Responses and Clinical Parameters for at Least 2 Years after Onset of Type 1 Diabetes", Diabetes, 2005, 54: 1763-1769.

Herold et al., "An Anti-CD3 Antibody, Teplizumab, in Relatives at Risk for Type 1 Diabetes", The New England Journal of Medicine, 2019, 381(7): 603-613.

Lachin et al., "Impact of C-Peptide Preservation on Metabolic and Clinical Outcomes in the Diabetes Control and Complications Trial", Diabetes, Feb. 2014, 63: 739-748.

Mysliwska et al., "Enhanced Apoptosis of Monocytes from Complication-Free Juvenile-Onset Diabetes Mellitus Type 1 May Be Ameliorated by TNF-α Inhibitors", Hindawi Publishing Corporation, Mediators of Inflammation, 2014, Article ID 946209, 11 pages.

Orban et al., "Co-Stimulation Modulation with Abatacept in Patients with Recent-Onset Type 1 Diabetes: A Randomised Double-Masked Controlled Trial", Lancet, 2011, 378(9789): 412-419. doi: 10.1016/S0140-6736(11) 60886-6.

Russell et al., "Abatacept for Delay of Type 1 Diabetes Progression in Stage 1 Relatives at Risk: A Randomized, Double-Masked, Controlled Trial", Diabetes Care, 2023, 46(5): 1-9.

Feng et al., "New concept of diabetes diagnosis and prevention", China Pharmaceutical Science and Technology Press, Nov. 30, 2006, pp. 357-363.

"Ny klinisk studie med Diamyds diabetesvaccin", Diamyd Medical AB (publ), Jan. 30, 2013, https://www.diamyd.com/docs/pressClip.aspx?section=investor&ClipID=738265.

Hawa et al., "Antibodies to IA-2 and GAD65 in Type 1 and Type 2 Diabetes", Diabetes Care, Feb. 2000, 23(2): 228-233.

Hoppu et al., "GAD65 antibody isotypes and epitope recognition during the prediabetic process in siblings of children with type I diabetes", Clin Exp Immunol, 2004, 136: 120-128.

Casas et al., "Intra-lymphatic administration of GAD-alum in type 1 diabetes: long-term follow-up and effect of a late booster dose (the DIAGNODE Extension trial)", Acta Diabetologica, 2022, 59: 687-696.

Hals et al., "A 1-year pilot study of intralymphatic injections of GAD-alum in individuals with latent autoimmune diabetes in adults (LADA) with signs of high immunity: No safety concerns and resemblance to juvenile type 1 diabetes", Diabetes Obes Metab., 2023, 25: 3400-3409.

Nowak et al., "Intralymphatic GAD-Alum (Diamyd®) Improves Glycemic Control in Type 1 Diabetes With HLA DR3-DQ2", The Journal of Clinical Endocrinology & Metabolism, 2022, 107: 2644-2651.

Skyler et al., "Effects of oral insulin in relatives of patients with type 1 diabetes: The Diabetes Prevention Trial—Type 1.", Diabetes Care, 2005, 28: 1068-1076.

Ramiya et al., "Immunization Therapies in the Prevention of Diabetes", Journal of Autoimmunity, 1997, 10: 287-292.

Rudroju et al., "Comparative Efficacy and Safety of Six Antidepressants and Anticonvulsants in Painful Diabetic Neuropathy: A Network Meta-analysis", Pain Physician, 2013, 16:E705-E714.

Colwell, "Aspirin Therapy in Diabetes", Diabetes Care, 1997, 20(11): 1767-1771.

Jiang et al., "Inhibition of islet β cell apoptosis and prevention diabetes by subcutaneous administration of insulin in NOD mice", J. Cent South Univ (Med Sci), Aug. 2006, 31(4): 499-504. (English abstract included).

Li et al., "Protective effects of 1-α-hydroxyvitamin D3 on residual β-cell function in patients with adult-onset latent autoimmune diabetes (LADA)", Diabetes/Metabolism Research and Reviews, 2009, 25: 411-416.

* cited by examiner

COMBINATIONS FOR ANTIGEN BASED THERAPY

CROSS-REFERENCE TO RELATED APPLICATIONS

This application is a continuation-in-part of U.S. application Ser. No. 15/315,557, files on Dec. 1, 2016, which is a § 371 national phase of International Application No. PCT/SE2015/050651, filed on Jun. 4, 2015, which claims priority from Swedish patent application 1450678-6, filed on 4 Jun. 2014, and Swedish patent application 1451315-4, filed on 4 Nov. 2014, which are hereby expressly incorporated by reference in their entirety.

FIELD OF THE INVENTION

The present invention generally relates to the field of immunology and in particular immunotherapy. More particularly, the present invention pertains to the prevention and/or treatment of autoimmune diseases such as type 1 diabetes or autoimmune diabetes. The present invention provides compositions and combinations which are particularly useful in the prevention and/or treatment of such disease. Also provided are methods for combination therapies for treatment and/or prevention of autoimmune disease.

BACKGROUND OF THE INVENTION

The immune defence system, like many defence systems consists of numerous and mostly interactive parts. There is the innate system, that basically is thought to react via pattern recognition receptors, such as Toll-like receptors, to rather well-known and common microbial antigens (ag); and there is the acquired system which can adapt to respond to a large variety of foreign invaders and moreover create and maintain memory cells that quickly react in the event new encounters occur with the same ag.

In autoimmune disease, the adaptive immune system commonly reacts to at least one self-antigen, (auto-antigen, aag). Although not fully understood, autoimmunity may be triggered in several ways. Examples of discussed possible triggers include but are not limited to innate responses to viruses, diets, vitamins, stress, microbiomes, vaccines, antibiotics and other drugs. Genetic disposition is an additional important factor.

In the case of endogenously produced autoantigens, these are processed inside a cell and peptides thereof are transported to the cell surface in association with MHC-I molecules and presented to various cells including naïve CD8$^+$ T cells; already mature cytotoxic CD8$^+$ T cells; and/or CD8$^+$ memory effector T cells. To activate a naïve CD8$^+$ T cell to mature into a cytotoxic T cell, a secondary co-stimulatory signal associated with CD28 is needed.

An autoantigen that is not inside a cell is normally taken up by an antigen presenting cell (APC) such as a dendritic cell (DC) or macrophage, and processed peptides will be transported in association with MHC-II molecules and presented to naïve, mature or memory CD4$^+$ T cells. Also here is a second co-stimulation signal involving CD28 needed to activate the naïve CD4$^+$ T cell into a form of T helper (Th) cell. Usually two forms of Th cells are discussed: Th1; Th2.

What type of Th cell that is generated upon the encounter between the APC-MHCII-aag complex and the CD4$^+$ T cell receptor (TCR) depends on several factors including the maturity of the DC and the surrounding milieu, including but not limited to availability of IL-10, at the time of presentation. Whereas a Th1 cell secrets inflammatory cytokines including IFN-γ, and stimulates an inflammatory cell mediated response, Th2 cells typically secret IL4 and stimulate a humoral response where B-lymphocytes (BCs) produce non-cytolytic and neutralizing antibodies. Antibodies for "coating" and complement fixing (antibody dependent cellular toxicity) are usually stimulated by the Innate system.

Each B-lymphocyte (BC) expresses its unique and specific B cell receptor (BCR) in the form of an immobilized antibody molecule. Whereas TCs recognize cognate ag—as a processed peptide in the context of an MHC molecule, B cells recognize antigens in their native form (such unprocessed antigens do not normally interact with T cell activation), and with help from mostly Th2 signalling they differentiate into short lived antibody producing plasma cells, 10% of which are thought to become long-lived antigen-specific memory BCs.

It is commonly thought in the field, that insulin and insulin associated molecules, are early molecules to be involved in the process that leads to autoimmune diabetes including type 1-diabetes and latent autoimmune diabetes in the adult. Large clinical trials have been performed and are currently being performed using different insulin derived formulations in order to induce tolerance and stop or prevent the disease progression. Many other β cell antigen molecules and peptides thereof including but not limited to GAD65 have been tried for the same purpose, and others, not limited to insulin B-chain and pro-insulin and variations thereof, are being prepared for clinical development.

During development of the immune system in man, self-antigen reactive lymphocytes are thought to be clonally deleted to discriminate self from non-self. Non-self reactive T lymphocytes are saved and go on to differentiate into naïve CD4$^+$ or CD8$^+$ T cells, that can be activated upon encounter with their specific antigen. Some self-reactive lymphocytes do however escape the deletion process. More so if the self-antigen is sequestered like for example inside a cell. In the case of insulin however, as an example of an abundant molecule, relatively few insulin-reactive lymphocytes do escape the deletion process and as a consequence relatively few naïve insulin reactive CD4$^+$ or CD8$^+$ T cells exist.

Naturally occurring abundant molecules, such as for example insulin, are not usually adsorbed and presented by DCs unless this process is initiated by activated CD8$^+$ T cells and/or toll like receptor (TLR)-signalling. Therefore, and what may not have been noted in the field, the autoimmune process leading to diabetes may in many cases be initiated by escaped CD8$^+$ naïve insulin reactive lymphocytes that recognize aag directly associated with MHC class-1 on cells of the target organs. In the case of the genetically predisposed, an insulin reactive "escaped" naïve CD8$^+$ thymocyte can accordingly trigger a an inflammatory process including generation of CD8$^+$ cytotoxic cells which in turn may induce cytokines that alert the innate system including raising causing BCs to produce insulin antibodies. Some β cells will succumber and release sequestered antigens, such as for example GAD65, for which an abundant amount of naïve CD4$^+$ and CD8$^+$ TCs exist. GAD65 may in addition have commonalities with certain viral structures that further stimulates TLR-like signalling.

While the autoimmune reaction processes, counter inflammatory mechanisms develop, such as for example expression of CTLA4 molecules and IL-10 secretion. Since in the case of insulin, the ADC-MHCII contribution to the emerging autoimmune disease is weak, such compensatory mechanisms induce tolerance to insulin in an autoantigen-specific manner. GAD molecules however is taken up, processed DCs and GAD peptides are presented to naïve CD4+TCs, activating them into T helper cells. Thus a transcient immunity reaction to insulin is replaced by a more robust reaction towards GAD. This explains why in many genetically predisposed small children the first autoantibody often is to insulin, and why such antibodies often disappear as disease progresses.

Mocellin, Cytokine Growth Factor Rev. 2004, The multifaceted relationship between IL-10 and adaptive immunity: putting together the pieces of a puzzle, describes how Interleukin-10 (IL-10) is a pleiotropic cytokine that modulates the function of several adaptive immunity-related cells. Although generally considered an immunosuppressive molecule, IL-10 possesses immunostimulatory properties in vivo models. As an example locally produced IL-10 by pancreatic islet cells stimulate progression of autoimmunity in the NOD mouse, whereas systemic administration may have a β cell preserving and anti-inflammatory effect. A summary on the relationship between IL-10 and infectious diseases, autoimmunity, allergy, cancer and transplantation involving adaptive immunity is provided.

Russel et al, Islets. 2014, The impact of anti-inflammatory cytokines on the pancreatic β-cell, more recently presented evidence that anti-inflammatory molecules such as interleukin (IL)-4, IL-10 and IL-13 can exert a direct influence of β-cell function and viability and that the circulating levels of these cytokines may be reduced in type 1 diabetes and proposed that targeting of anti-inflammatory pathways might offer therapeutic potential in type 1-diabetes.

Calcinaro et al, Diabetologia. 2005, Oral probiotic administration induces interleukin-10 production and prevents spontaneous autoimmune diabetes in the non-obese diabetic mouse, concluded thatearly oral administration of probiotic bacteria prevented diabetes development in NOD mice and was associated with increased IL-10 expression in the pancreas, where IL-10-positive islet-infiltrating mononuclear cells were detected.

Van Dongen et al, Int J Cancer. 2010 Aug. 15; 127(4): 899-909. doi: 10.1002/ijc.25113. Anti-inflammatory M2 type macrophages characterize metastasized and tyrosine kinase inhibitor-treated gastrointestinal stromal tumors (GIST) reports that tumors treated with the tyrosine kinase inhibitors imatinib and sunitinib induced secretion of anti-inflammatory IL-10 in macrophage cultures, indicating that treatment with these inhibitors might contribute to an immune suppressive microenvironment in GIST. Overall, data revealed GIST as an active site of tumor-immune interaction in which suppressive mechanisms overrule potential antitumor responses. Tyrosine kinase inhibitors might promote this negative balance.

Louvet et al, Proc Natl Acad Sci USA. 2008, Tyrosine kinase inhibitors reverse type 1 diabetes in nonobese diabetic mice reports how tyrosine kinase (TK) inhibitors offer opportunities for the treatment of autoimmune diseases. Treatment with imatinib (Gleevec) prevented and reversed T1D in NOD mice. Similar results were observed with sunitinib (Sutent). Another TK inhibitor, PLX647 showed only marginal efficacy whereas a soluble form of platelet-derived growth factor receptor (PDGFR), PDGFRβIg, rapidly reversed diabetes. Imatinib treatment led to durable remission and long-term efficacy and tolerance is likely to depend on inhibiting a combination of tyrosine kinases supporting the use of selective kinase inhibitors for the treatment of T1D.

Agostinoet et al, J Oncol Pharm Pract. Epub 2010, Effect of the tyrosine kinase inhibitors (sunitinib, sorafenib, dasatinib, and imatinib) on blood glucose levels in diabetic and nondiabetic patients in general clinical practice, describes how tyrosine kinase inhibitors (TKIs) influenced the blood glucose (BG) concentrations in patients treated with dasatinib, imatinib, sorafenib, and sunitinib. All showed significant declines in BG. Although the mechanism for the hypoglycemic effect of these drugs is unclear, c-kit and PDGFRβ were common target kinases.

Adorini, Ann N Y Acad Sci. 2003, Tolerogenic dendritic cells induced by vitamin D receptor ligands enhance regulatory T cells inhibiting autoimmune diabetes, reports that 1,25-Dihydroxyvitamin D(3) induces DCs with a tolerogenic phenotype, characterized by decreased expression of CD40, CD80, and CD86 co-stimulatory molecules, low IL-12, and enhanced IL-10 secretion. Treatment with 1,25-(OH)(2)D(3) induced tolerance to mouse islet allografts associated with impaired development of type 1 CD4(+) and CD8(+) cells and an increased percentage of CD4(+)CD25(+) regulatory cells and also inhibited diabetes development at non-hypercalcemic doses, suggesting vitamin D as an approach for treatment of type 1-diabetes.

Heine et al, Eur J Immunol. 2008, 1,25-dihydroxyvitamin D(3) promotes IL-10 production in human B cells, reports that 1,25-dihydroxyvitamin D(3) (calcitriol) inhibits expression of IgE by B cells and enhances expression of IL-10 by dendritic cells and T cells. The molecular link in activated B cells between vitamin D signalling, expression of IL-10, and their ability to produce calcitriol from its precursor, suggest that 25-hydroxyvitamin D(3)) can be used as a modulator of immune responses.

Niiro et al, Biochem Biophys Res Commun. 1998, MAP kinase pathways as a route for regulatory mechanisms of IL-10 and IL-4 which inhibit COX-2 expression in human monocytes, describes how mitogen-activated protein kinases (MAPKs) are activated and play an important role in regulating the expression of pro-inflammatory molecules in monocytes/macrophages. Lipopolysaccharide (LPS)-stimulated human monocytes induce COX-2 protein and COX-2 mRNA expression as well as the signal-regulated protein kinase (ERK)2 and p38 MAPK in monocytes. The induction of COX-2 mRNA, COX-2 protein, and prostaglandin (PG) E2 by LPS was inhibited by the specific inhibitors of ERK and p38 MAPK. Interleukin (IL)-10 similarly inhibited COX-2 expression. LPS-induced phosphorylation and activation of ERK2 and p38 MAPK were significantly inhibited by IL-10, suggesting that the inhibition by IL-10 of the LPS-induced expression of pro-inflammatory molecules could be ascribed to the regulatory effects of both cytokines on MAPK activation.

Obermajer et al, Blood. 2011, Positive feedback between PGE2 and COX2 redirects the differentiation of human dendritic cells toward stable myeloid-derived suppressor cells, describes how dendritic cells (DCs) and myeloid-derived suppressor cells (MDSCs) show opposing roles in the immune system.

Cyclooxygenase 2 (COX2) is the key regulator of PGE(2) synthesis and a determining factor in redirecting the development of CD1a(+) DCs to CD14(+)CD33(+)CD34(+) monocytic MDSCs. Exogenous PGE(2) and such diverse COX2 activators as lipopolysaccharide, IL-1β, and IFN-γ all induce monocyte expression of COX2, blocking their differentiation into CD1a(+) DCs and inducing endogenous PGE(2), IDO1, IL-4Rα, NOS2, and IL-10, typical MDSC-associated suppressive factors. The disruption of COX2-PGE(2) feedback using COX2 inhibitors or EP2 and EP4 antagonists suppresses the production of MDSC-associated suppressive factors and the CTL-inhibitory function of fully developed MDSCs from cancer patients. The central role of COX2-PGE(2) feedback in the induction and persistence of MDSCs highlights the potential for its manipulation to enhance or suppress immune responses in cancer, autoimmunity, or transplantation.

Lieb, Med Hypotheses. 2007, Antidepressants, prostaglandins and the prevention and treatment of cancer, reports that a putative mechanism of carcinogenesis are up-regulation of cyclooxygenase, the synthesis and expression of oncogenes, viral activation, signal disruption, failed apoptosis, tumor initiation and promotion, angiogenesis, metastasis, immunosuppression, telomerase activity andautoimmunity. All are regulated by prostaglandins. Observable and radiographic regression of cancer has been documented in patients taking non-steroidal, anti-prostaglandin drugs such as indomethacin and ibuprofen.

Kim, et al, Immune Netw. 2010, Cyclooxygenase Inhibitors, Aspirin and Ibuprofen, Inhibit MHC-restricted Antigen Presentation in Dendritic Cells, reports that NSAIDs have immunomodulatory effects on T and B cells and that ibuprofen inhibit MHC class I and class II-restricted presentation of antigen in dendritic cells (DCs). Ibuprofen did not inhibit the phagocytic activity of DCs, the expression level of total MHC molecules and co-stimulatory molecules on DCs. Ibuprofen rather increased the expression level of total MHC molecules and co-stimulatory molecules on DCs. The results demonstrate that ibuprofen inhibits the intracellular processing of the phagocytosed antigen, and suggest that prolonged administration of NSAIDs in high doses may impair the capability of DCs to present antigens in association with MHC molecules.

Gribben et al, Immunology 1994, CTLA4 mediates antigen-specific apoptosis of human T cells, describes how the CTLA4 molecule is a T cell restricted molecule induced by TCR or CD28 activation. During an ongoing immune response there is a balance between proinflammatory and non-proinflammatory signals. Cross-linking of CD28 or the common binding region of CD28/CTLA4 by mabs or the natural ligands B7-1 and 2 provides a positive costimulatory signal resulting in proinflammatory IL-2 upregulation. In fact crosslinking of CTLA4 can provide a weak costimulatory signal to CD28. After T cell activation CD28 expression is down-regulated and CTLA4 up-regulated. At such times crosslinking of CTLA4 in the absence of CD28 costimulation may induce deletion of previously activated T cells, which indicates that CTLA4 can both costimulate and induce deletion depending on the activation state of the T cell.

Posadas et al, Clinical Immunology 2009, Abatacept in the treatment of rheumatoid arthritis, describes that in rheumatoid arthritis (RA), T cells and several other cells including dendritic cells DCs, macrophages and fibroblasts express markers of activation such as CD28 and cytotoxic T lymphocyte antigen 4 (CTLA4). In the peripheral blood naïve T cells need two signals to become activated to their full functional potential: i) an antigen in the context of an MHC molecule on the antigen presenting cell (APC) presented to the corresponding antigen specific T cell receptor (TCR) on the T cell; and ii) ligation of CD28 on the T cell with CD80/86 on APCs. Stimulation of naïve T cells by cognate antigen without costimulation results in T cell anergy, whereas ligation of costimulatory molecules on the T cells in the absence of cognate antigen has no effect on the T cell.

One of the surface molecules that are upregulated on the activated T cell after successful stimulation with the two signals is CTLA4. It binds to CD80/80 with higher avidity than CD28. This not only blocks CD28 from binding but CTLA4 also induces inhibitory signals into the newly activated T cell.

Abatacept (an Fc modified CTLA4 immunoglobulin) is a T cell depleting, immunomodulating, fusion protein consisting of the extracellular portion of human CTLA4 and the heavy chain of human IgG1. It blocks the costimulatory signal involved in activation of naïve T cells. Its ligation with CD80/86 on APCs may also interfere with and reduce CD80/86 induced IL-6, which may downregulate inflammatory cytokines such as IL-1@, IFN gamma, and IL-17. Further abatacept ligation with CD80/86 may induce indoleamine dioxygenase (IDO) in APCs, which may in turn may induce anergy in T cells, as well as downregulate paracrine activation of naïve T cells by activated T cells.

Contradictory opinions have been presented regarding abatacepts ability to influence the recall, restimulation, of memory CD4$^+$ T cells. CD80/86 expressed on B cells may yet be a further path where abatacept may carry out an immunomodulating function.

Patakas et al, abstract #723 ACR/ARHP, 2013, Abatacept is Highly Effective At Inhibiting T cell Priming and Induces a Unique Transcriptional Profile In CD4$^+$ T Cells, showed how sc priming with ovalbumin in the presence of abatacept produced large amounts of IL-2, thereby resembling naïve T cells exposed to antigen for the first time. These T cells included less Tregs and CD4$^+$ T cells than other (not primed or naïve) T cell populations, and their state were accompanied by an inhibition of the activation of dendritic cells at the transcriptional level. Patakas concluded that while abatacept significantly modulates the T-DC communication resulting in defective cell priming this is distinct from anergic tolerance.

Orban et al, Lancet 2011, Co-stimulation modulation with abatacept in patients with recent-onset type 1 diabetes: a randomised, double-blind, placebo-controlled trial, reports that abatacept significantly preserves endogenous insulin secretion as measured by stimulated C peptide, over the initial 6 months as compared with placebo, then declines in parallel with the placebo group. The early beneficial effect is thought to be due to that abatacepts blocks the costimulatory B80/86-CD28 signal preventing activation of naïve T cells. The after 6 months successive decline in β cell function was speculated to be due to that continuous T cell activation diminished as the disease progress.

Although Orban mentions that activation of naïve T cells need two signals, whereas one is comprised by an antigen presented in the context of an MHC molecule on an APC; and the other is a costimulatory signal involving the CD28 molecule on the T cell, no specific antigen was used in the trial. This may be ground for speculation that while abatacept initially and successfully prevents activation of naïve T cells into cytotoxic T cells, this may eventually be counteracted and/or compensated for by other parts of the immune system, such as for example increased secretion of IL-2, and when this has occurred, the window for inducing tolerance to a specific antigen is missed.

Orban et al, Diabetes Care 2013, Costimulation Modulation With Abatacept in Patients With Recent-Onset Type 1 Diabetes: Follow-up 1 Year After Cessation of Treatment, subsequently reported continued beneficial effect one year after cessation of drug administration although differences between the active arm and placebo diminished. Thus did 35% of patients in the active arm have a peak stimulated C peptide >0.2 nmol/l compared to 30% for placebo subjects at 36 months after commencement of treatment. It was pointed out that there was a lack of effect with abatacept treatment in DR3-negative patients.

The two Orban studies mentioned above indicate that the immune regulation of abatacept as a stand alone therapy in recent onset type 1 diabetes patients is not sufficient to have a lasting β cell function preservation effect.

Verhagen et al, PLOS 2014, CTLA-4 Modulates the Differentiation of Inducible Foxp3+ Treg Cells but IL-10 Mediates Their Function in Experimental Autoimmune Encephalomyelitis, concludes that presence of IL-10 is an important factor for enhancing the suppressive effect of Tregs.

GAD65 (the 65 kd isoform of Glutamic Acid Decarboxylase), is a major β cell auto-antigen, as it is produced in the islets with increased release as response to β cell stimulation. This protein has been shown to deeply influence the autoimmune immune process. Numerous studies have shown that GAD can prevent diabetes in experimental animals. The similarity of GAD with viral proteins may be important for the therapeutic action. The observed effect, even after the start of the immune process, suggests that it might be possible to expect the same effect in humans. Recombinant GAD was formulated in aluminium hydroxide (alum) and in a phase II study in LADA patients, the administration of one low dose, Diamyd® 20 μg, led to improved β cell function for up to 2 years compared to the placebo treated group, with no side effects. Also other doses were tried: 4 μg showed no effect, 100 μg showed a similar effect as 20 μg, while 500 μg showed no effect. Association with change in the ratio of $CD4^+CD25^+/CD4^- CD25^-$ cells was found, indicating a mechanism for the effect. With this background a phase II study in recent onset Type 1 diabetic patients 10-18 years was performed. Patients were randomized to either 20 μg GAD-alum (Diamyd®) sc at day 1 and 30, or placebo. The effect still after 30 months was remarkable, and clearly both statistically and clinically significant, with about half of the C peptide decline in the GAD treated group compared with the placebo group. Patients with a diabetes duration <3 months had a remarkably good effect with no or minimal decline of β cell function during the follow-up of the first 15 months. Still after 48 months patients treated with <6 months duration had significantly preserved C peptide and no adverse events.

Subsequently phase III trials were initiated in European in the US. In the European trial 334 patients were recruited into three arms, one arm with GAD-alum (Diamyd®) 20 μg at day 1, 30, 90 and 270, another arm with GAD-alum 20 μg at day 1 and 30, and placebo at day 90 and 270 and a third arm with placebo at day 1, 30, 90 and 270. Although a positive trend was seen (16% efficacy, p=0.1) the primary endpoint, serum C peptide AUC after a mixed meal tolerance test (MMTT) at 15 months was not met. This prompted early closure of the phase III trials. However, the European phase III trial did show statistically significant efficacy in some pre-specified subgroups. Furthermore, 45 Swedish patients had passed the 30 month's visit when the study was stopped, and those 15 patients who had received two doses of GAD-alum (Diamyd®) 20 μg showed a significant preservation of C peptide after 30 months compared with placebo. It was noted that these Swedish patients were the ones without efficacy at 15 months, while efficacy was found at 15 months in the non-Nordic patients. It was concluded that while partly effective, GAD-alum may need to be combined with other compounds in order to become part of a clinically effective treatment regimen for type 1 diabetes.

Denes et al, Diabetes Technol Ther. 2010, Autoantigens plus interleukin-10 suppress diabetes autoimmunity, reported that whereas recombinant vaccinia virus (rVV) strains expressing the immunomodulatory cholera toxin B subunit (CTB) fused to a fragment of the autoantigen glutamic acid decarboxylase (GAD65) or the immunosuppressive cytokine interleukin-10 (IL-10) were independently able to generate only low levels of immune suppression of type 1 diabetes mellitus (T1DM) in the NOD mouse, a vaccinia virus (VV)-mediated combination of CTB::GAD fusion and IL-10 proteins showed to be a more effective and durable immunotherapeutic strategy for T1DM.

Robert et al, Diabetes. 2014, Oral delivery of glutamic acid decarboxylase (GAD)-65 and IL10 by *Lactococcus lactis* reverses diabetes in recent-onset NOD mice, more recently showed that oral delivery of live *Lactococcus lactis* (LL) bacteria for controlled secretion of the T1D autoantigen GAD65370-575 peptide and the anti-inflammatory cytokine interleukin-10, in combination with short-course low-dose anti-CD3, preserved functional β-cell mass in recent-onset NOD mice.

Skyler et al, Diabetes 2011, Stopping Type 1 Diabetes, Attempts to Prevent or Cure Type 1 Diabetes in Man (which including references in entirety is incorporated herein), a combination regimen involving an immune modulator and an antigen-specific therapy provides a rational for a longer lasting treatment of T1D.

Staeva et al, DIABETES, VOL. 62, JANUARY 2013, Recent Lessons Learned from Prevention and Recent-Onset Type 1 Diabetes Immunotherapy Trials (which including references in entirety is incorporated herein), report the state of the art of current thinking and recommends evaluating combination therapies including self-antigens and anti-inflammatory compounds.

Skyler, DIABETES TECHNOLOGY & THERAPEUTICS, Volume 16, Supplement 1, 2014, Immune Intervention for Type 1 Diabetes, 2012-2013, (which in entirety is incorporated herein), reviews recent trials in the field.

Rigby et al, Current Opinion Endocrinol Diabetes Obes 2014, 21:271-278, Targeted immune interventions for type 1 diabetes: not as easy as it looks! (which including references in entirety is incorporated herein) describes many of the efforts to combat autoimmune diabetes and concludes that despite nearly a dozen trials with many hundreds of participants, no monotherapy has been found and that: a) different subpopulations of patients with T1D seem to respond differently to immune interventions, suggesting significant heterogeneity; b) an effective therapy must combine inhibition of Teff cells (by depletion, enhanced suppressibility, or both), with stimulation of Tregs (by increased frequency or function, including ablation of the proinflammatory milieu); and this may require combinations comprising a Teff-depleting agent, a Treg-boosting agent, and an antigen.

As referenced above several monotherapies and combination regimens including a variety of compounds have shown promising effects in prevention and treatment of autoimmune diabetes in the mouse model. However, transfer of such regimens to man have all failed to show a clinically meaningful effect. Thus there remains a formidable need to relieve societies and patients from the devastating disease autoimmune diabetes and its long term complications. It is a subject of the present invention to disclose methods and compositions for prevention and treatment for the autoimmune component of T1D and LADA, paving the way for endogenous, or by other methods accomplished, increase of functional β cell mass.

SUMMARY OF THE INVENTION

In one aspect, the present invention relates to a method for prevention and/or treatment of an autoimmune disease, comprising administering to a subject a composition, said composition comprising at least one β cell autoantigen, by intralymphatic injection or injection directly into a lymph node.

In one embodiment, the present invention relates to a method for prevention and/or treatment of an autoimmune disease selected from the group consisting of type 1 diabetes, autoimmune diabetes and latent autoimmune diabetes, comprising administering to a subject a composition, said composition comprising glutamic acid decarboxylase, by injection directly into a lymph node.

In one embodiment, the method is for treatment of type 1 diabetes.

In one embodiment, the method is for increasing or preserving endogenous insulin production, or mitigating decrease of endogenous insulin production, in a type 1 diabetes patient.

In one embodiment, the method is for lowering long term blood glucose levels, as measured by HbA1c, in a type 1 diabetes patient.

In one embodiment, the method is for lowering requirements for external insulin, in a type 1 diabetes patient.

In one aspect, the present invention relates to a method for prevention and/or treatment of an autoimmune disease, comprising administering a composition, said composition comprising at least one β cell autoantigen, to a subject having a serum vitamin D level above 50 nanomol/liter.

The present invention discloses the method of using anti-inflammatory compounds and autoantigens in combination with methods to render dendritic antigen presenting cells (APCs) more "tolerizing" when presenting said autoantigens to the immune system.

The present invention discloses methods where combinatorial regimens including anti-inflammatory compounds, autoantigens and vitamin D can be effectively used as prevention and treatment methods for T1D and other autoimmune diseases.

In a further aspect, the present invention relates to a method for prevention and/or treatment of an autoimmune disease, comprising administering to a subject at least one β cell autoantigen, in increasing doses over a period of weeks, months, or years.

In a further aspect, the present invention relates to a composition comprising a plurality of particles, each having immobilised on its surface at least one first and at least one second antigen, wherein the first antigen is a β cell autoantigen, and the second antigen is either a tolerogen or a β cell autoantigen, the composition further optionally comprising pharmaceutically acceptable adjuvants, excipients, solvents, and/or buffers.

In a further aspect, the present invention relates to a composition comprising i) at least one β cell autoantigen, and at least one of iia) an IL-10 inducing compound selected from the group consisting of vitamin D, vitamin D analogs, tyrosine kinase inhibitors, gamma-amino butyric acid, and gamma-amino butyric acid analogs; and iib) a compound that reduces the dendritic cells' ability to activate naïve CD4$^+$ T cells, such as a cyclooxygenase inhibitor, a CTLA-4 compound or a TNF α inhibitor; and optionally pharmaceutically acceptable adjuvants, excipients, solvents, and/or buffers.

In a further aspect, the present invention relates to a pharmaceutical kit comprising i) a composition comprising a β cell autoantigen, and at least one of iia) a composition comprising an IL-10 inducing compound selected from the group consisting of vitamin D, vitamin D analogs, tyrosine kinase inhibitors, gamma-amino butyric acid, and gamma-amino butyric acid analogs; and iib) a composition comprising a compound that reduces the dendritic cells' ability to activate naïve CD4$^+$ T cells, such as a cyclooxygenase inhibitor, a CTLA-4 compound or a TNF α inhibitor.

In a further aspect, the present invention relates to a β cell autoantigen for use in a method according to the invention.

Preferred embodiments of the invention are set out in the dependent claims.

Definitions

All terms and expressions as used herein are intended to have the meaning given to them by the person skilled in the art at the filing date of the present application, unless any other expression is evident from the context of this disclosure. However, for the sake of clarity, some terms and expressions are explicitly defined below.

An "autoantigen" or "self-antigen" is an endogenous tissue constituent that has the ability to interact with autoantibodies and cause an immune response. A "β cell autoantigen" is an autoantigen originating from pancreatic β cells.

An "autoantibody" is an antibody that reacts with autoantigens of the organism that produced them.

The term "vitamin D" includes vitamin D$_2$ and vitamin D$_3$. "vitamin D analogs" include without prejudice ergocalciferol, dihydrotachysterol, Alfacalcidol, calcitriol, colecalciferol, and calcifediol, and combinations thereof, as well as any other vitamin D analog classified in group A11CC of the Anatomical Therapeutic Chemical Classification System.

The term "cyclooxygenase inhibitors", or "cox inhibitor", relates to compounds that combine with cyclooxygenase and thereby prevent its substrate-enzyme combination with arachidonic acid and the formation of eicosanoids, prostaglandins, and thromboxanes. A subgroup of the cyclooxygenase inhibitors is the cyclooxygenase-2 inhibitors, which have specificity for cyclooxygenase-2.

The term "TNF α inhibitor" relates to compounds that inhibits the action of Tumour Necrosis Factor α (TNF α), and includes adalimumab, certolizumab, etanercept, golimumab, infliximab, as well as any other compound classified in group L04AB of the Anatomical Therapeutic Chemical Classification System.

An "epitope" is the surface portion of an antigen capable of eliciting an immune response and of combining with the antibody produced to counter that response, or a T cell receptor.

The term "gamma-amino butyric acid analogs" includes vigabatrin and baclofen.

Expressions using the singular "a", "an" and the like shall be construed as including the plural.

As used herein, "coadministration" refers to administering the compounds of the regimen of the present invention so that their dosing regimens overlap. They do not need to be administered at the same time.

The abbreviation "T1D" stands for "type 1 diabetes".

DETAILED DESCRIPTION OF THE INVENTION

At the time when a first autoantibody to insulin appears in a genetically predisposed individual, such as for example but not limited to a DR3-haplotype individual and no other autoantibodies are detected, this may mean that GAD-reactive CD8$^+$ and CD4$^+$ TCs have not yet been activated, which offers a window of opportunity to completely stop the disease with anti-inflammatory and/or lymphocyte differentiation inhibitors alone without the use of a β cell antigen, as the autoimmunity to insulin is likely to be self-eliminated by counteracting mechanisms. In this situation with few if any GAD-reactive activated CD4$^+$ T helper cells yet produced, it is important to direct activation away from the pro-inflammatory Th1 type. In GAD antibody positive individuals and/or diabetes patients, GAD and other β cell antigens formulated in alum, usually considered as a Th2 driving adjuvant, may be added for antigen specific tolerization purposes. While this may produce more Th2-cells and Tregs than pro-inflammatory cells, several factors including internal environmental factors may nullify tolerizing effects. Therefore it may not be sufficient to use Th2 driving formulations of autoantigens as monotherapies and the present invention discloses compositions and combination regimens to enhance β cell tolerization protocols.

Previous attempts to induce immune regulation in autoimmune diseases by administering monotherapies such as GAD and insulin antigens; anti-inflammatory compounds such as antibodies to CD3, CD20; thymoglobulin, abatacept, alefacept or TNF α inhibitors such as etanercept have shown some efficacy, but the duration of these effects or their efficacy after disease presentation are limitations for bringing these approaches into the clinic. The present invention discloses a novel strategy for treatment and prevention of autoimmune diseases in Vit D enforced DCs act synergistically with autoantigen and anti-inflammatories in order to provide various degrees of effect.

The present invention thus provides means (e.g., methods, compositions and combinations) for the prevention and/or treatment of autoimmune diseases, such as autoimmune diabetes.

The present invention utilizes the knowledge that vitamin D (Vit D) enforces immature dendritic cells (DCs) to be more tolerogenic, which so far has not proved to be sufficient to alter the course of any autoimmune disease, and combines administration of Vit D with administration of a self-antigen, associated with said autoimmune disease, in a timely fashion, thus enforcing the tolerogenic immunomodulation of the administered self-antigen.

To further enhance the tolerogenic milieu at which DCs present self-antigens to the immune system in a subject with adequate Vit D serum concentration, the present invention discloses the finding that a combination regimen using a common anti-inflammatory compound together with a autoantigen is suitable for treatment and prevention of T1D.

Beyond its potential synergistic effects, another advantage of co-administration of the compounds of the present invention relates to the problem that autoimmune disorders often include autoimmune responses against multiple self-antigens. It may be difficult to attempt to anergize or delete all of the autoaggressive lymphocytes using direct antigen-specific tolerization with all of their cognate antigens, because all of the cognate antigens may not be known. For example, type 1 diabetes (T1D) is thought to be caused by autoaggressive lymphocytes that enter the islets of Langerhans, where they destroy β-cells. Activation of such cells is probably multi-factorial involving a genetic predisposition, environmental triggers such as viruses and maybe damage to the pancreas (islets cells), for example caused by a local pro-inflammatory reaction.

Since the autoaggressive process is usually fairly advanced when pre-diabetic human individuals are identified by screening for islet-cell antibodies, one can assume that aggressive responses to more than one islet-antigen will be ongoing during this stage of the disease. Furthermore, chronic non-specific systemic immune suppression is not considered an option, since diabetes frequently affects young individuals and lifelong immune suppression is associated with side effects that are unacceptable compared to even insulin therapy alone.

Therefore, a curative immune-based intervention with specificity and low systemic side effects is very desirable. The present methods circumvent the problem of multiple self-antigenic targets, because the coadministration of the compounds of the present invention may be sufficient to reestablish tolerance to multiple self-antigens that are targets in an autoimmune disorder.

The present methods also circumvent the problems of chronic non-specific systemic immune suppression, because the coadministration of the compounds of the present invention can reestablish long-term tolerance without the need for continuous life-long dosing.

Without being bound by theory, the invention provides that the coadministration of the compounds of the invention has the potential to synergistically establish long-term tolerance in part by inducing the activation/expansion of regulatory T cells (and also regulatory antigen presenting cells (APCs)).

A number of different phenotypes of regulatory T cells have been described. They can arise after thymectomy and can be induced after systemic immune modulation. Their effector functions are not fully known. They appear to be part of the immune system's intrinsic balance and their loss results in severe immune dysregulation and autoimmunity. Th2-like regulators with defined antigen specificity have been described. They are thought to act as bystander suppressors and arise after antigen-specific immunization. Homann et al., J. Immunol. (1999) 163:1833-8. Depending on their effector function they have been termed Th3 (TGF-β producers). These cells are antigen specific lymphocytes with specialized effector functions and do not behave like Th2 cells. Applying the so-called Th1/Th2 paradigm to these cells can therefore be misleading.

Bystander suppression relates to the phenomenon of antigenic spreading. Antigenic spreading is thought to be an essential component during the progression of local autoimmune processes. One can therefore assume that when patients have several autoantibodies, the autoaggressive response may involve many self-antigens (or "autoantigens"). Since a majority of the autoantigens might not be identified for a particular autoimmune disorder, it is not possible to tolerize each autoaggressive specificity with a therapeutic regimen that involves knowledge of the respective MHC restriction element and peptide. The induction of regulatory cells by the present methods has several advantages in this situation. It is known for example, that regulatory T cells in T1D can act locally in the lymph nodes and islets as bystander suppressors, which means that they can suppress aggressive lymphocytes with other auto-antigenic specificities. This can occur by modulating antigen presenting cells (APCs), for example, by secretion of cytokines with immune modulatory function. Thus, such bystander suppressor T regulatory cells can dampen autoaggression to several other autoantigens without knowing their precise specificity.

Presence of a first autoantibody to an abundant 1st antigen or self-antigen such as for example insulin in a genetically predisposed individual, while no autoantibodies to at least one more sequestered (less abundant) 2nd self-antigen(s) are detected, may offer a window of opportunity to stop a potential emerging disease process in its tracks using anti-inflammatory means and/or lymphocyte differentiation inhibitors alone. In fact as the inflammatory response to such weak 1st self-antigen may be fuelled by relatively few, from the clonal deletion process in thymus escaped insulin specific auto reactive CD8$^+$ and CD4$^+$ T cells (TCs), inflammation may fade and said 1st antigen may in some embodiments be used as a tolerogen inducing tolerance to other, perhaps more sequestered or uncommon autoantigens, for which more escaped naïve auto reactive CD8$^+$ and CD4$^+$ T cells (TCs) are available for activation.

In situations where autoimmunity has been triggered to more potent autoantigens such as for example GAD65 in the case of autoimmune diabetes, and which is able to drive the disease process it may not be sufficient to use anti-inflammatory means and/or lymphocyte differentiation inhibitors alone, without the use of said potent autoantigens for induction of active tolerization. On the other hand, use of one potent autoantigens only, for example GAD65 formulated in an adjuvant such as aluminiumhydroxide (here "alum"), usually considered a Th2 driving adjuvant, may result in activation of not only regulatory components, but also of proinflammatory and/or cytotoxic molecules and cells, not limited to molecules belonging to the innate immune system, macrophages, dendritic cells, B cells (BCs), T cells (TCs) or other factors including environmental factors that may contribute to counteracting tolerization. Moreover, other less Th2 driving adjuvant formulations may be used, such as saline or human serum albumin. Therefore it may not be sufficient to use formulations of single autoantigens as monotherapies and the Present Invention discloses compositions and methods using at least two autoantigens to enhance the specific tolerization effect of administered autoantigens formulated in alum, saline or human serum albumin.

The Present Invention provides in one aspect at least one pharmaceutical composition comprising at least one antigen. The at least one pharmaceutical composition according to the invention may therefore in some embodiments comprise at least two antigens. According to certain other embodiments, the at least one composition comprises at least three autoantigens. According to certain other embodiments, the at least one composition comprises at least four autoantigens. According to certain other embodiments, the antigens may be formulated in separate compositions. Most preferred is that all antigens according to the invention are formulated in the same composition. In some embodiments all antigens are autoantigens, in some other embodiments some or all antigens are antigens (tolerogens) to which the immune system has developed a regulatory response and thereby able to influence the reaction to other autoantigens in a tolerant way.

It is a subject of the present invention to disclose compositions, regimens and methods enabling induction of tolerance to self structures being attacked in autoimmune disease. In one specific embodiment at least two antigens are associated with one carrier particle, thus exposing one immune cell from the adaptive immune system to at least two antigens with various influence on said immune cell resulting in a modified response to the self structure subject to the autoimmune attack.

By adsorbing, binding or incasing a protein or peptide antigen to a carrier particle to which the immune system reacts, and inserting the particles into human tissue by e.g. subcutaneous injection, the protein or peptide can be targeted for ingestion by the immune system. Likely this ingestion is performed by dendritic cells or macrophages (antigen presenting cells, APCs). Some of the proteins or peptides ingested in this process will be presented to the adaptive immune system by HLA (MHC) proteins and an adaptive immune reaction will follow. The adaptive response will be influenced by the activity levels of the innate immune system, and by immune responses that exist towards any antigens that are presented by the HLA proteins in the process. These influencing proteins can be the particle bound peptides or proteins, or native proteins, autoantigens or tolerogens (antigens to which the immune system reacts in a tolerogenic way) that are ingested and presented in the same process. If these proteins are ingested by the same immune cell they will be presented together by the HLA proteins on the cell surface.

The presentation of non-native peptides to the immune system may by influence from signals from the innate immune system in response to tissue disruption, be of Th2 character. Endogenous antigens including autoantibodies and RNA-nucleotides etc. may do the same. A native protein, or a protein to which a response already exists, will set off signaling by the adaptive immune cells, which will influence the total immune response, and might activate tolerogenic signals or a preexisting Th1 reaction. If the signaling induced by an injection procedure and by the interaction of naïve immune cells and antigen presenting immune cells, is stronger than the pre-existing response, a new immune response including memory will form.

If a combination of proteins resting on the same particle carriers are injected and ingested and presented by the same APC, the effects will be additive by expanding the number of possible adaptive immune cells to interact with, leading to an increased chance of forming a novel immune reaction in spite of a possible pre-existing reaction to one of the proteins.

If a protein autoantigen is injected together with another protein (native or foreign) on the same particle carrier to which an immune response already exists, the immune response to the antigen will be largely influenced by the response that the immune system already has established to the accompanying antigens. If the accompanying antigens are native proteins to which central regulatory T cells exist (such as for example IL10, insulin, Humans Serum Albumin, Hemoglobin) the response will be driven towards tolerance. If these proteins are antigens that the person has already been immunized with, such as is often the case with diptheria or tetanus toxoid, the immune response will be influenced by these existing reactions (which mostly are inflammatory reactions).

The present invention includes methods for treating auto-immunity and/or establishing or inducing tolerance by the coadministration of the compounds of the invention. Besides autoimmune diseases, present methods may also be used to establish tolerance to allergens, where allergenic peptides or proteins are coadministered with compounds of the invention where antigens instead of being self antigens are allergens (antigens) specific to the allergic disease.

It is understood that the details given herein with respect to one aspect, in particular details about the autoantigens, Influencing antigens, the IL-10 inducing compound, and compound that reduces the immune system's ability to activate naïve TCs and BCs and recall responses from activated and memory lymphocytes, the timing and mode of administration, apply mutatis mutandis to all other aspects of the invention.

Methods

In one aspect, the present invention relates to a method for prevention and/or treatment of an autoimmune disease, comprising administering a composition, said composition comprising at least one β cell autoantigen, to a subject having a serum vitamin D level above 50 nanomol/liter. Each of the at least two molecules may thus influence the reaction of the adaptive immune cell to which the antigens are presented.

The subject may have a serum D vitamin level between 50-150 nanomol/liter, such as 60-100 nanomol/liter, 75-100 nanomol/liter or 100-150 nanomol/liter.

The method may comprise a pretreatment of the subject to adjust the serum vitamin D level, and such pretreatment may comprise administration of vitamin D and/or vitamin D analogs, and/or exposure to UVB-radiation, preferably for between 7 to 90 days before administration of the composition comprising at least one β cell autoantigen to said subject.

The method may further comprise administration of vitamin-D and/or vitamin D analogs in an amount of 7000-70000 IU/week for 3-48 months.

The β cell autoantigen may be a β cell autoantigen as discussed below under the heading "Autoantigens".

The method may further comprise administration of a cyclooxygenase inhibitor, as discussed below under the heading "Cyclooxygenase inhibitors".

The method may further comprise administration of a CTLA4 compound, as discussed below under the heading "CTLA4 compounds".

The method may further comprise administration of a TNF α inhibitor, as discussed below under the heading "TNF α inhibitors".

The present invention provides a method for the prevention and/or treatment of an autoimmune disease in an individual in need thereof, the method comprising administering to said individual:

a) for specific antigen tolerization purposes, at least one autoantigen or fragments thereof; or nucleic acids, plasmids or vectors coding for such molecules related to at least one of the autoimmune and inflammatory diseases as listed above. In one embodiment, autoantigen is administered when serum vitamin D levels are between 50 and 150 nM/l, more preferably between 75 and 100 nM/l and most preferably between 100-150 nM/l; and b) for interfering with APCs ability to mature, administering to said individual at least one IL-10 inducing compound selected from the group consisting of vitamin D, vitamin D analogs, gamma-amino butyric acid, gamma-amino butyric acid analogs and tyrosine kinase inhibitors; as listed above. In one embodiment the IL-10 induction is enhanced or accomplished by use of UVB-light exposure; and c) for interfering with the immune system's ability to activate naïve TCs and BCs and recall responses from activated and memory lymphocytes, administering a compound such as a NSAID compound; a CTLA-4 compound; or a TNF α inhibitor; as listed above.

The present invention relates in some aspects to methods for prevention and/or treatment of autoimmune disease, such as type 1 diabetes (T1D) and autoimmune diabetes.

The invention discloses a method for treatment of autoimmune disease, such as T1D and autoimmune diabetes, the method comprising administering to a subject with said disease:

(a) a course of Vit D for enforcing the ability of antigen presenting dendritric cells to present antigen peptides to the immune system in a tolerizing manner;

b) an autoantigen, such as GAD65, formulated in a pharmaceutical carrier administered in an amount sufficient to restore or induce tolerance to the autoantigen; and optionally c) a therapeutic dose of an anti-inflammatory compound, for example a cyclooxygenase inhibitor such as ibuprofen, or a more pronounced cox-2 or cox-1 inhibitor.

The course of Vit D preferably starts 15 to 90 days prior to administration of autoantigen, or 7 to 90 days prior to administration of autoantigen, and is given in liquid or tablet form in doses corresponding to 7000 to 70000 iu per week for a period of 3 to 48 months.

The pretreatment with vitamin D aims to elevate the treated subject's serum levels of vitamin D to above about 50 nanomol/liter, or above 60, 75, or 100 nanomol/liter. The pretreatment may be dispensed with if the subject already has serum levels of vitamin D at these levels.

In another embodiment of the invention the serum concentration of Vit D can be enhanced by means of phototherapy. In this case subjects will be exposed to ultraviolet B radiation preferably between 10-120 minutes daily for 15 to 90 days prior to administration of autoantigen. The phototherapy should continue for a period of 3 to 48 months.

Preferred doses of the autoantigen is between two and four administrations, at least two weeks apart, more preferably one month apart, of each between 10 and 200 μg antigen if given by injection. If administered orally the preferred doses are between 500 mg and 5 g daily for a period of between three months and 48 months. Ibuprofen is preferably administered in daily doses of 100 to 800 mg for a period of 60 to 150 days during which period administration of autoantigen takes place.

The autoantigen can be administered by intralymphatic injection, injection directly into a lymph node, subcutaneous injection, intramuscular injection, intraperitoneal injection, intravenous injection, subcutaneous injection, intranasal, transmucosal or sublingual application; or orally, including administration as tablets, pellets, granules, capsules, lozenges, aqueous or oily solutions, suspensions, emulsions, sprays or as reconstituted dry powdered form with a liquid medium. The anti-inflammatory compound and the autoantigen can be administered in/with a pharmaceutically acceptable carrier, excipient or diluent.

In one embodiment of the invention and in the case of treatment or prevention of T1D, injection of autoantigens are made subcutaneous in unilateral or bilateral areas of the stomach to enable an increased traffic of APC cells presenting autoantigen peptides to pancreatic lymph nodes.

According to certain other embodiments, the at least one autoantigen is administered is subcutaneous, such as in the stomach close to the pancreatic draining lymph nodes. In some embodiments, the volume for subcutaneous injection of the antigens is between 0.2 and 2 ml, more preferred between 0.4 and 0.6 ml.

According to certain other embodiments, the at least one autoantigen is administered via intradermal injection.

According to certain embodiments, where the at least one antigen is administered via subcutaneous injection in a "vaccine-like" fashion, at least 4-250 μg, more preferably 10-100 μg most preferably 10-50 μg doses of each of the at least one antigen, is administered per treatment occasion.

According to certain embodiments, where the at least one antigen is administered via subcutaneous injection in an "allergy-like" fashion where various increasing dosage schedules of each used autoantigen may be used. Such a method may comprise administering the β cell autoantigen in increased doses over a period of weeks, months, or years.

In one embodiment of the composition containing the β cell autoantigen is administered 1-4 weeks apart, such as 2-4 weeks apart or 2 weeks apart, in an initial treatment period of 3 to 4 months, and optionally 2-3 months apart in a continued treatment period of 6-9 months.

In one embodiment, the amount of β cell autoantigen is increased from 1-5 μg per administration at the beginning of the treatment period to about 40-100 μg per administration in the final administrations.

In one embodiment, the method comprises subcutaneous injections of β cell autoantigen (e.g. GAD65) of increasing doses, starting at baseline (month 1) as follows: 0.4; 0.8; 2; 3.2; 4; 6.4; 8; 12; 16; 20; 24, 32, 40 μg, autoantigen weekly, where after 40 μg autoantigen will be administered from week 15 through 27 week at 2, 4 and 8 weeks interval. 40 μg autoantigen will thereafter be administered every 8-12 weeks for 1 year. Vitamin D may be administered as described above (from day 1)

A preferred dosing regimen includes increasing autoantigen doses of 1 μg, 5 μg, 20 μg, 50 μg, two injections of each dose 4 weeks apart which would be 28 weeks treatment GAD-alum. An alternatively preferred dosing schedule includes increasing doses such as 4 μg, 8 μg, 16 μg, 20 μg, 40 μg on days 0, 15, 30, 45, 60 and subsequently 40 μg on days 120, 180, 270.

In one embodiment of this invention administration of autoantigen is made directly into the lymph nodes or into the lymphatic system to allow resident APCs to present antigen peptides to the immune system. If administration of autoantigens is made directly into a lymph node or into the lymphatic system, the dose will preferably be between 1 and 15 μg per autoantigen, more preferred between 2 and 10 μg per autoantigen or 2 to 5 μg per autoantigen. Formulation in alum is preferred.

According to certain embodiments, the at least one autoantigen is administered intrainguinal, intralymph node or intralymphatic. In some embodiments, the volume for intra-inguinal injection of the antigens is between 0.05 and 0.2 ml, more preferred between 0.05 and 0.15 ml.

According to certain embodiments, where the at least one antigen is administered by intralymph-node or intralymphatic injection a preferred dosage is between 1-15 μg, more preferred between 2-10, and most preferred between 2-5 μg per injection and autoantigen used, such administrations taking place at least 2 times, more preferred at least 3 times and most preferred at least 4 times, at least 14 days apart, more preferably at least 30 days apart.

According to certain embodiments, where the at least one antigen is administered intravenously, at least 100-10000 μg of each antigen is administered per treatment occasion at least twice, at least one week apart.

According to certain embodiments, where the at least one antigen is administered orally, at least 0.5-5 μg of each antigen is administered per treatment occasion at least once every week.

According to certain embodiments, the at least one antigen is formulated separately or together with the other antigens as the case may be, in alum, saline or human serum albumin.

According to certain embodiments, the at least one pharmaceutical composition comprises at least two antigens on the same carrier particle. According to certain other embodiments, the at least one pharmaceutical composition comprises at least two antigens on different carrier particles. According to certain embodiments, the at least two antigens are administered separately and at different times and frequencies, regimens and formulations that are suitable for the specific antigens. More preferably the at least two antigens are formulated in the same pharmaceutical composition and therefore administered simultaneously.

In some embodiments the at least one antigen is formulated in an adjuvant such as alum. In more particular embodiments the at least one antigen is formulated in saline or human serum albumin.

According to certain embodiments, the at least one antigen and the at least one IL-10 inducing compound are administered simultaneously. According to certain embodiments, the at least one antigen and the at least one IL-10 inducing compound are administered separately.

According to certain embodiments, the at least one IL-10 inducing compound is administered simultaneously with the at least one antigen. According to certain embodiments, the administration of the at least one IL-10 inducing compound commences between 1-14 days prior to the first administration of the at least one antigen. According to certain embodiments, the administration of the at least one IL-10 inducing compound commences at least 2 preferably at least 10 weeks, prior to the first administration of the at least one autoantigen.

According to certain embodiments that include treatment periods with Vitamin D, between 500 and 10000 IU, more preferably between 1000 and 3000 IU of vitamin D, such as Vitamin D3, are administered per day.

According to certain embodiments that include pretreatment periods with vitamin D, between 7,000-100,000 IU of vitamin D, such as vitamin D3 are administered per week, prior to first administration of the at least one antigen, and as a maintenance dose of 500-2000 IU per day thereafter.

In some embodiments the treatment period of Vitamin D is between 60 and 420 days after 1$^{st}$ administration of antigen.

The compound that reduces the immune system's ability to activate naïve TCs and BCs and recall responses from activated and memory lymphocytes, such as a NSAID compound; a CTLA-4 compound; or a TNF-α inhibitor may be administered simultaneously or separately with the at least one antigen and/or the at least one IL-10 inducing compound.

In some embodiments, the compound that reduces the immune system's ability to activate naïve TCs and BCs and recall responses from activated and memory lymphocytes is a NSAID compound, such as a COX-inhibitor.

According to certain embodiments, the treatment period with NSAIDs starts at least 2 weeks prior to first administration of the at least one antigen.

According to certain embodiments, when the COX inhibitor is ibuprofen, at least one 400 to 1000 mg doses are administered per day during the NSAID treatment period.

The NSAID treatment period is at least between 4 and 14 weeks, more preferred between 4 and 8 weeks In the present methods, the anti-inflammatory compound should be administered orally or by injection.

In some embodiments, the compound that reduces the immune system's ability to activate naïve TCs and BCs and recall responses from activated and memory lymphocytes is a TNF-α inhibitor.

Blocking TNF α reduces the activation state of the immune response and decreases the activity of DCs and other immunocytes. Further, because TNF α disrupts FSC and GC architecture in lymphoid tissue and impairs B cell functions, the activation of antigen-specific effector T cells and autoantibody production is reduced. Recent diabetes preclinical data show that β cell antigen delivered by quiescent DCs can induce peripheral T cell unresponsiveness, down-modulate ongoing β cell destruction and arrest β cell destruction. Therefore, under a combined autoantigen—TNF α inhibitor therapy autoantibody levels and effector T cell activity and numbers will be relatively reduced while the number of autoantigen-specific Tregs number and function will be at least maintained. It takes months to modify these immunologic processes and document these effects, but during this time, due to its acute β-cell-protective and metabolic effects, TNF α inhibition will also preserve β cells directly. Because GAD65 is known to be one of the primary autoantigens in T1DM, this approach produces a deviation of the diabetes autoimmune response towards a regulatory phenotype of sufficient critical mass to lead to a significant and prolonged effect on β cell preservation.

Thus, in one aspect of the present invention, a TNF α inhibitor not limited to for example infliximab, adalimumab, golimumab, and etanercept, is used as an anti-inflammatory compound. A preferred dose when etanercept is used is between 0.2 and 1 mg/kg SQ, once or twice per week for a period of between 2 to 9 months.

According to certain embodiments, when the TNF-α inhibitor is etanercept, the FDA-approved dosage of 5 mg/kg at weeks 0, 2, and 6 is preferred. In another embodiment the dose is the same as used in the phase I TNF-α inhibitor monotherapy trial (0.4 mg/kg (max 25 mg) SQ twice weekly×26 weeks). In most preferred another embodiment only two doses are used, max 25 mg/dose in combination treatment regimen including vitamin D and autoantigens.

According to certain embodiments, the TNF-α inhibitor is administered prior to the first administration of the at least one antigen.

In some embodiments, the compound that reduces the immune system's ability to activate naïve TCs and BCs and recall responses from activated and memory lymphocytes is a CTLA-4 compound, such as abatacept. According to particular embodiments, when the compound is abatacept doses of at least 2-20 mg/kg abatacept, is administered per treatment occasion, starting within +/−7 days around the time of first administration of the at least one antigen.

According to certain embodiments, the CTLA-4 compound is administered simultaneously with the first administration of the at least one antigen.

According to certain embodiments, administration of the at least one antigen and the compound that reduces the immune system's ability to activate naïve TCs and BCs and recall responses from activated and memory lymphocytes, is repeated on day 14, 28 and 45+/−one week as the case may be to ensure blockage of CD28 on TCs, and where day one marks the first administration of the at least one IL-10 inducing compound.

In one aspect, the invention provides a method to treat one or more symptoms associated with T1D. Symptoms associated with T1D include, but are not limited to, reduced insulin production, reduced insulin sensitivity, high blood glucose levels, destruction of insulin producing cells, and abnormal C peptide levels.

The methods of the invention may be directed towards the treatment and prevention of not only T1D but generally for autoimmune diseases and disorders. For example, subjects suffering from Grave's disease, Hashimoto's thyroiditis, hypoglyceimia, multiple sclerosis, mixed essential cryoglobulinemia, systemic lupus erthematosus, rheumatoid arthritis (RA), coeliac disease, T1D, or any combination thereof. In these cases, for the disease relevant autoantigens are to be included as autoantigens in the treatment methods. In one aspect of the invention, the subjects suffer from autoimmune responses that involve T cells or B cells that have an antigenic specificity, or T cell receptor (TCR) and/or B cells that have T cell receptor (TCR) or B cell receptor (BCR) antigen specificity for an autoantigen.

According to certain embodiments, the individual to be treated according to the present invention is a mammal. According to particular embodiments, the individual to be treated according to the present invention is a human. According to certain embodiments, the individual to be treated according to the present invention is an infant. According to particular embodiments, the individual to be treated according to the present invention is an adolescent human. According to particular embodiments, the individual to be treated according to the present invention is an adult human.

In some embodiments the human treated subject is above 4 years of age

In other embodiments the human treated subject is 8 years or above.

In other embodiments the human treated subject is 10 years or above.

In some embodiments the human treated subject is 18 years or below.

In some embodiments the human treated subject is 4-10, or 4-18, or 8-18, or 10-18 years of age.

In other embodiments the human treated subject is 18 years or above.

In some embodiments the human treated subject is 18-30 years of age.

Compositions

The present invention also discloses a composition comprising a plurality of particles, each having immobilised on its surface at least one first and at least one second antigen, wherein the first antigen is a β cell autoantigen, and the second antigen is either a tolerogen or a β cell autoantigen, the composition further optionally comprising pharmaceutically acceptable adjuvants, excipients, solvents, and/or buffers.

According to certain embodiments, the at least one autoantigen is formulated in an adjuvant. According to particular embodiments, the adjuvant is alum. In other particular embodiments the at least one antigen is formulated in saline or human serum albumin. In more particular embodiments the autoantigen may be administered as plasmids or encoded by a viral vector such as adeno-associated virus vectors or herpes simplex virus vectors.

According to certain embodiments, the at least one autoantigen is as discussed below.

The compositions according to the invention may comprise more than one autoantigen. Thus, according to certain embodiments, the composition comprises at least two autoantigens. According to certain other embodiments, the composition comprises at least three autoantigens. According to certain other embodiments, the composition comprises at least four autoantigens.

Therefore, according to particular embodiments, the composition comprises at least GAD, such as GAD-65, and insulin. According to other particular embodiments, the composition comprises at least insulinoma antigen-2 and insulin. According to other particular embodiments, the composition comprises at least ZnT8 and insulin. According to other particular embodiments, the composition comprises at least IGRP and insulin. According to other particular embodiments, the composition comprises at least chromogranin A and insulin.

According to other particular embodiments, the composition comprises at least GAD, such as GAD-65, and B chain insulin. According to other particular embodiments, the composition comprises at least insulinoma antigen-2 and B chain insulin. According to other particular embodiments, the composition comprises at least ZnT8 and B chain insulin. According to other particular embodiments, the composition comprises at least IGRP and B chain insulin. According to other particular embodiments, the composition comprises at least chromogranin A and B chain insulin.

According to other particular embodiments, the composition comprises at least GAD, such as GAD-65, and proinsulin. According to other particular embodiments, the composition comprises at least insulinoma antigen-2 and proinsulin. According to other particular embodiments, the composition comprises at least ZnT8 and proinsulin. According to other particular embodiments, the composition comprises at least IGRP and proinsulin. According to other particular embodiments, the composition comprises at least chromogranin A and proinsulin.

According to other particular embodiments, the composition comprises at least insulin and B chain insulin. According to other particular embodiments, the composition comprises at least insulin and proinsulin. According to other particular embodiments, the composition comprises at least B chain insulin and proinsulin.

According to particular embodiments, the composition comprises at least GAD, such as GAD-65, insulin and B chain insulin. According to other particular embodiment, the composition comprises at least GAD, such as GAD-65, insulin and proinsulin. According to yet other particular embodiments, the composition comprises at least GAD, such as GAD-65, B chain insulin and proinsulin. According to yet other particular embodiments, the composition comprises at least insulin, B chain insulin and proinsulin.

According to other particular embodiments, the composition comprises GAD, such as GAD-65, insulin, B chain insulin and B chain insulin.

According to certain embodiments, the at least one autoantigen, such as the at least two autoantigens or at least three autoantigens, is formulated in an adjuvant.

The autoantigens may be formulated in adjuvants such as aluminium hydroxid, MAS-1, human serum albumin, lipid-emulsions.

According to particular embodiments, the adjuvant is alum.

In one embodiment, the invention relates to a composition comprising i) at least one β cell autoantigen, and at least one of
iia) an IL-10 inducing compound selected from the group consisting of vitamin D, vitamin D analogs, tyrosine kinase inhibitors, gamma-amino butyric acid, and gamma-amino butyric acid analogs; and
iib) a compound that reduces the dendritic cells' ability to activate naïve CD4+ T cells, such as a cyclooxygenase inhibitor, a CTLA-4 compound or a TNF α inhibitor; and optionally pharmaceutically acceptable adjuvants, excipients, solvents, and/or buffers.

The present invention also provides a composition (e.g. a pharmaceutical composition) comprising i) at least one autoantigen and ii) at least one IL-10 inducing compound.

More particularly, the present invention provides a composition (e.g. a pharmaceutical composition) comprising i) at least one autoantigen selected from the group consisting of insulin, B chain insulin, proinsulin, and β cell autoantigens, and ii) at least one IL-10 inducing compound selecting from the group consisting of vitamin D, vitamin D analogs and tyrosine kinase inhibitors.

The composition according to the invention may comprise more than one IL-10 inducing compound. Thus, according to certain embodiments, the composition comprises at least two IL-10 inducing compounds. According to certain other embodiments, the composition comprises at least three IL-10 inducing compounds. According to certain other embodiments, the composition comprises at least four IL-10 inducing compounds.

Therefore, according to particular embodiments, the composition comprises at least vitamin D and a tyrosine kinase inhibitor. According to other particular embodiments, the composition comprises at least a vitamin D analog and a tyrosine kinase inhibitor.

According to more particular embodiments, the composition comprises at least Vitamin D and dasatinib. According to other more particular embodiments, the composition comprises at least Vitamin D and bosutinib. According to other more particular embodiments, the composition comprises at least Vitamin D and saracatinib. According to other more particular embodiments, the composition comprises at least vitamin D and imatinib. According to other more particular embodiments, the composition comprises at least vitamin D and sunitinib.

According to more particular embodiments, the composition comprises at least a vitamin D analog and dasatinib. According to other more particular embodiments, the composition comprises at least a vitamin D analog and bosutinib. According to other more particular embodiments, the composition comprises at least a vitamin D analog and saracatinib. According to other more particular embodiments, the composition comprises at least a vitamin D analog and imatinib. According to other more particular embodiments, the composition comprises at least a vitamin D analog and sunitinib.

According to certain embodiments, the composition further comprises iii) a compound that reduces the dendritic cells' ability to activate naïve CD4+ T cells, such as a cyclooxygenase inhibitor, a CTLA-4 compound or a TNF α inhibitor.

According to particular embodiments, such compound is a cyclooxygenase inhibitor, such as a non-steroidal anti-inflammatory drug (NSAID). According to more particular embodiments, the NSAID is selected from the group consisting of ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, aspirin (acetylsalicylic acid), diflunisal (Dolobid®), salicylic acid, salsalate (Disalcid®), piroxicam, meloxicam, tenoxicam, droxicam, lornoxicam, isoxicam, mefenamic acid, meclofenamic acid, flufenamic acid, tolfenamic acid, celecoxibcelecoxib, rofecoxib, valdecoxib, parecoxib, lumiracoxib, etoricoxib, and nimesulide.

In one embodiment of the present invention, the at least one composition including the protein/peptide antigen, or combination of protein/peptide antigens, will be formulated by mixing the individual GMP produced protein/peptide solutions together in a formulation buffer. The combined protein solution will then be sterile filtered into a closed formulation vessel with constant mixing, after which a sterile solution of adjuvant will be added to the formulation vessel. The protein containing particles will then be aseptically added to sterile and depyrogenated glass injection vials or prefilled syringes and sealed. Protein adsorbed articles can be drawn aseptically from each vial for injection into patient or subject tissue.

The proportions of combined proteins in the formulation can vary although most preferred is equal proportions by gram weight. If used, the proportion of influencing antigen should be at least equal to the combined mass of the other antigen proteins or peptides. The proportion of influencing antigen can be greater than the combined mass of the other antigens. The formulation buffer can be an isotonic phosphate buffered mannitol buffer. The adjuvant can be aluminum hydroxide (alum), a liposome, poly(lactide-co-glycolide) microparticles, or saline.

The medicaments, pharmaceutical compositions or therapeutic combinations according to the present invention may be in any form suitable for the application to humans and/or animals, preferably humans including infants, children and adults and can be produced by standard procedures known to those skilled in the art. The medicament, (pharmaceutical) composition or therapeutic combination can be produced by standard procedures known to those skilled in the art, e.g. from the table of contents of "Pharmaceutics: The Science of Dosage Forms", Second Edition, Aulton, M. E. (ED. Churchill Livingstone, Edinburgh (2002); "Encyclopedia of Pharmaceutical Technology", Second Edition, Swarbrick, J. and Boylan 15 J. C. (Eds.), Marcel Dekker, Inc. New York (2002); "Modern Pharmaceutics", Fourth Edition, Banker G. S. and Rhodes C. T. (Eds.) Marcel Dekker, Inc. New York 2002 y "The Theory and Practice of Industrial Pharmacy", Lachman L., Lieberman H. And Kanig J. (Eds.), Lea & Febiger, Philadelphia (1986). The respective descriptions are hereby incorporated by reference and form part of the disclosure. The terms "medicament", "pharmaceutical composition" and "pharmaceutical formulations" may be used interchangeably.

The medicament, pharmaceutical composition or therapeutic combination according to the present invention may further comprise one or more pharmaceutically acceptable excipients. Carriers, diluents and excipients which are suitable for the preparation of a medicament, pharmaceutical composition or therapeutic combination according to the present invention are well known to those skilled in the art, e.g. from the "Handbook of Pharmaceutical Excipients" Sixth Edition, Raymond C. Rowe, Paul J. Sheskey and Marian E Quinn (Eds.), American Pharmaceutical Association (July 2009), which is hereby incorporated by reference and forms part of the disclosure.

Autoantigens

Autoantigens suitable for use in the methods, compositions, and kits according to the present invention are β cell autoantigens.

These include: glutamic acid decarboxylase (GAD65 or GAD 67 or GAD32) (Baekkeskov et al., Nature (1990) 347: 151)); Insulin (Palmer et al., Science (1983) 222: 1337); including the B9-23 peptide comprising amino acids 9-23 of the insulin B chain (Daniel et al., Proc. Natl. Acad. Sci. USA (1995) 93: 956-960; Wong et al., Nat. Med. (1999) 5: 1026-1031) Proinsulin; including the B24-C36 peptide comprising amino acids 24-36 spanning the proinsulin B-chain C peptide junction (Chen et al., J. Immunol. (2001) 167: 4926-4935; Rudy et al., Mol. Med., (1995) 1: 625-633); HSP60 (heat shock protein 60, Raz et al., Lancet (2001), 358:1749-53); ICA512/IA-2 (islet cell antigen 512; Rabin et al., J. Immunol. (1994) 152: 3183), insulinoma antigen-2, ZnT8, islet-specific glucose-6-phosphate catalytic subunit-related protein (IGRP), chromogranin A, B chain insulin, preproinsulin, proinsulin II, a proinsulin peptide without a cytotoxic T-lymphocyte epitope, insulin C13-A5 peptide, islet cell antigen p69, or any peptide, derivative including citrullinated forms iDS, and corresponding nucleotides of the above.

For an alignment of insulin sequences between species, see Table I in Homann et al., J. Immunol. (1999) 63: 1833-1838.

According to particular embodiments, the β cell autoantigen is GAD, such as GAD-65 or GAD-67, including fragments thereof, derivatives thereof, or a nucleic acid coding therefor.

According to more particular embodiments, the β cell autoantigen is GAD-65, a fragment thereof, derivative thereof, or a nucleic acid coding therefor. According to more particular embodiments, the β cell autoantigen is GAD-65. According to other particular embodiments, the β cell autoantigen is a fragment derived from GAD-65 (i.e. a GAD65 fragment).

According to other particular embodiments, the β cell autoantigen is insulinoma antigen-2.

According to other particular embodiments, the β cell autoantigen is ZnT8.

According to other particular embodiments, the β cell autoantigen is islet-specific glucose-6-phosphate catalytic subunit-related protein (IGRP).

According to other particular embodiments, the β cell autoantigen is chromogranin A.

According to certain other embodiments, the β cell autoantigen is insulin.

According to certain other embodiments, the β cell autoantigen is B chain insulin.

According to certain other embodiments, the β cell autoantigen is proinsulin.

According to certain other embodiments, the β cell autoantigen is preproinsulin.

In some aspects of the present invention, a tolerogen is administered to the treated subject. A tolerogen is an antigen that induces a state of specific immunological unresponsiveness to subsequent challenging doses of the antigen. Suitable tolerogens for use in the present invention are native endogenous human proteins and other molecules that are abundantly available and exposed to the immune system and generally recognized as self. Examples of tolerogens include IL-10, human serum albumin or hemoglobin, or gamma-amino butyric acid.

The autoantigens or tolerogens for use in the invention may be administered as full-length proteins, or they may alternatively be administered as fragments or variants of such full-length proteins with the proviso that the fragments or variants of autoantigens have at least one epitope conserved relative to the original autoantigen and are effective in the methods according to the present invention.

A fragment of a protein autoantigen or tolerogen has the same amino acid sequence as the original autoantigen or tolerogen, but lacks at least one N-terminal or C-terminal amino acid residue. A fragment of an autoantigen should comprise at least one relevant epitope of the original autoantigen. Autoantigen and tolerogen fragments preferably have a length of at least 8 amino acids, such as at least 10, 15, 20, 30, 40, 50, 60, 70, 80, 90 or 100 amino acids.

A variant of a protein autoantigen or tolerogen may have an amino acid sequence that is less than 100% identical to the original autoantigen or tolerogen, such as 99%, 95%, 90%, 85%, 80%, 70%, 60% or 50% identical (as compared by a protein sequence alignment tool, e.g. Clustal Omega available from the European Bioinformatics Institute, Hinxton, GB), while, for autoantigens, at the same time having at least one relevant epitope conserved relative to the original autoantigen. Variants may also have shorter (i.e. be a fragment) or longer amino acid sequences as compared to the original antigen or tolerogen.

In the invention, the administration of an autoantigen or tolerogen can involve an autoantigen or tolerogen that comprises a protein or a peptide fragment of the original protein. It may also involve the administration of a variant of the autoantigen or tolerogen.

Further, the protein or peptide can be introduced into a subject as a protein or peptide in a pharmaceutically acceptable carrier or the protein or peptide can be encoded by an expression vector, where the expression vector is introduced (for example, see the Examples where the self-antigen is expressed in a subject by a pCMV-expression vector). Such an expression vector may be a nucleic acid, such as DNA or RNA, and may be delivered by needle injection, gene guns, jet injection or with the aid of cytofectin as known in the art. The nucleic acid may be formulated in saline, on gold beads, in liposomes or in lipid formulations. For further description regarding the administration of self-antigens via their expression vectors, (and for specific antigens that can be administered) see U.S. Patent Publication US 2002/0107210, which is hereby incorporated by reference.

IL-10 Inducing Compounds

In some aspects, the methods, compositions and kits of the present invention use IL-10 inducing compounds.

According to certain embodiments, the at least one IL-10 inducing compound is vitamin D, such as 1,25-dihydroxyvitamin D.

According to certain other embodiments, the at least one IL-10 inducing compound is a vitamin D analog, such as TX527.

According to certain other embodiments, the at least one IL-10 inducing compound include enhancement of serum vitamin D by means of UVB radiation.

According to certain other embodiments, the at least one IL-10 inducing compound is a tyrosine kinase inhibitor, such as dasatinib, bosutinib, saracatinib, imatinib, sunitinib, or combinations thereof.

According to particular embodiments, the tyrosine kinase inhibitor is dasatinib.

According to other particular embodiments, the tyrosine kinase inhibitor is bosutinib.

According to other particular embodiments, the tyrosine kinase inhibitor is saracatinib.

According to other particular embodiments, the tyrosine kinase inhibitor is imatinib.

According to other particular embodiments, the tyrosine kinase inhibitor is sunitinib.

According to other particular embodiments, the tyrosine kinase inhibitor is a combination of at least two of dasatinib, bosutinib, saracatinib, imatinib and sunitinib. For example, the tyrosine kinase inhibitor may be a combination of dasatinib and bosutinib. According to other more particular embodiments, the tyrosine kinase inhibitor is a combination of dasatinib and saracatinib. According to other more particular embodiments, the tyrosine kinase inhibitor is a combination of dasatinib and imatinib. According to other more particular embodiments, the tyrosine kinase inhibitor is a combination of dasatinib and sunitinib. According to other more particular embodiments, the tyrosine kinase inhibitor is a combination of bosutinib and saracatinib. According to other more particular embodiments, the tyrosine kinase inhibitor is a combination of bosutinib and imatinib. According to other more particular embodiments, the tyrosine kinase inhibitor is a combination of bosutinib and sunitinib. According to other more particular embodiments, the tyrosine kinase inhibitor is a combination of imatinib and sunitinib. According to other more particular embodiments, the tyrosine kinase inhibitor is a combination of dasatinib, bosutinib and saracatinib.

The composition according to the invention may comprise more than one IL-10 inducing compound. Thus, according to certain embodiments, the composition comprises at least two IL-10 inducing compounds. According to certain other embodiments, the composition comprises at least three IL-10 inducing compounds. According to certain other embodiments, the composition comprises at least four IL-10 inducing compounds.

Cyclooxygenase Inhibitors

In some aspects, the methods, compositions and kits of the present invention use one or more cyclooxygenase inhibitors.

These cyclooxygenase inhibitors may be non-steroidal anti-inflammatory drugs (NSAID). According to more particular embodiments, the NSAID is selected from the group consisting of ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, aspirin (acetylsalicylic acid), diflunisal (Dolobid®), salicylic acid, salsalate (Disalcid®), piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, and nimesulide.

According to certain embodiments, the cyclooxygenase inhibitor is a propionic acid derivative, such as ibuprofen, dexibuprofen, naproxen, fenoprofen, ketoprofen, dexketoprofen, flurbiprofen, oxaprozin or loxoprofen.

According to certain embodiments, the cyclooxygenase inhibitor is an acetic acid derivative, such as indomethacin, tolmetin, sulindac, etodolac, ketorolac, diclofenac, aceclofenac or mabumetone.

According to certain embodiments, the cyclooxygenase inhibitor is a salicylate, such as aspirin (acetylsalicylic acid), diflunisal (Dolobid®), salicylic acid or salsalate.

According to certain embodiments, the cyclooxygenase inhibitor is an enolic acid (oxicam) derivative, such as piroxicam, meloxicam, tenoxicam, droxicam, lornoxicam or isoxicam.

According to certain embodiments, the cyclooxygenase inhibitor is an anthranilic acid derivative, such as mefenamic acid, meclofenamic acid, flufenamic acid or tolfenamic acid.

According to certain embodiments, the cyclooxygenase inhibitor is selective COX-2 inhibitor, such as celecoxib, rofecoxib, valdecoxib, parecoxib, lumiracoxib or etoricoxib.

According to more particular embodiments, the cyclooxygenase inhibitor is ibuprofen.

According to more particular embodiments, the cyclooxygenase inhibitor is dexibuprofen.

According to more particular embodiments, the cyclooxygenase inhibitor is naproxen.

According to more particular embodiments, the cyclooxygenase inhibitor is fenoprofen According to more particular embodiments, the cyclooxygenase inhibitor is ketoprofen.

According to more particular embodiments, the cyclooxygenase inhibitor is dexketoprofen.

According to more particular embodiments, the cyclooxygenase inhibitor is flurbiprofen.

According to more particular embodiments, the cyclooxygenase inhibitor is oxaprozin.

According to more particular embodiments, the cyclooxygenase inhibitor is loxoprofen.

According to more particular embodiments, the cyclooxygenase inhibitor is indomethacin.

Ibuprofen mainly blocks cox-2 but to some extent also cox-1. Ibuprofen has a somewhat broader effect on the immune system than a narrow IL-1 blocker and a quite pronounced anti-inflammatory effect without serious risks. Use of ibuprofen dampens β cell inflammation and enables the Vit D enforced DCs to induce tolerance to peptides from autoantigens presented to T cells, thereby protecting the β cells in the subject.

CTLA4 Compounds

In some aspects, the methods, compositions and kits of the present invention use a CTLA-4 compound, such as a cytotoxic T-lymphocyte—associated antigen 4 immunoglobulin.

According to more particular embodiments, the CTLA-4 compound is abatacept.

Abatacept (an Fc modified CTLA4 immunoglobulin) is a T cell depleting, immunomodulating, fusion protein consisting of the extracellular portion of human CTLA4 and the heavy chain of human IgG1. It blocks the costimulatory signal involved in activation of naïve T cells. Its ligation with CD80/86 on APCs may also interfere with and reduce CD80/86 induced IL-6, which may downregulate inflammatory cytokines such as IL-1β, IFN gamma, and IL-17. Further abatacept ligation with CD80/86 may induce indoleamine dioxygenase (IDO) in APCs, which may in turn may induce anergy in T cells, as well as downregulate paracrine activation of naïve T cells by activated T cells. CD80/86 expressed on B cells may yet be a further path where abatacept may carry out an immunomodulating function.

TNF α Inhibitors

In some aspects, the methods, compositions and kits of the present invention use a TNF α inhibitor, such as adalimumab, certolizumab, etanercept, golimumab or infliximab. According to more particular embodiments, the TNF α inhibitor is adalimumab. According to other more particular embodiments, the TNF α inhibitor is certolizumab. According to other more particular embodiments, the TNF α inhibitor is etanercept. According to other more particular embodiments, the TNF α inhibitor is golimumab. According to other more particular embodiments, the TNF α inhibitor is infliximab.

Kits

The invention also provides kits relating to the methods of the invention. For example, in one aspect, a kit can comprise: (a) an anti-inflammatory compound; (b) an autoantigen; and (c) vitamin D and optionally d) instructions for the regimen of the invention.

The present invention also discloses a pharmaceutical kit comprising
    i) a composition comprising a β cell autoantigen, and at least one of
    iia) a composition comprising an IL-10 inducing compound selected from the group consisting of vitamin D, vitamin D analogs, tyrosine kinase inhibitors, gamma-amino butyric acid, and gamma-amino butyric acid analogs; and
    iib) a composition comprising a compound that reduces the dendritic cells' ability to activate naïve CD4$^+$ T cells, such as a cyclooxygenase inhibitor, a CTLA-4 compound or a TNF α inhibitor.

The present invention also discloses a pharmaceutical kit comprising
    i) a composition comprising a β cell autoantigen, and at least one of
    iia) a composition comprising an IL-10 inducing compound selected from the group consisting of vitamin D, vitamin D analogs, tyrosine kinase inhibitors, gamma-amino butyric acid, and gamma-amino butyric acid analogs; and
    iib) a composition comprising a compound that reduces the dendritic cells' ability to activate naïve CD4$^+$ T cells, such as a cyclooxygenase inhibitor, a CTLA-4 compound or a TNF α inhibitor.

The present invention also discloses the use of Compositions comprising at least two of:
    i) at least one antigen or fragments thereof; or nucleic acids coding for such molecules related to at least one of the autoimmune and inflammatory diseases in the group as listed herein; and
    ii) at least one IL-10 inducing compound selected from the group: vitamin D such as 1,25-Dihydroxyvitamin D. According to certain other embodiments, the at least one IL-10 inducing compound is a vitamin D analog, such as TX527. According to certain other embodiments, the at least one IL-10 inducing compound is a tyrosine kinase inhibitor, such as dasatinib, bosutinib, saracatinib, imatinib, sunitinib, or combinations thereof; and
    iii) at least one compound that reduces the immune system's ability to activate naïve TCs and BCs and to recall responses from activated and memory lymphocytes, such as a COX-inhibitor; a CTLA-4 compound; or a TNF α inhibitor; as listed herein);
in the manufacture of a kit including at least two pharmaceutical compositions (i.e. medicaments).

One of the at least two pharmaceutical compositions can comprise the at least one antigen formulated in alum, saline or human serum albumin as an injectable in a prefilled vial or syringe, and another of the at least two pharmaceutical compositions may comprise the IL-10 inducing compound in the form of tablets for oral administration.

Some embodiments of the present invention provide a kit including at least two pharmaceutical compositions, comprising i) at least one antigen selected from the group listed herein and ii) at least one compound that reduces the dendritic cells' ability to activate naïve lymphocytes or recall activated or memory lymphocytes selected from the group: COX-inhibitors; CTLA-4 compounds; and TNF α inhibitors. As an example, one of the at least two pharmaceutical compositions can comprise the at least one antigen formulated in alum, saline or human serum albumin as injectable in a prefilled vial or syringe, and another of the at least two pharmaceutical compositions may comprise one compound selected from the group COX-inhibitors; a CTLA-4 compound; and TNF(inhibitors.

Some embodiments of the present invention provide a kit including at least three pharmaceutical compositions, comprising i) at least one antigen selected from the group listed herein; ii) at least one IL-10 inducing compound selected from the group consisting of vitamin D, vitamin D analogs and tyrosine kinase inhibitors. and iii) at least one compound that reduces the dendritic cells' ability to activate naïve lymphocytes or recall activated or memory lymphocytes selected from the group: COX-inhibitors; CTLA-4 compounds; and TNF α inhibitors. As an example, one of the at least three pharmaceutical compositions can comprise the at least one antigen formulated in alum, saline or human serum albumin as an injectable in a prefilled vial or syringe, and another of the at least three pharmaceutical compositions may comprise at least one IL-10 inducing compound selected from the group consisting of vitamin D, vitamin D analogs, gamma-amino butyric acid, gamma-amino butyric acid analogs, and tyrosine kinase inhibitors, and a third of the at least three pharmaceutical compositions may comprise one compound selected from the group COX-inhibitors; a CTLA-4 compound; and TNF-α inhibitors.

Medical Use

The composition of the present invention may be used in therapy, in particular in the prevention and/or treatment of an autoimmune disease. Accordingly, the composition of the present invention may be a pharmaceutical composition.

According to certain embodiments, the composition is for use as medicament, such as for use in the prevention and/or treatment of an autoimmune disease.

According to particular embodiments, the composition is for use in the prevention and/or treatment of type 1 diabetes, such as type 1.

According to other particular embodiments, the composition is for use in the prevention and/or treatment of autoimmune diabetes.

According to other particular embodiments, the composition is for use in the prevention and/or treatment of latent autoimmune diabetes.

According to yet other particular embodiments, the composition is for use in the prevention and/or treatment of recurrence of autoimmune diabetes, such as recurrence of autoimmune diabetes in an individual (e.g. a human) with autoimmune diabetes that has been subject to islet cell transplantation or other cell therapies including stem cell therapy.

The present invention provides in a further aspect an autoantigen in combination with at least one IL-10 inducing compound for use in the prevention and/or treatment of an autoimmune disease.

More particularly, the present invention provides an autoantigen selected from the group consisting of insulin, B chain insulin, proinsulin, and β cell autoantigens, in combination with at least one IL-10 inducing compound, such as at least one IL-10 inducing compound selecting from the group consisting of vitamin D, vitamin D analogs and tyrosine kinase inhibitors, for use in the prevention and/or treatment of an autoimmune disease.

According to certain embodiments, the autoantigen is a β cell autoantigen, such as, glutamic acid decarboxylase (GAD), insulinoma antigen-2, ZnT8, islet-specific glucose-6-phosphate catalytic subunit-related protein (IGRP) or chromogranin A.

According to particular embodiments, the β cell autoantigen is GAD, such as GAD-65 including fragments thereof, derivatives thereof, or a nucleotide coding therefor.

According to more particular embodiments, the β cell autoantigen is GAD-65, a fragment thereof, derivative thereof, or a nucleotide coding therefor. According to more particular embodiments, the β cell autoantigen is GAD-65. According to other particular embodiments, the β cell autoantigen is a fragment derived from GAD-65 (i.e. a GAD65 fragment.

According to other particular embodiments, the β cell autoantigen is insulinoma antigen-2.

According to other particular embodiments, the β cell autoantigen is ZnT8.

According to other particular embodiments, the β cell autoantigen is islet-specific glucose-6-phosphate catalytic subunit-related protein (IGRP).

According to other particular embodiments, the β cell autoantigen is chromogranin A.

According to certain embodiments, the autoantigen is insulin.

According to certain other embodiments, the autoantigen is B chain insulin.

According to certain other embodiments, the autoantigen is proinsulin.

According to certain embodiments, the autoantigen is formulated in an adjuvant.

According to particular embodiments, the adjuvant is alum.

According to certain embodiments, the at least one IL-10 inducing compound is vitamin D, such as 1,25-dihydroxyvitamin D.

According to certain other embodiments, the at least one IL-10 inducing compound is a vitamin D analog, such as TX527.

According to certain other embodiments, the at least one IL-10 inducing compound is a tyrosine kinase inhibitor, such as dasatinib, bosutinib, saracatinib, imatinib, sunitinib, or combinations thereof.

According to particular embodiments, the tyrosine kinase inhibitor is dasatinib.

According to other particular embodiments, the tyrosine kinase inhibitor is bosutinib.

According to other particular embodiments, the tyrosine kinase inhibitor is saracatinib.

According to other particular embodiments, the tyrosine kinase inhibitor is imatinib.

According to other particular embodiments, the tyrosine kinase inhibitor is sunitinib.

According to other particular embodiments, the tyrosine kinase inhibitor is a combination of at least two of dasatinib, bosutinib, saracatinib, imatinib and sunitinib. For example, the tyrosine kinase inhibitor may be a combination of dasatinib and bosutinib. According to other more particular embodiments, the tyrosine kinase inhibitor is a combination of dasatinib and saracatinib. According to other more particular embodiments, the tyrosine kinase inhibitor is a combination of dasatinib and imatinib. According to other more particular embodiments, the tyrosine kinase inhibitor is a combination of dasatinib and sunitinib. According to other more particular embodiments, the tyrosine kinase inhibitor is a combination of bosutinib and saracatinib. According to other more particular embodiments, the tyrosine kinase inhibitor is a combination of bosutinib and imatinib.

According to other more particular embodiments, the tyrosine kinase inhibitor is a combination of bosutinib and sunitinib. According to other more particular embodiments, the tyrosine kinase inhibitor is a combination of imatinib and sunitinib According to other more particular embodiments, the tyrosine kinase inhibitor is a combination of dasatinib, bosutinib and saracatinib.

According to certain embodiments, the autoantigen is further used in combination with a compound that reduces the dendritic cells' ability to activate naïve CD4⁺ T cells, such as a cyclooxygenase inhibitor, a CTLA-4 compound or a TNF α inhibitor.

According to particular embodiments, such compound is a cyclooxygenase inhibitor, such as a non-steroidal anti-inflammatory drug (NSAID). According to more particular embodiments, the NSAID is selected from the group consisting of ibuprofen, dexibuprofen, daproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, aspirin (acetylsalicylic acid), diflunisal (Dolobid®), salicylic acid, salsalate (Disalcid®), piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, and nimesulide.

According to certain embodiments, the cyclooxygenase inhibitor is a propionic acid derivative, such as ibuprofen, dexibuprofen, naproxen, fenoprofen, ketoprofen, dexketoprofen, flurbiprofen, oxaprozin or loxoprofen.

According to certain embodiments, the cyclooxygenase inhibitor is an acetic acid derivative, such as indomethacin, tolmetin, sulindac, etodolac, ketorolac, diclofenac, aceclofenac or nabumetone.

According to certain embodiments, the cyclooxygenase inhibitor is a salicylate, such as aspirin (acetylsalicylic acid), diflunisal (Dolobid®), salicylic acid or salsalate.

According to certain embodiments, the cyclooxygenase inhibitor is an enolic acid (oxicam) derivative, such as piroxicam, meloxicam, tenoxicam, droxicam, lornoxicam or isoxicam.

According to certain embodiments, the cyclooxygenase inhibitor is an anthranilic acid derivative, such as mefenamic acid, meclofenamic acid, flufenamic acid or tolfenamic acid.

According to certain embodiments, the cyclooxygenase inhibitor is selective COX-2 inhibitor, such as celecoxib, rofecoxib, valdecoxib, parecoxib, lumiracoxib or etoricoxib.

According to more particular embodiments, the cyclooxygenase inhibitor is ibuprofen.

According to more particular embodiments, the cyclooxygenase inhibitor is dexibuprofen.

According to more particular embodiments, the cyclooxygenase inhibitor is Naproxen.

According to more particular embodiments, the cyclooxygenase inhibitor is fenoprofen According to more particular embodiments, the cyclooxygenase inhibitor is ketoprofen.

According to more particular embodiments, the cyclooxygenase inhibitor is dexketoprofen.

According to more particular embodiments, the cyclooxygenase inhibitor is flurbiprofen.

According to more particular embodiments, the cyclooxygenase inhibitor is oxaprozin.

According to more particular embodiments, the cyclooxygenase inhibitor is loxoprofen.

According to more particular embodiments, the cyclooxygenase inhibitor is Indomethacin.

According to other particular embodiments, such compound is a CTLA-4 compound, such as a cytotoxic T-lymphocyte-associated antigen 4 immunoglobulin.

According to more particular embodiments, the CTLA-4 compound is abatacept.

According to other particular embodiments, such compound is a TNF α inhibitor, such as adalimumab, certolizumab, etanercept, golimumab or infliximab. According to more particular embodiments, the TNF α inhibitor is adalimumab. According to other more particular embodiments, the TNF α inhibitor is certolizumab. According to other more particular embodiments, the TNF α inhibitor is etanercept. According to other more particular embodiments, the TNF α inhibitor is golimumab. According to other more particular embodiments, the TNF α inhibitor is infliximab.

According to other particular embodiments, the autoantigen is for use in the prevention and/or treatment of latent autoimmune diabetes, such as latent autoimmune diabetes in a GAD-antibody positive individual.

According to particular embodiments, the autoimmune disease is type 1 diabetes.

According to other particular embodiments, the autoimmune disease is autoimmune diabetes.

According to other particular embodiments, the autoimmune disease is latent autoimmune diabetes.

According to other particular embodiments, the autoimmune disease is recurrence of autoimmune diabetes, such as recurrence of autoimmune diabetes in an individual (e.g. a human) with autoimmune diabetes that has been subject to islet cell transplantation or other cell therapies including stem cell therapy.

Hence, the present invention provides a combination (e.g. a therapeutic combination) comprising at least one autoantigen and at least one IL-10 inducing compound.

More particularly, the present invention provides a combination (e.g. a therapeutic combination) comprising i) at least one autoantigen selected from the group consisting of insulin, B chain insulin, proinsulin, and β cell autoantigens, and ii) at least one IL-10 inducing compound selecting from the group consisting of vitamin D, vitamin D analogs and tyrosine kinase inhibitors.

According to certain embodiments, the at least one autoantigen is a β cell autoantigen, such as, glutamic acid decarboxylase (GAD), insulinoma antigen-2, ZnT8, islet-specific glucose-6-phosphate catalytic subunit-related protein (IGRP) or chromogranin A.

According to particular embodiments, the β cell autoantigen is GAD, such as GAD-65 including fragments thereof, derivatives thereof, or a nucleotide coding therefor.

According to more particular embodiments, the β cell autoantigen is GAD-65, a fragment thereof, derivative thereof, or a nucleotide coding therefor. According to more particular embodiments, the β cell autoantigen is GAD-65. According to other particular embodiments, the β cell autoantigen is a fragment derived from GAD-65 (i.e. a GAD65 fragment.

According to other particular embodiments, the β cell autoantigen is insulinoma antigen-2.

According to other particular embodiments, the β cell autoantigen is ZnT8.

According to other particular embodiments, the β cell autoantigen is islet-specific glucose-6-phosphate catalytic subunit-related protein (IGRP).

According to other particular embodiments, the β cell autoantigen is chromogranin A.

According to certain other embodiments, the at least one autoantigen is insulin.

According to certain other embodiments, the at least one autoantigen is B chain insulin.

According to certain other embodiments, the at least one autoantigen is proinsulin.

The combination according to the invention may comprise more than one autoantigen. Thus, according to certain embodiments, the combination comprises at least two autoantigens. According to certain other embodiments, the combination comprises at least three autoantigens. According to certain other embodiments, the combination comprises at least four autoantigens.

Therefore, according to particular embodiments, the combination comprises at least GAD, such as GAD-65, and insulin. According to other particular embodiments, the combination comprises at least insulinoma antigen-2 and insulin. According to other particular embodiments, the combination comprises at least ZnT8 and insulin. According to other particular embodiments, the combination comprises at least IGRP and insulin. According to other particular embodiments, the combination comprises at least chromogranin A and insulin.

According to other particular embodiments, the combination comprises at least GAD, such as GAD-65, and B chain insulin. According to other particular embodiments, the combination comprises at least insulinoma antigen-2 and B chain insulin. According to other particular embodiments, the combination comprises at least ZnT8 and B chain insulin. According to other particular embodiments, the combination comprises at least IGRP and B chain insulin. According to other particular embodiments, the combination comprises at least chromogranin A and B chain insulin.

According to other particular embodiments, the combination comprises at least GAD, such as GAD-65, and proinsulin. According to other particular embodiments, the combination comprises at least insulinoma antigen-2 and proinsulin. According to other particular embodiments, the combination comprises at least ZnT8 and proinsulin. According to other particular embodiments, the combination comprises at least IGRP and proinsulin. According to other particular embodiments, the combination comprises at least chromogranin A and proinsulin.

According to other particular embodiments, the combination comprises at least insulin and B chain insulin. According to other particular embodiments, the combination comprises at least insulin and proinsulin. According to other particular embodiments, the combination comprises at least B chain insulin and proinsulin.

According to particular embodiments, the combination comprises at least GAD, such as GAD-65, insulin and B chain insulin. According to other particular embodiment, the combination comprises at least GAD, such as GAD-65, insulin and proinsulin. According to yet other particular embodiments, the combination comprises at least GAD, such as GAD-65, B chain insulin and proinsulin. According to yet other particular embodiments, the combination comprises at least insulin, B chain insulin and proinsulin.

According to other particular embodiments, the combination comprises GAD, such as GAD-65, insulin, B chain insulin and B chain insulin.

According to certain embodiments, the at least one autoantigen, such as the at least two autoantigens or at least three autoantigens, is formulated in an adjuvant.

According to particular embodiments, the adjuvant is alum.

According to certain embodiments, the at least one IL-10 inducing compound is vitamin D or a vitamin D analog. According to particular embodiments, the at least one IL-10 inducing compound is vitamin D.

According to more particular embodiments, the at least one IL-10 inducing compound is 1,25-Dihydroxyvitamin D.

According to certain other embodiments, the at least one IL-10 inducing compound is a vitamin D analog, such as TX527.

According to certain other embodiments, the at least one IL-10 inducing compound is a tyrosine kinase inhibitor, such as dasatinib, bosutinib, saracatinib, imatinib, sunitinib, or combinations thereof.

According to particular embodiments, the tyrosine kinase inhibitor is dasatinib.

According to other particular embodiments, the tyrosine kinase inhibitor is bosutinib.

According to other particular embodiments, the tyrosine kinase inhibitor is saracatinib.

According to other particular embodiments, the tyrosine kinase inhibitor is imatinib.

According to other particular embodiments, the tyrosine kinase inhibitor is sunitinib.

According to other particular embodiments, the tyrosine kinase inhibitor is a combination of at least two of dasatinib, bosutinib, saracatinib, imatinib and sunitinib. For example, the tyrosine kinase inhibitor may be a combination of dasatinib and bosutinib. According to other more particular embodiments, the tyrosine kinase inhibitor is a combination of dasatinib and saracatinib. According to other more particular embodiments, the tyrosine kinase inhibitor is a combination of dasatinib and imatinib. According to other more particular embodiments, the tyrosine kinase inhibitor is a combination of dasatinib and sunitinib. According to other more particular embodiments, the tyrosine kinase inhibitor is a combination of bosutinib and saracatinib. According to other more particular embodiments, the tyrosine kinase inhibitor is a combination of bosutinib and imatinib. According to other more particular embodiments, the tyrosine kinase inhibitor is a combination of bosutinib and sunitinib. According to other more particular embodiments, the tyrosine kinase inhibitor is a combination of imatinib and sunitinib According to other more particular embodiments, the tyrosine kinase inhibitor is a combination of dasatinib, bosutinib and saracatinib.

The combination according to the invention may comprise more than one IL-10 inducing compound. Thus, according to certain embodiments, the combination comprises at least two IL-10 inducing compounds. According to certain other embodiments, the combination comprises at least three IL-10 inducing compounds. According to certain other embodiments, the combination comprises at least four IL-10 inducing compounds.

Therefore, according to particular embodiments, the combination comprises at least Vitamin D and a tyrosine kinase inhibitor. According to other particular embodiments, the combination comprises at least a Vitamin D analog and a tyrosine kinase inhibitor.

According to more particular embodiments, the combination comprises at least Vitamin D and dasatinib. According to other more particular embodiments, the combination comprises at least Vitamin D and bosutinib. According to other more particular embodiments, the combination comprises at least vitamin D and saracatinib. According to other more particular embodiments, the combination comprises at least vitamin D and imatinib. According to other more particular embodiments, the combination comprises at least vitamin D and sunitinib.

According to more particular embodiments, the combination comprises at least a vitamin D analog and dasatinib. According to other more particular embodiments, the combination comprises at least a vitamin D analog and bosutinib. According to other more particular embodiments, the combination comprises at least a vitamin D analog and saracatinib. According to other more particular embodiments, the combination comprises at least a vitamin D analog and imatinib. According to other more particular embodiments, the combination comprises at least a vitamin D analog and sunitinib.

According to certain embodiments, the combination further comprises iii) a compound that reduces the dendritic cells' ability to activate naïve $CD4^+$ T cells, such as a cyclooxygenase inhibitor, a CTLA-4 compound or a TNF $\alpha$ inhibitor.

According to particular embodiments, such compound is a cyclooxygenase inhibitor, such as a non-steroidal anti-inflammatory drug (NSAID). According to more particular embodiments, the NSAID is selected from the group consisting of ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, aspirin (acetylsalicylic acid), diflunisal (Dolobid®), salicylic acid, salsalate (Disalcid®), piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, and nimesulide.

According to certain embodiments, the cyclooxygenase inhibitor is a propionic acid derivative, such as ibuprofen, dexibuprofen, naproxen, fenoprofen, ketoprofen, dexketoprofen, flurbiprofen, oxaprozin or loxoprofen.

According to certain embodiments, the cyclooxygenase inhibitor is a Acetic acid derivative, such as indomethacin, tolmetin, sulindac, etodolac, ketorolac, diclofenac, aceclofenac or nabumetone.

According to certain embodiments, the cyclooxygenase inhibitor is a salicylate, such as aspirin (acetylsalicylic acid), diflunisal (Dolobid®), salicylic acid or salsalate.

According to certain embodiments, the cyclooxygenase inhibitor is an enolic acid (oxicam) derivative, such as piroxicam, meloxicam, tenoxicam, droxicam, dornoxicam or isoxicam.

According to certain embodiments, the cyclooxygenase inhibitor is an anthranilic acid derivative, such as Mefenamic acid, Meclofenamic acid, Flufenamic acid or tolfenamic acid.

According to certain embodiments, the cyclooxygenase inhibitor is selective COX-2 inhibitor, such as celecoxib, rofecoxib, valdecoxibvaldecoxib, parecoxib, lumiracoxib or etoricoxib.

According to more particular embodiments, the cyclooxygenase inhibitor is ibuprofen.

According to more particular embodiments, the cyclooxygenase inhibitor is dexibuprofen.

According to more particular embodiments, the cyclooxygenase inhibitor is Naproxen.

According to more particular embodiments, the cyclooxygenase inhibitor is fenoprofen According to more particular embodiments, the cyclooxygenase inhibitor is ketoprofen.

According to more particular embodiments, the cyclooxygenase inhibitor is dexketoprofen.

According to more particular embodiments, the cyclooxygenase inhibitor is flurbiprofen.

According to more particular embodiments, the cyclooxygenase inhibitor is oxaprozin.

According to more particular embodiments, the cyclooxygenase inhibitor is loxoprofen.

According to more particular embodiments, the cyclooxygenase inhibitor is Indomethacin.

According to other particular embodiments, such compound is a CTLA-4 compound, such as a cytotoxic T-lymphocyte-associated antigen 4 immunoglobulin.

According to more particular embodiments, the CTLA-4 compound is abatacept.

According to other particular embodiments, such compound is a TNF α inhibitor, such as adalimumab, certolizumab, etanercept, golimumab or infliximab. According to more particular embodiments, the TNF α inhibitor is adalimumab. According to other more particular embodiments, the TNF α inhibitor is certolizumab. According to other more particular embodiments, the TNF α inhibitor is etanercept. According to other more particular embodiments, the TNF α inhibitor is golimumab. According to other more particular embodiments, the TNF α inhibitor is infliximab.

The combination of the present invention may be used in therapy, in particular in the prevention and/or treatment of an autoimmune disease. Accordingly, the combination of the present invention may be a therapeutic combination.

According to certain embodiments, the combination is for use as medicament, such as for use in the prevention and/or treatment of an autoimmune disease.

According to particular embodiments, the combination is for use in the prevention and/or treatment of type 1 diabetes.

According to other particular embodiments, the combination is for use in the prevention and/or treatment of autoimmune diabetes.

According to other particular embodiments, the combination is for use in the prevention and/or treatment of latent autoimmune diabetes.

According to yet other particular embodiments, the combination is for use in the prevention and/or treatment of recurrence of autoimmune diabetes, such as recurrence of autoimmune diabetes in an individual (e.g. a human) with autoimmune diabetes that has been subject to islet cell transplantation or other cell therapies including stem cell therapy.

The present invention provides in a further aspect the use of a composition or combination comprising i) at least one autoantigen, such as at least one autoantigen as detailed above, ii) at least one IL-10 inducing compound, such as at least one IL-10 as detailed above, and optionally iii) a compound that reduces the dendritic cells' ability to activate naïve CD4$^+$ T cells, such as a compound that reduces the dendritic cells' ability to activate naïve CD4$^+$ T cells as detailed above, in the manufacture of a medicament.

The present invention provides in a further aspect method (s) for the prevention and/or treatment of an autoimmune disease in an individual in need thereof, the method(s) comprises administering to said individual at least one autoantigen, such as at least one autoantigen as detailed above; and administering to said individual at least one IL-10 inducing compound, such as at least one IL-10 as detailed above.

According to certain embodiments, the methods further comprise administering to said individual a compound that reduces the dendritic cells' ability to activate naïve CD4$^+$ T cells, such as a compound that reduces the dendritic cells' ability to activate naïve CD4$^+$ T cells as detailed above.

According to certain embodiments, the individual to be treated according to the present invention is a mammal.

According to particular embodiments, the individual to be treated according to the present invention is a human.

According to certain embodiments, the individual to be treated according to the present invention is an adult.

According to particular embodiments, the individual to be treated according to the present invention is an adult human.

The medicaments, pharmaceutical compositions or therapeutic combinations according to the present invention may be in any form suitable for the application to humans and/or animals, preferably humans including infants, children and adults and can be produced by standard procedures known to those skilled in the art. The medicament, (pharmaceutical) composition or therapeutic combination can be produced by standard procedures known to those skilled in the art, e.g. from the table of contents of "Pharmaceutics: The Science of Dosage Forms", Second Edition, Aulton, M. E. (ED. Churchill Livingstone, Edinburgh (2002); "Encyclopedia of Pharmaceutical Technology", Second Edition, Swarbrick, J. and Boylan J. C. (Eds.), Marcel Dekker, Inc. New York (2002); "Modern Pharmaceutics", Fourth Edition, Banker G. S. and Rhodes C. T. (Eds.) Marcel Dekker, Inc. New York 2002 y "The Theory and Practice of Industrial Pharmacy", Lachman L., Lieberman H. And Kanig J. (Eds.), Lea & Febiger, Philadelphia (1986). The respective descriptions are hereby incorporated by reference and form part of the disclosure. The terms "medicament", "pharmaceutical composition" and "pharmaceutical formulations" may be used interchangeably.

The pharmaceutical composition of the present invention may for example be administered parenterally, including intramuscular, intraperitoneal, or intravenous injection, transmucosal or sublingual application; or orally, including administration as tablets, pellets, granules, capsules, lozenges, aqueous or oily solutions, suspensions, emulsions, sprays or as reconstituted dry powdered form with a liquid medium.

Likewise, the at least one autoantigen used in accordance with the present invention may for example be administered parenterally, including intramuscular, intraperitoneal, or intravenous injection, transmucosal or sublingual application; or orally, including administration as tablets, pellets, granules, capsules, lozenges, aqueous or oily solutions, suspensions, emulsions, sprays or as reconstituted dry powdered form with a liquid medium.

Likewise, the at least one IL-10 inducing compound used in accordance with the present invention may for example be administered parenterally, including intramuscular, intraperitoneal, or intravenous injection, transmucosal or sublingual application; or orally, including administration as tablets, pellets, granules, capsules, lozenges, aqueous or oily solutions, suspensions, emulsions, sprays or as reconstituted dry powdered form with a liquid medium.

Likewise, the therapeutic combination of the present invention may for example be administered parenterally, including intramuscular, intraperitoneal, or intravenous injection, transmucosal or sublingual application; or orally, including administration as tablets, pellets, granules, capsules, lozenges, aqueous or oily solutions, suspensions, emulsions, sprays or as reconstituted dry powdered form with a liquid medium.

According to certain embodiments, the at least one autoantigen is administered intrainguinal.

According to certain other embodiments, the at least one autoantigen is administered is intradermal or subcutaneous, such as in the stomach close to the pancreatic draining lymph nodes. According to particular embodiments, the at least one autoantigen is administered is intradermal. According to other particular embodiments, the at least one autoantigen is administered is subcutaneous.

The medicament, pharmaceutical composition or therapeutic combination according to the present invention may further comprise one or more pharmaceutically acceptable excipients.

Carriers, diluents and excipients which are suitable for the preparation of a medicament, pharmaceutical composition or therapeutic combination according to the present invention are well known to those skilled in the art, e.g. from the "Handbook of Pharmaceutical Excipients" Sixth Edition, Raymond C. Rowe, Paul J. Sheskey and Marian E Quinn (Eds.), American Pharmaceutical Association (July 2009), which is hereby incorporated by reference and forms part of the disclosure.

The at least one autoantigen and the at least one IL-10 inducing compound may be administered simultaneously or separately. According to certain embodiments, the at least one autoantigen and the at least one IL-10 inducing compound are administered simultaneously. According to certain embodiments, the at least one autoantigen and the at least one IL-10 inducing compound are administered separately.

According to certain embodiments, the at least one IL-10 inducing compound is administered prior to administration of the at least one autoantigen. According to particular embodiments, the at least one IL-10 inducing compound is administered at least one day, such as at least two days, at least three days, at least four days, at least five days, at least six days or at least one week, prior to the first administration of the at least one autoantigen. Hence, according to such embodiments, a course of IL-10 inducing compound(s) is commenced at least one day, such as at least two days, at least three days, at least four days, at least five days, at least six days or at least one week prior to first administration of the at least one autoantigen.

According to more particular embodiments, the at least one IL-10 inducing compound is administered at least one week, such as at least two weeks, prior to the first administration of the at least one autoantigen. Hence, according to such embodiments, a course of IL-10 inducing compound(s) is commenced at least one week, such as at least two weeks, prior to first administration of the at least one autoantigen.

The compound that reduces the dendritic cells' ability to activate naïve $CD4^+$ T cells may be administered simultaneously or separately with the at least one autoantigen and/or the at least one IL-10 inducing compound. According to certain embodiments, the CTLA-4 compound is administered simultaneously with the at least one autoantigen. According to certain other embodiments, the compound that reduces the dendritic cells' ability to activate naïve $CD4^+$ T cells is administered separately to the at least one autoantigen.

According to certain embodiments, the at least one IL-10 inducing compound and the compound that reduces the dendritic cells' ability to activate naïve $CD4^+$ T cells are administered simultaneously. According to certain embodiments, the at least one IL-10 inducing compound and the compound that reduces the dendritic cells' ability to activate naïve $CD4^+$ T cells are administered separately.

According to particular embodiments, the compound that reduces the dendritic cells' ability to activate naïve $CD4^+$ T cells, such as for example 10 mg/kg abatacept, is administered+/−7 days around the time of first administration of the at least one autoantigen.

According to certain embodiments, administration of the at least one autoantigen and administration of the compound that reduces the dendritic cells' ability to activate naïve $CD4^+$ T cells is repeated on day 14, 28 and 45+/−one week as the case may be to ensure blockage of CD28 on T cells.

According to certain embodiments, at least one 2-20 ug dose GAD, such as GAD-65, optionally formulated in alum, is administered per treatment occasion.

According to certain embodiments, at least one 1000-2000 IU vitamin D, such as vitamin D3, is administered per treatment occasion.

According to certain embodiments, APCs are made more tolerogenic by administering between 7,000-70,000 IU of vitamin D, such as vitamin D3, per week for between 1-10 weeks prior to first administration of the at least one autoantigen and for 4 weeks after last administration of the at least one autoantigen.

According to certain embodiments, administrations of GAD, such as GAD-65, optionally formulated in alum, are made approximately one week following each administration of the compound that reduces the dendritic cells' ability to activate naïve $CD4^+$ T cells.

According to certain embodiments, at least one 400 mg dose of NSAID, such as ibuprofen, is administered per treatment occasion.

The invention assumes the understanding of conventional molecular biology methods that include techniques for manipulating polynucleotides that are well known to the person of ordinary skill in the art of molecular biology. Examples of such well known techniques can be found in Molecular Cloning: A Laboratory Manual 2nd Edition, Sambrook et al., Cold Spring Harbor, N.Y. (1989). Examples of conventional molecular biology techniques include, but are not limited to, in vitro ligation, restriction endonuclease digestion, PCR, cellular transformation, hybridization, electrophoresis, DNA sequencing, and the like.

The invention also assumes the understanding of conventional immunobiological methods that are well known to the person of ordinary skill in the art of immunology. Basic information and methods can be found in Current Protocols in Immunology, editors Bierer et al., 4 volumes, John Wiley & Sons, Inc., which includes teachings regarding: Care and Handling of Laboratory Animals, Induction of Immune Responses, In Vitro Assays for Lymphocyte Function, In Vivo Assays for Lymphocyte Function, Immunofluorescence and Cell Sorting, Cytokines and Their Cellular Receptors, Immunologic Studies in Humans, Isolation and Analysis of Proteins, Peptides, Molecular Biology, Biochemistry of Cell Activation, Complement, Innate Immunity, Animal Models for Autoimmune and Inflammatory Disease (which includes chapters on the NOD mouse model, the SLE mouse model (for lupus), and induction of autoimmune disease by depletion of regulatory T cells), Antigen Processing and Presentation, Engineering Immune Molecules and Receptors, Ligand-Receptor Interactions in the Immune System, Microscopy, and Abbreviations and Terminology for common immune system genes and proteins, including the CD system for Leukocyte Surface Molecules.

EXAMPLES

The following examples disclose studies that may be performed in order to establish the safety and efficacy of various aspects of the present invention. The β cell autoantigen used in the examples is glutamic acid decarboxylase (GAD), and may be replaced with any other β cell autoantigen as described herein.

Example 1

Clinical Trial in Patients with Recent Onset Type 1-Diabetes Study Design:

The study is a 4-arm, randomized, double-blind, placebo-controlled, multicenter, clinical trial. Patients in arm A received oral 400 mg ibuprofen per day for 90 days every morning. From day 1 the patients also received oral 2000 IU vitamin D per day during 15 months (i.e. 25 drops per day), and 2 subcutaneous injections in the stomach area of 20 µg Diamyd® (a GAD-based diabetes therapy) in a prime-and-boost regimen day 15 and 45.

Arm B received oral 2000 IU vitamin D per day during 15 months (i.e. 25 drops per day), and 2 subcutaneous injections of 20 µg Diamyd® in a prime-and-boost regimen day 15 and 45.

Arm C received oral 2000 IU vitamin D per day during 15 months (i.e. 25 drops per day), and receive 2 subcutaneous injections of 20 µg Diamyd® at two different sites (which gives a total of 40 µg Diamyd® per occasion) in a prime-and-boost regimen day 15 and 45.

Arm D received placebo.

The patients will be followed for a total of 30 months with a blinded study period of 6 months.

Description of Treatment Groups:

The patients were assessed for eligibility at the screening visit (Visit 1) 2 to 4 weeks prior to the start of the treatment. On visit 2 (day 1, baseline), patients eligible for the study were randomized to 1 of 4 treatment groups:

15 patients were assigned to receive ibuprofen as oral suspension; 400 mg every morning from day 1 through 90 and from day 1 through 450 also oral drops of vitamin D 2000 IU per day (i.e. 25 drops per day). In addition 1 subcutaneous injection with 20 µg Diamyd® and one with placebo given at two different sites in the stomach area, each on days 15 and 45, i.e., prime and booster dose (providing a total dose of 40 µg Diamyd®).

15 patients were assigned to receive placebo as oral suspension every morning from day 1 through 90 and from day 1 through 450 also oral drops of vitamin D 2000 IU per day (i.e. 25 drops per day). In addition 1 subcutaneous injection with 20 µg Diamyd® and one with placebo given at two different sites in the stomach area, each on days 15 and 45, i.e., prime and booster dose (providing a total dose of 40 µg Diamyd®).

15 patients were assigned to receive placebo as oral suspension every morning from day 1 through 90 and from day 1 through 450 also oral drops of vitamin D 2000 IU per day (i.e. 25 drops per day). In addition 2 subcutaneous injections with 20 µg Diamyd® given at two different sites in the stomach area, each on days 15 and 45, i.e., prime and booster doses (providing a total dose of 80 µg Diamyd®).

15 patients were assigned to receive placebo as oral suspension every morning from day 1 through 90 and placebo oral drops from day 1 through 450, and 2 subcutaneous injections with placebo (given at two different sites in the stomach area), each on days 15 and 45.

Efficacy Variables:

The primary and secondary efficacy endpoints include

Change in C peptide (90 minute value and AUCmean 0-120 min) during an MMTT.

Proportion of patients with a stimulated maximum C peptide level above 0.2 nmol/L Biomarkers, mechanistic data.

Fasting C peptide, change between baseline and 6 month.

Safety Variables:

The safety assessment includes observation of reactions at the injection site, GAD65Ab titer, occurrence of adverse events (AEs), laboratory measurements, vital signs, neurological assessments, and limited physical examination.

Results from 20 patients that completed 6 months in the study show that improved β cell function is seen for the patient group having received the Diamyd® involving treatment compared to the placebo treated group.

| | GADA+ | | C-Peptide Visit 2 | | | Visit 6 | | | Max (6 month)- |
|---|---|---|---|---|---|---|---|---|---|
| Patient ID | Visit 3 | Visit 5 | 60 min | 90 min | 120 min | 60 min | 90 min | 120 min | Max (baseline) |
| Identified as Placebo group | 1st inj | 3 mths | | | | | | | |
| 3 | 678 | 228.5 | 0.23 | 0.28 | 0.27 | 0.13 | 0.11 | 0.11 | −0.15 |
| 4 | 2053 | 2117 | 0.71 | 0.75 | 0.68 | 0.77 | 0.69 | 0.64 | 0.02 |
| 31 | 465.8 | 345.3 | 0.77 | 0.79 | 0.72 | 0.63 | 0.73 | 0.69 | −0.06 |
| 63 | 1378 | 1187 | 0.86 | 1.00 | 1.01 | | 0.60 | | −0.41 |
| 49 | 118.6 | 114 | 0.90 | 0.91 | 0.90 | 0.66 | 0.82 | 1.07 | 0.16 |
| 48 | 555 | 1187 | 1.29 | 1.40 | 1.88 | 1.40 | 1.55 | 1.58 | −0.30 |
| 9 | 61.4 | 224 | 0.35 | 0.38 | 0.34 | 0.15 | 0.17 | 0.15 | −0.21 |
| Mean (max-max) | | | | | | | | | −0.14 |
| Identified as active group | 1st injection | 3 mths | | | | | | | |
| 1 | 964 | 5460 | 0.91 | 0.96 | 1.03 | 0.95 | 1.44 | 1.47 | 0.44 |
| 6 | 992 | 2622 | 0.48 | 0.44 | 0.51 | 0.41 | 0.41 | 0.33 | −0.10 |
| 17 | 266.7 | 2408 | 0.53 | 0.48 | 0.51 | 0.53 | 0.55 | 0.59 | 0.06 |
| 25 | 109.3 | 1823 | 0.61 | 0.70 | 0.70 | 0.77 | 0.81 | 0.70 | 0.11 |
| 28 | 393.7 | 1931 | 0.67 | 0.82 | 0.76 | 0.84 | 0.87 | 0.88 | 0.06 |
| 33 | 340.4 | 1095 | 0.58 | 0.64 | 0.64 | 0.61 | 0.62 | 0.66 | 0.02 |
| 35 | 125.8 | 4300 | 0.96 | 1.14 | 1.16 | 0.75 | 0.72 | 0.79 | −0.37 |
| 40 | 604 | 3506 | 0.37 | 0.44 | 0.53 | 0.15 | 0.12 | 0.12 | −0.38 |
| 41 | 2266 | 4230 | 0.52 | 0.42 | 0.40 | 0.20 | 0.17 | 0.13 | −0.32 |
| 46 | 132.0 | 3485 | 0.65 | 0.82 | 0.88 | 0.32 | 0.49 | 0.51 | −0.37 |
| 47 | 135.1 | 3574 | 1.49 | 1.71 | 1.58 | 1.08 | 1.30 | 1.66 | −0.05 |
| 53 | 967 | 4104 | 0.90 | 0.84 | 0.85 | 0.97 | 0.94 | 0.78 | 0.07 |
| 54 | 162.4 | 2035 | 0.77 | 0.69 | 0.68 | 0.81 | 0.87 | 1.01 | 0.24 |
| Mean (max-max) | | | | | | | | | 0.04538 |

Example 2

Pilot Trial to Preserve Residual Insulin Secretion in Adults with Recent-Onset Type 1 Diabetes by Giving GAD-Antigen (Diamyd®) Therapy into Lymph Nodes. (DIAGNODE)

1.1 Background and rationale

The incidence of type 1 diabetes (T1D) in children is next to Finland highest in Sweden in the world, and is increasing rapidly. T1D is by far the most common chronic, serious, life-threatening disease among children and adolescents in our country, and the incidence of type 1 diabetes is high also in young adults. The disease tends to become an extremely serious global problem. The disease is characterized by lack of insulin. Even though several patients at diagnosis have rather impressive residual β cell function (1) the deficiency becomes soon very pronounced and finally complete (2,3). Residual insulin secretion is of crucial importance. In rare cases the β cell function improves so much shortly after diagnosis that glucose metabolism normalizes and no insulin is required for some time, that is the patient goes into so called complete remission (4). As long as the patient is in a complete remission there is no need of active treatment, more than perhaps some recommendation of sound life style regarding physical exercise and diet. There are no symptoms, no acute complications and if somebody stayed in complete remission it is unlikely that such an individual would ever develop late complications. Slight abnormality of glucose or lipid metabolism might increase the risk of macrovascular complications in the same way as for individuals with chemical diabetes or impaired glucose tolerance. Complete remission is rare, but partial remission it is not (4). During this period the patient usually has near normal blood glucose values, not even mild hypoglycemia and no episodes of ketoacidosis. The quality of life is very good as the patient feels well, children grow normally, few restrictions are needed, if any with regard to food, the patients can exercise with great variation without getting hypoglycemia, and experiences very good home blood glucose tests. Only some residual insulin secretion is enough to diminish the risk of ketoacidosis (5). Furthermore, it has been shown in the DCCT trial that even quite modest residual insulin secretion, a response to a β cell stimulation with serum C peptide >0.20 pmol/ml, plays an important role for prevention of complications (6). This effect may be due to the fact that residual insulin secretion should reasonably make it easier to reach good blood glucose balance, but it is also possible that C peptide per se has a physiological function. It has in fact been reported that C peptide influences vascular permeability, decreases leakage in retinal vessel, and not least has a positive effect on nerve function (7) although the effect of C peptide per se still is under debate.

1.1.1 Factors Influencing the Natural Course

At diagnosis of T1D it has been claimed that 80-90% of the β cells in pancreas have been destroyed. However, the proof for this is scarce, and it may well be that the main problem is deterioration of function. Furthermore there is great difference between patients, as some have quite good residual insulin secretion and others have not. Shortly after diagnosis, especially when an active insulin treatment is given, there is an increase of C peptide production, and at the same time an improvement of insulin sensitivity. Good metabolic control seems to improve the milieu and metabolism for the β cells and the β cell function is preserved, which in turn contributes to better metabolic control, and vice versa. The intensity of the autoimmune process plays a role, and it seems evident that children have a more aggressive immune process than adults with type 1 diabetes, but it is still difficult to predict the course. Some studies have suggested that high concentrations of autoantibodies are followed by a more rapid loss of insulin secretion, while others have not found such a relationship, or even the opposite. No special signs of cell-mediated immunity have so far been proven to predict β cell loss but our own studies have shown that disease process is related to a T-helper-1 (Th-1) deviation of the immune system with increases of certain cytokines such as IFN-γ and decrease of IL-10, IL-13.

The Effect of Insulin Treatment on β Cell Function.

Active insulin treatment during the first period of the disease prolonged the partial remission long time ago, and this finding could be confirmed and validated by improved residual insulin secretion (2). Intensified treatment seems to improve residual β cell function at least for some time (8), but it may also have long-term positive effects (9). Active treatment has been shown not only to prevent or postpone diabetes in experimental animals, but studies have indicated that such treatment could prevent diabetes in high risk individuals (10). However, when tried at a larger scale in the Diabetes Prevention Trial, parenteral insulin treatment did not prevent diabetes (11). Oral treatment with insulin might have an effect (12) and therefore further studies are needed.

1.1.2 Interventions

In the 1970ies it became clear that T1D is an autoimmune disease and therefore immune interventions were tried. We performed the first immune intervention studies in the world on diabetic children when we already 30 years ago used plasmapheresis in newly-diagnosed children and adolescents with some positive effects (13). As a side effect of that treatment a new protein with the weight 64 kD was found in plasma (14), which later showed to be Glutamic Acid Decarboxylase (GAD). The breakthrough, taken as a proof for the concept of immune intervention, was cyclosporine, which doubtless slowed down the autoimmune destructive process and gave improved residual insulin secretion, while other trials with immune suppression had minimal effect, especially so in children (15, 16, 17), or showed too serious adverse events or risks (18, 19). In an effort to modulate the immune system we used photopheresis. Although clear effects on the immune system were demonstrated in a double blind placebo-controlled trial (20), the clinical effect was minimal and almost no improvement of residual β cell function could be seen (21). Thus, with no successful immune intervention, our interest was directed to protective agents such as nicotinamide and diazoxide, with no or transient effect (22, 23, 24).

With increasing knowledge of the immune process leading to β cell destruction, it has become possible to direct more precisely the immune intervention to target the important T cells. Promising studies using anti-CD3antibodies in an attempt to block the destructive immune process have been performed. Results from both North-American and French trials with anti-CD3 have shown that it is possible to block the destructive autoimmune process and thereby at least postpone the decline of the β cell function (25,26). The decline of residual insulin secretion was significantly slowed down, but unfortunately it looks as if the decline was just delayed a year, and thereafter the declining C peptide curve went parallel to the declining curve in the placebo group. Furthermore, a majority of the patients experience some Cytokine Release Syndrome (CRS), which may be quite serious, and in addition a number of side effects were seen in most of the patients. We have participated in one of two recent phase III trials (Protege trial), which failed to reach the primary endpoint, although the arm with the most intense treatment indeed showed some preservation of residual insulin secretion and lower insulin requirement to reach good HbA1c (27; Sherry, Hagopian, Ludvigsson et al Lancet 2011). New studies are needed but it is difficult to believe that this type of treatment alone will be the accepted solution for general clinical use. Even less likely is such a treatment accepted as a preventive treatment in otherwise healthy individuals of whom many never would develop diabetes.

1.1.3 Immune Therapy with Auto-Antigens

In the treatment of allergic diseases, immunotherapy with small amount of disease specific antigen has been efficiently used during many years. The mechanism for this treatment remains unclear, although immune modulation of the immune responses and induction of regulatory cells have been suggested. In autoimmune diseases no such treatment has been successful, but should be tried (28). Experiments in diabetes prone animals have shown that treatment with a heat shock protein could delay or postpone development of diabetes. The use of Diapep277 peptide in a study in adults showed significant preservation of insulin secretion without almost any adverse events (29). Later trials in children and adolescents with T1D (30), however, have shown no effect. Studies with Diapep277 treatment in so called LADA (Latent Autoimmune Diabetes in the Adult) are ongoing, and preliminary results (report at IDF, Dubai December 2011 and at ADA June 2012) suggests that treatment with Diapep277 may preserve β cell function in adults with mild type 1 diabetes. However, the results are a bit unclear, as there was a weak C peptide preservation only seen after glucagon stimulation, but no effect at all after Mixed Meal Tolerance Test, and there was no differences whatsoever between the actively treated group and placebo in immune markers. Active treatment with insulin has been shown not only to prevent or postpone diabetes in experimental animals but preliminary open studies indicated that such treatment could prevent diabetes in high risk individuals (10). Insulin, clearly a β cell specific auto-antigen, has been parentally administrated (DPT) to prevent diabetes in high risk individuals with no effect, while oral insulin administration with the same purpose may have a slight effect (12).

1.1.4 Previous Clinical Studies with GAD-Alum 1.1.4.1 GAD-vaccination

GAD (Glutamic Acid Decarboxylase), can be regarded as an auto-antigen, as it is produced in the islets with increased release as response to β cell stimulation. This protein has been shown to deeply influence the autoimmune immune process (31, 32, 33, 34). Several studies have shown that indeed GAD can prevent diabetes in experimental animals (35-42). The similarity of GAD with viral proteins may be important for the therapeutic action. The observed effect, even after the start of the immune process, suggests that it might be possible to expect the same effect in humans after the start of the immune process. In a phase II study in LADA patients the administration of one low dose, Diamyd® 20 μg, led to improved β cell function for up to 2 years compared to the placebo treated group, with no side effects. Also other doses were tried: 4 μg showed no effect, 100 μg showed a similar effect as 20 μg, while 500 μg showed no effect. None of the doses showed any adverse events, still so after several years follow-up (43). Association with change in the ratio of $CD4^+CD25^+/CD4^-\ CD25^-$ cells was found, indicating a mechanism for the effect. With this promising background we started a phase II study in Type 1 diabetic patients 10-18 years with recent onset. Based on the idea that the treatment earlier had effect in slowly progressive LADA patients we included patients with up to 18 months duration of T1D diabetes at intervention. The patients were randomized to either 20 μg GAD-alum (Diamyd®) sc at day 1 and 30, or placebo. The effect still after 30 months was remarkable, and clearly both statistically and clinically significant (44), with about half of the C peptide decline in the GAD treated group compared with the placebo group. Patients with a diabetes duration <3 months had a remarkably good effect with no or minimal decline of β cell function during the follow-up of the first 15 months. Almost all effect was seen in patients with <6 months duration at vaccination. Even more, in contrast to other intervention treatments, this effect was gained with no adverse events at all, making the treatment very encouraging! Still after 48 months the patients treated with <6 months duration hade significantly preserved C peptide and still no adverse events (45). So far GAD-treatment looked very promising. Two phase III trials were performed, one European with Johnny Ludvigsson (JL) as PI, and one in USA with Jerry Palmer as PI and JL as coinvestigator. In the European trial 334 patients were recruited into three arms, one arm with GAD-alum (Dia-myd®) 20 μg at day 1, 30, 90 and 270, another arm with GAD-alum 20 μg at day 1 and 30, and placebo at day 90 and 270 and a third arm with placebo at day 1, 30, 90 and 270. Primary endpoint, serum C peptide AUC after a Mixed Meal Tolerance Test (MMTT) at 15 months was not met! (C peptide AUC p=0.1; Fasting C peptide p=0.07) (46). This prompted the company (Diamyd Medical+ Johnson&Johnson) to close the phase III trials early. How-ever, the phase III trial did show several positive effects. Thus statistically significant efficacy was seen in several pre-specified subgroups. Furthermore, 45 Swedish patients had passed the 30 month's visit when the study was stopped, and those 15 patients who had received two doses of GAD-alum (Diamyd®) 20 μg showed a significant preser-vation of C peptide after 30 months compared with placebo! This is especially remarkable as the Swedish patients were the ones without efficacy after 15 months, while efficacy was found after 15 months in the non-Nordic countries.

1.1.4.2 Possible Reasons to the Different Results Phase II and Phase III

In phase III randomization, patients receiving active drug were more often in the 10-11 year age group than in the 16-18 year age group whereas placebo was more frequent than active drug in the higher age group. This may have influenced the result. The phase II patients were treated in March-April and those patients in phase III who were treated in March-April had also significant effect of GAD-treat-ment. In the phase II trial no vaccinations were accepted, but in phase III influenza vaccination was allowed. Unfortu-nately an epidemic of H1N1-flu lead to that almost all patients were vaccinated, many of them in connection with the GAD-vaccinations.

In Sweden and Finland the vaccine contained squalen, suspected to influence the immune system towards auto-immunity, and in these two countries there was no efficacy of GAD-treatment, while the efficacy was significant in other European countries. Patients in Sweden who did not get the influenza vaccination close to the GAD-treatment, had better efficacy of GAD-treatment (46).

1.1.4.3 Ongoing DIABGAD-1 Trial

Since January 2013 the phase II DIABGAD-1 trial is ongoing in Sweden. This is a trial in 60 patients, 10-18 years old, with recent-onset type 1 diabetes, who are treated in a double-blind placebo-controlled randomized study with GAD-alum 20 μg resp 40 μg given twice with 30 days interval, in combination with vitamin D, 2000 units daily for 450 days, and ibuprofen 400 mg daily for 90 days. Recruit-ment is fulfilled and now closed. 60 patients are randomized and another 4 patients are screened, waiting for screening results. There are so far no serious adverse events judged as related to study medication, and very slight adverse events, not related to the treatment except for mild transient reac-tions on the site of injection of GAD-alum. An interim analyses is planned already after 6 months follow-up of all patients while more extended analyses will be performed after 15 and 30 months.

1.1.5. Intra Lymph-Node Immunotherapy

Antigen therapy aims at presenting the antigen to the T cells in the lymph nodes to get a new balance of the immune system and tolerance against the antigen. In the treatment of autoimmune diseases so far antigen has been given either orally, intranasally or subcutaneously, in order to present the antigen to antigen presenting/dendritic cells which in turn are expected to present the antigen to the T cells of the immune system. However, animal studies have shown that intralymphatic injections induce a strong and relevant T cell response (47,48) and in the allergy field clinical studies have shown that presentation of the antigen/allergen directly into the lymph nodes seems to be more effective than traditional administration (49). Lower doses of the allergen can be used, the number of treatments can be radically reduced, and there have been no treatment-related adverse events. Inguinal lymphnodes are readily accessible in patients and the pain associated with the injection is rated as below that of venous puncture (50). With this background it is our aim to study whether the same approach can be used in patients with the autoimmune form of type 1 diabetes. For ethical reasons we will do the first pilot trial in adults.

1.2 Hypothesis

The encouraging results of the phase II GAD trial and the partly positive results of the phase III European trial, support the concept that administration of GAD-alum (Diamyd®) may decrease the autoimmune process and contribute to preservation of residual insulin secretion. As previous stud-ies have indicated that the dose should be somewhere between 20 and 100 μg Diamyd®, a lower dose of 3 μg given three times should be adequate when administrated directly into lymph nodes. Injection of GAD-alum (Dia-myd®) directly into lymph nodes will give no serious adverse events, have desired immunological effects and will (shown in future studies) improve efficacy 2. Risk-Benefit Analyses The incidence of type 1 diabetes is next to Finland higher in Sweden than in any other country of the world. The incidence is continuously increasing for decades. The dis-ease cannot be cured and cannot be prevented. In spite of a very heavy, intensive, expensive treatment many patients get life-threatening serious both acute and late complications, and the mortality is much increased. At diagnosis many patients have some slight residual insulin secretion. As long as this is the case it is much easier to keep blood glucose stable, the incidence of hypoglycaemia decreases as well as the risk of ketoacidosis. Quality of life for the patient as well as for parents of children with diabetes is better as long as there is some residual insulin secretion.

Type 1 diabetes in adults differ from the disease in children and adolescents as the disease process often is milder, the decline of residual insulin secretion slower, and it is easier to control blood glucose. However, there are still great similarities, similar treatment and complications, and preservation of β cell function is also very important in adults.

It is evident that there is a great benefit of preservation of residual insulin secretion, and therefore therapies aiming at preservation of this function justify treatments that are quite heavy, even dangerous and expensive. Thus it has been regarded as justified to treat type 1 diabetes at onset with drugs like monoclonal antibodies against the CD3-receptor, which causes adverse events in principally all patients, some even quite serious adverse events and risks. Even pure cytostatics have been used.

In our proposed study we use GAD-alum (Diamyd®) 4 µg×3, a treatment which has been used in much larger doses given to children and adults with almost no adverse events seen during follow-up of thousands of patient years. In our study we plan to use a very low dose, which means that the general risk can be expected to be even lower, but the administration will be directly into a lymph node which might give local reactions. The effect on the immune system may become more pronounced but should not lead to any adverse effects. Previous studies in allergy (where one of the co-investigators, Helene Zachrisson has given the intra lymph node injections of alum-formulated allergens) have not shown any adverse effect neither generally nor locally). For safety reasons, as this is the first pilot trial ever with this type of autoantigen treatment into lymphnodes, we try first in adults who can give their free informed consent. Even though type 1 diabetes in adults is somewhat milder than in younger patients, it is of great value to preserve β cell function, and therefore the proposed treatment may be of great therapeutical value also for adult patients.

When summarizing the pros and cons, there is a clear possibility of therapeutic benefit of great importance, both for the participating patients, for patients in future studies, whereas the risk is very small. If these studies contribute to the development of a good treatment, this will be of enormous value for a great number of patients.

3. Aim of Present Study

Our aim of the present pilot study is to get information on whether GAD-alum can be given into lymph nodes without treatment related serious adverse events, to allow future phase II-studies with the same technique to improve efficacy in preserving residual insulin secretion in type 1 diabetes. Thus we want to see whether this treatment give any adverse events, and how treatment regimens influence the immune system, cause the desired Th-2 deviation, increase of T-regulatory cells, and hopefully indications of preservation of residual β cell function. Based on the short-term results of this pilot study (6 month follow-up) we then may want to design a larger phase II trial, to include younger patients and to get more robust information. The main long-term goal is then to find a treatment at onset of type 1 diabetes in young patients which is tolerable for the patients, safe, and which can preserve residual insulin secretion and give the patients a better quality of life, with less acute complications and in the long run less risk of late complications.

4. Objectives

Objectives:

To evaluate the safety of giving Diamyd® directly into lymph glands and to evaluate the immune response (51-54) and effect on preservation of endogenous insulin secretion, measured at baseline and after 6, 15 and 30 months.

5. Population

Adult patients with recent onset of type 1 diabetes at Linköping university hospital are given information about the study and they are asked to participate in the trial.

5.1 Inclusion criteria

1. Informed consent given by patients and guardians/ parents
2. Type 1 diabetes according to the ADA classification with <6 months diabetes duration
3. Age 18.00-29.99 years at diagnosis of type 1 diabetes
4. Fasting C peptide >0.12 nmol/ml
5. Pos GADA but <50 000 random units 6. Females must agree to avoid pregnancy and have a negative urine pregnancy test
7. Patients must agree to using adequate contraception, until 1 year after the last administration of GAD-Alum/ placebo 5.2 Exclusion Criteria 1. Previous or current treatment with immunosuppressant therapy (although topical or inhaled steroids are accepted)
2. Continuous treatment with any inflammatory drug (sporadic treatment e.g. because of headache or in connection with fever a few days will be accepted)
3. Treatment with any oral or injected anti-diabetic medications other than insulin
4. A history of anaemia or significantly abnormal haematology results at screening
5. A history of epilepsy, head trauma or cerebro-vascular accident, or clinical features of continuous motor unit activity in proximal muscles
6. Clinically significant history of acute reaction to vaccines or other drugs in the past
7. Treatment with any vaccine, including influenza vaccine, within 4 months prior to planned first study drug dose or planned treatment with any vaccine up to 4 months after the last injection with study drug.
8. Participation in other clinical trials with a new chemical entity within the previous 3 months
9. Inability or unwillingness to comply with the provisions of this protocol
10. A history of alcohol or drug abuse
11. A significant illness other than diabetes within 2 weeks prior to first dosing
12. Known human immunodeficiency virus (HIV) or hepatitis
13. Females who are lactating or pregnant (the possibility of pregnancy must be excluded by urine βHCG on-site within 24 hours prior to the GAD-alum treatment)
14. Males or females not willing to use adequate contraception until 1 year after the last GAD-alum treatment
15. Presence of associated serious disease or condition, including active skin infections that preclude subcutaneous injection, which in the opinion of the investigator makes the patient non-eligible for the study
16. Deemed by the investigator not being able to follow instructions and/or follow the study protocol 5.3 Recruitment and Screening Eligible subjects will have the study explained to them, and will receive the written patient information. After having had the time to review the nature of the study, they will have the opportunity to ask questions to the investigational team. If, after this, the subjects agree to participate, they will personally sign and date the written informed consent form. The patients will then receive a copy of the signed and dated patient information/informed consent form.

5.4 Patient Withdrawal

In accordance with the Declaration of Helsinki, the investigator must explain to the patient that they have the right to withdraw from the study at any time, and that this will in no way prejudice their future treatment. However, unless safety issues occur, we plan to follow the patients for the entire duration of the study in order to analyse efficacy and safety variables also for those patients withdrawing from the study. The reason for any kind of withdrawal must be recorded on the appropriate CRF.

There will be different categories for withdrawals from the study: Complete withdrawal (i.e. stopping investigational product and also continued efficacy and safety evaluations)

Standard reasons for withdrawing from further participation in the study and from the follow-up visits (and <e.g. blood tests>) may be:

Patient's decision (withdrawal of consent to participate)

Patient lost to follow-up

Standard reasons from withdrawing from taking further investigational product, but continuing follow-up visits and safety evaluations may be:

Unacceptable adverse events 0.12 nmol/L. In total, approximately 5 patients will be recruited at one site in Linköping, Sweden. The patients will be assessed for eligibility at the screening visit (Visit 1) 10 to 21 days prior to the start of treatment. The screened patients will be assigned a sequential screening number and this screening number will be used as patient identification throughout the study.

Patients who qualify for inclusion in the study will then be enrolled in the study to receive investigational study drug at the subsequent visits according to table 1 below. The patients will be followed for a total study period of 30 months which includes 8 visits to the site.

See table 1 below for an overview of the study visits.

TABLE 1

Schedule of Patient Visits, Visit Windows and Study Drug Administration

| | | Study | | | | | |
|---|---|---|---|---|---|---|---|
| | | | Intervention | | | Follow-up | |
| | Screening Day −10 to −21 Screening Visit 1 | Day 1 Baseline Visit 2 | Day 30 ± 3 Visit 3 | Day 60 ± 3 Visit 4 | Day 180 ± 14 Month 6 Visit 6 | Day 450 ± 14 Month 15 Visit 7 | Day 900 ± 30 Month 30 Visit 8 |
| GAD-Alum/ Placebo | | GAD-alum treatment | GAD-alum treatment | GAD-alum treatment | | | |

Patient request

Investigator's discretion

Patient lost to follow-up/non-attendance

Intercurrent illness

The patient becomes pregnant

Thus intra lymph node GAD-alum should not be given to the patient if the patient after inclusion in the study has got brain damage, epilepsia, head trauma, neurological disease any active, serious hormonal disease other than type 1 diabetes other severe autoimmune disease(except celiac disease which is accepted for inclusion)

immune-suppressive treatment cancer, cancer treatment any other diabetes drugs other than insulin any vaccination drug/alcohol abuse or if the patient has become pregnant or is no longer willing to use safe contraceptives during the study However, whenever a patient is withdrawn from a study, or for whatever reason is not coming to any further visits, a final study evaluation must be completed for that patient (visit < >)—stating the reason(s) why the patient was withdrawn from the study. All documentation concerning the patient must be as complete as possible. Withdrawals due to non-attendance must be followed up by the investigator to obtain the reason for non-attendance. Withdrawals due to intercurrent illnesses or adverse events must be fully documented in the case record form, with the addition of supplementary information if available and/or appropriate.

6. Treatment Procedures 6.1 Study Design and Treatment

The trial is single center, open-label, pilot study in GADA positive T1D patients of either gender, 18.00 to 29.99 years old, diagnosed with T1D within 6 months at time of screening (Visit 1) and fasting C peptide levels equal to or above 6.2 Assessments and Procedures 1. Standard insulin treatment, education and psychosocial support for newly diagnosed type 1 diabetes patients.

2. Normalization of fluid, electrolyte and acid-base balance.

3. Thereafter information about the study.

4. When the patients have given their informed consent, at the latest 120 days after diagnosis, screening is performed with a fasting venous sample from patients who are eligible according to other criteria than C peptide and GADA concentrations (Visit 1).

5. At Baseline (Visit 2), 6, 15 and 30 months, assessment of residual endogenous insulin secretion by MMTT. HbA1c, safety (haematology and chemistry), autoantibody titres (GAD65, IA-2), immunology, are followed by blood samples at every study visit. Exogenous insulin dose/24 hours, Aes and concomitant medication is registered at every study visit.

6. Self-reported hypoglycaemia (defined as needing help from others and/or seizures and/or unconscious) registered at every study visit.

7. Any symptoms or signs of other medical problem should be treated at the discretion of the clinical doctor.

Examinations will be performed according to Table 2 in Section 7 below, and in the order outlined in the case report form (CRF).

6.2.1 all Visits, Visit 1 Through 7

Note that the patient should attend all study visits in the morning following an overnight fast (>10 hours, water allowed). For patients with evidence of an infection (including fever), the complete visit should be postponed for 5 days or until the patient has recovered.

6.2.2 Administrations of GAD-Alum, Visits 2, 3 and 4

After administration, the patient shall remain in the vicinity of the study site for the next hour, and the administration site will be examined by investigator/study nurse 1 hour post injection.

51

6.2.3 Mixed Meal Tolerance Test (MMTT), Visits 2, 5, 6 and 7

The MMTT must be performed according to the instructions in the CRF. The patient should:

Come to the study site following an overnight fast (>10 hr), i.e. the patient may not eat but is permitted to drink water Not take short acting/direct acting insulin within 6 hours before the MMTT. The patient is allowed to take base-insulin day/night before, but not in the morning before the MMTT.

Patients with CSII (insulin pump) must continue with their basal dose insulin, but not add bolus dose during the last 6 hours before the MMTT Have a fasting plasma glucose level in the range defined by 4-12 mmol/L on the patient's home blood glucose meter in the morning of the test If the patient does not fulfil all of the above criteria, the MMTT should be rescheduled and the patient should return to the study site within 5 days if possible.

If for safety reasons, subjects need to eat or take insulin, the visit should also be rescheduled.

6.3 Laboratory Tests and Examinations:

1. Immunological tests:
   a. Autoantibodies (Anti-GAD65, Anti-Insulin, Anti-IA-2, ZnT8)
   b. Relevant cytokines and chemokines are determined (see below)
   c. T cells are classified and studied (see below)
2. Genetics:
   a. HLA determinations is done and genes related to diabetes development
   b. Array studies to elucidate the importance of diabetes-related genes
3. Virus assays:
   a. Genetic, immunological and microbiological tests may be used.
4. Diabetes status:
   a. HbA1c
   b. Fasting glucose and fasting C peptide
   c. Meal stimulated glucose and C peptide
5. Blood sampling for safety:
   a. Hematology
   b. Chemistry 6.4 Medical History A complete review of the subject's past medical history will be undertaken by the investigator and documented on the Medical History CRF.

All pre-existing conditions/diseases will be reported on the Medical History CRF page at the screening visit (Visit 1).

The subject's type 1 diabetes diagnosis date and family history of type 1 diabetes will also be documented.

6.5 Physical Examination Including Neurological Examination

At the screening visit (Visit 1) the patient will undergo a general physical examination and a neurological examination and any findings will be reported as pre-existing conditions on the Medical History CRF page.

During the subsequent study visits the patient will be examined for any new medical conditions or worsening of the pre-existing ones. Any change in pre-existing conditions or new conditions must be entered on the AE page in the CRF and any medication given on the concomitant medication pages.

The patients will, in addition to the limited physical examination by the physician, undergo a standardized clinical neurological examination at screening, 0, 6, 15 and 30 months. The neurological tests are performed in order to detect possible mild signs of neuromuscular disease such as disturbance of strength, balance, and coordination.

The neurological examination includes:

Extremity reflexes

Romberg (balance and coordination)

Walk on a line, 2 meters (balance and coordination)

Standing on 1 leg, left and right, 15 seconds per leg (balance and coordination)

Finger-nose (coordination)

Mimic (cranial nerves)

Babinski reflex (central function)

Muscle strength (shake hands) biceps, triceps, distal extensors, and flexors

These examinations may also be repeated between scheduled visits at the discretion of the investigator. Screening for neurological disease with electroencephalogram (EEG) is not included due to low sensitivity and specificity. However, if any signs of neurological dysfunction are detected, the patient should be referred to a neurologist for further evaluation.

6.7 Concomitant Medication

Any concomitant medication used during the study, whether considered relevant for the study or not by the investigator must be reported on the concomitant medication log of the CRF. Please also see section 8.5, below.

7. Scheduling of Procedures

TABLE 1

| Pilot DIAGNODE-1 Study, Schedule of Study Events, T1D patients | | | | | | | |
|---|---|---|---|---|---|---|---|
| | Study Period | | | | | | |
| | Screening | Intervention | | | | Follow-up | |
| | | Visit number | | | | | |
| | 1 | 2 | 3 | 4 | 5 | 6 | 7 |
| | | | | Time (Day/Week/Month) | | | |
| | D −10 to −21 | D 1 Baseline | D 30 ± 3 | D 60 ± 3 | M 6 (D 180 ± 14) | M 15 (D 450 ± 14) | M 30 (D 900 ± 30) |
| Informed Consent | X | | | | | | |
| GAD-alum (Diamyd) treatment | | X | X | X | | | |
| Medical History | X | | | | | | |
| Physical Examination | X | X | X | X | X | X | X |
| Neurological Assessment | X | X | X | X | X | X | X |
| Concomitant Medication | X | X | X | X | X | X | X |

TABLE 1-continued

Pilot DIAGNODE-1 Study, Schedule of Study Events, T1D patients

| | Study Period | | | | | | |
|---|---|---|---|---|---|---|---|
| | Screening | Intervention | | | | Follow-up | |
| | | Visit number | | | | | |
| | 1 | 2 | 3 | 4 | 5 | 6 | 7 |
| | | | | Time (Day/Week/Month) | | | |
| | D −10 to −21 | D 1 Baseline | D 30 ± 3 | D 60 ± 3 | M 6 (D 180 ± 14) | M 15 (D 450 ± 14) | M 30 (D 900 ± 30) |
| Height | X | | | | | | |
| Weight, BMI | X | X | X | X | X | X | X |
| Urine pregnancy test (females) | | X | X | X | | | |
| Injection site inspection [a] | | X | X | X | | | |
| Insulin dose | X | X | X | X | X | X | X |
| Self Reported Hypoglycemia [b] | | X | X | X | X | X | X |
| Adverse Events | | X | X | X | X | X | X |
| Blood sampling for safety: | | | | | | | |
| * Hematology | X | X | X | X | X | X | X |
| * Chemistry | X | X | X | X | X | X | X |
| Auto-antibodies: | | | | | | | |
| * GADA | X | X | X | X | X | X | X |
| * diabetes-related autoantibodies | X | X | X | X | X | X | X |
| Blood sampling for Diabetes status: | | | | | | | |
| * HbA1c | X | X | X | X | X | X | X |
| * Fasting glucose/C-peptide | X | X | X | X | X | X | X |
| * MMTT glucose/C-peptide | | X | | | X | X | X |
| Blood sampling for, genetics, immunology | | X | X | X | X | X | X |
| Vitamin D in serum | X | | | | | | |
| Blood sampling for biobank | X | X | X | X | X | X | X |

[a] Inspection of injection site before and 60 minutes after injection by investigator or nurse
[b] Hypoglycemia defined as needing help from others and/or seizures and/or unconscious

7.1 Visits

The first visit, the screening visit (Visit 1) should be performed 10 to 21 days before planned Visit 2 (Baseline). Visit 3 and 4 should then be scheduled with a visit window of ±3 days (second and third administration of GAD-Alum) and of ±14 days for Visit 5, 6 and ±30 days for Visit 7. Please note that all visits must be calculated from the baseline visit (Visit 2) according to the visit schedule. Please also note that the visits must be performed within the visit windows to comply with the study protocol.

Please see table 1 and 2 above, for schedule of patient visits, visit windows and study drug administration.

8. Study Medication

8.1 Study medication

The following medication supplies will be used in the study:

Study medication: GAD-Alum (Diamyd®), 4 µg×3 (given three times with one month interval)

IMP supplier: Diamyd Medical AB, Stockholm, Sweden.

8.2 Supply

GAD-alum (Diamyd®) a formulation, supplied by Diamyd Medical. It will be supplied as pre-packed medication from Diamyd Medical to local pharmacy. All dosing will take place in the hospital, and handled only by trained and authorised study personnel. The study medication will be labelled with information according to local regulation. GAD-alum will be stored in a refrigerator at 2-8° C. in a secure area (e.g. a locked cabinet or drug storage room), protected from unintended use. All study medication will be labelled with information according to local regulations.

8.3 Dosage and Administration

GAD-Alum: 4 µg given into lymph node in the inguinal area (by help of ultra sound technique) three times with one month interval

8.4 Duration of Treatment

See 8.3

8.5 Concomitant Medication

No systemic immune modulating medication, and no other diabetes medication other than insulin, whether marketed or not, are allowed.

9. Response Variables and Outcomes

9.1 Exploratory assessment of efficacy

9.1.1. Efficacy Variables

As this is a pilot phase I study there is no primary efficacy endpoint, but we will still follow Change in C peptide fasting and C peptide (90 minute value and AUCmean 0-120 min) during an MMTT from baseline to month 6, 15 resp to month 30.

Th2-deviation of cell-mediated immune response seen e.g. as increased ratio of IL-5, 10, 13 in comparison with IFN gamma, TNF α, IL-1β, IL-17, and increase of T-regulatory cells. Change between baseline and subsequent visits.

Inflammatory markers e.g. TNF α, IL-1β, IL-2, IL-17. Change between baseline and subsequent visits.

Hemoglobin A1c (HbA1c), change between baseline and subsequent visits

Exogenous insulin dose per kg body weight and 24 hours, change between baseline and subsequent visits

10. Statistical Methodology and Data Management

10.1 Study design

The DIAGNODE-1 study is an open-label pilot phase I intervention study

Study Participants: Newly diagnosed classic type 1 diabetes patients: N=5. Age 18-29.99 years.

Recruited from one Endocrinology clinic in Sweden 10.2 Estimation of sample size Power analysis: No formal power analyses are done for this pilot study.

10.3 Statistical Analysis Plan

In brief the following analyses are planned:

All continuous variables will have the following descriptive statistics displayed: number of observations (n), mean value, standard deviation, minimum, median, and maximum. All variables of a categorical nature will be displayed with frequencies and percentages. The tabulation of the descriptive statistics will be split by visit. Where appropriate, baseline (screening) descriptive statistics will also be included.

Demographic and Other Baseline Characteristics

Demographics and baseline characteristics will be presented using descriptive statistics (summary tables).

Safety Variables and Efficacy Data

The AE/SAE data will be presented using a standardized tabulation of the frequency and incidence rate of all observed AEs/SAEs. The frequencies and incidence rates are calculated on a per patient basis. Adverse events will be summarized by body system, causality, and severity. Other safety data will be presented by descriptive statistics.

Efficacy data regarding C peptide and immune system as well as Adverse events and other safety data will be summarized descriptively.

After 6 months analysis of the safety data. (The results will be used for design of a phase II DIAGNODE trial).

10.4 Study Populations

Intention-to-treat population

Patients will be included in the primary intention-to-treat population for analysis of efficacy if they receive at least 1 dose of all study drugs in that arm, and are assessed at a later visit.

Per Protocol Population

In order to qualify for the stringent per protocol population, the subjects must have followed the study protocol without any major violations. Any examinations missed will be substituted with the last observation carried forward, but examinations from not more than 1 visit may be lost.

Total Population

Any patient who withdraws after having received at least one treatment (visit 2) will be included in the safety analysis (adverse events and safety parameters). Data for all patients will be listed, and a list of withdrawn patients, with all reasons for withdrawal, will be given.

10.5 Data Collection/Case Report Forms

Case report forms (CRFs) will be supplied for recording data from each patient. Since it is important to have proper data collection in a timely manner, the investigator or assigned designee shall complete the CRFs promptly. When the monitor requests additional data or clarification of data for the CRF, the request must be answered satisfactorily in due time.

It is the responsibility of the investigator to ensure that these case report forms are properly completed. The investigator will sign the designated signature pages to confirm that the case report form is accurate and complete.

To ensure legibility the CRFs should be completed in block capitals with a black or blue ballpoint pen (not pencil, felt-tip or fountain pen). Any corrections to the CRFs must be carried out by the investigator or his designate. A single stroke must be drawn through the original entry. The correction has to be dated and initialled. Incorrect entries must not be covered with correcting fluid, or obliterated, or made illegible in any way. Even if there are no changes from a previous examination, in the interests of completeness of data acquisition the questions, which are repeated in each section of the CRFs should be answered in full. A reasonable explanation must be given by the investigator for all missing data.

10.6 Data Management

Data will be coded and entered into a computer database. The handling of data, including data quality control, will comply with regulatory guidelines (e.g., International Conference on Harmonization [ICH] and Good Clinical Practice [GCP]).

11. Regulatory and Administrative Procedures

Any regulatory requirements must have been met before starting the study. The sponsor will apply for the regulatory approval to the appropriate authorities. Study sites, facilities, laboratories and all data (including source data) and documentation must be made available for inspection by the authorities.

11.2 Patient Information/Informed Consent

The investigator is responsible for giving the patients full and adequate verbal and written information about the nature, purpose, possible risk and benefit of the study. Patients must also be notified that they are free to withdraw from the study at any time. The patients should have reasonable time to read and understand the information before signing. The investigator is responsible for obtaining signed informed consent from all patients before including the patient in any study related procedures. A copy of the patient information and of the informed consent form will be given to the patients.

11.4 Patient Treatment Plan

All patients will continue to receive standard care for type 1 diabetes during the study. After the individual completion of the study, the patient will return to the standard treatment received prior to study participation.

12 Results 12.1 Summary of Results in Comparison to Prior Art Therapies

Therapeutic effect of immunotherapy using GAD is primarily evaluated based on the change in three parameters: insulin production, long-term blood sugar level (glycated haemoglobin, HbA1c) and external insulin requirement, from baseline to the end of study. Insulin production is measured as fasting C peptide, stimulated C peptide maximum, and C peptide Area Under the Curve (AUC) mean over 120 minutes during a Mixed Meal Tolerance Test (MMTT).

The below comparison of the results of the Phase 2 trial reported in Ludvigsson et al., N Engl J Med, 359, 18, pp. 1909-1920 (below referred to as "Phase 2") with the results of the trial according to the present Example show that the therapeutic effect achieved by the present invention is significantly improved.

TABLE 1

| Baseline values (standard deviation) | | | |
| --- | --- | --- | --- |
| | Diagnode | Phase 2 | Phase 2 placebo |
| C peptide AUC nmol/l/2 h | 1.11 (0.39) | 1.24 (0.57) | 1.43 (0.88) |
| Fasting C peptide nmol/l | 0.26 (0.12) | 0.33 (0.19) | 0.35 (0.23) |

TABLE 1-continued

| Baseline values (standard deviation) | | | |
|---|---|---|---|
| | Diagnode | Phase 2 | Phase 2 placebo |
| HbA1c-% | 6.73 (1.87) | 6.32 (1.27) | 6.24 (0.95) |
| Insulin dose - U/kg body weight/24 h | 0.36 (0.13) | 0.67 (0.30) | 0.66 (0.29) |

As the present example is an open label pilot study there is no placebo arm with which to directly compare clinical results in order to obtain efficacy endpoint values. The results should instead be compared to historic clinical data from other trials. In order to compare the effect size of this example with the effect size shown in the Phase 2 study, the same analysis has been performed also comparing data from the treated patients of DIAGNODE-1 with the placebo arm of the Phase 2. This repeated analysis of the phase 2 active arm generated the same results as reported in Ludvigsson et al., N Engl J Med, 359, 18, pp. 1909-1920.

TABLE 2

| Treatment effect | | | | |
|---|---|---|---|---|
| | Intralymphatic (present example) | | Subcutaneous (Phase 2) | |
| | Treatment effect, change from baseline | P-value ANCOVA | Treatment effect, change from baseline | P-value ANCOVA |
| C peptide AUC nmol/l/2 h | 0.40 (0.08; 0.71) | 0.015 | 0.30 (0.07; 0.54) | 0.012 |
| Fasting C peptide nmol/l | 0.09 (−0.01; 0.19) | 0.077 | 0.04 (−0.04; 0.12) | 0.28 |
| HbA1c-% | −1.5 (−2.2; −0.7) | 0.00022 | −0.2 (−0.7; 0.4) | 0.57 |
| Insulin dose - U/kg body weight/24 h | −0.37 (−0.56; −0.18) | 0.00026 | −0.08 (−0.19; 0.04) | 0.19 |

Treatment effect was estimated using the least square means method with baseline value as a covariate. Values in parentheses are the upper and lower 95% confidence limits. ANCOVA denotes analysis of covariance.

Intralymphatic treatment with GAD shows significantly higher levels of stimulated C peptide at 15 months as well as significantly lower insulin use and HbA1c compared to the placebo arm of the phase 2 study, whereas the subcutaneously treated arm in the phase 2 trial showed significance for only higher stimulated C peptide levels at 15 months. There was also a trend for higher fasting C peptide levels at 15 months for the intralymphatic group compared to placebo. The estimated effect size for the intralymphatic treatment compared with subcutaneous was larger for all variables.

When looking at change from baseline within the three groups Intralymphatic, Phase 2 active and Phase 2 placebo (Table 3 below), both the active and placebo treated arm of the Phase 2 trial show a significant change at 15 months compared to baseline for all variables except for HbA1C. Endogenous insulin production, both fasting and stimulated, has significantly (p<0.001) decreased and the study participants use significantly more external insulin (p<0.001) at 15 months than at baseline and have higher levels of HbA1C. For the intralymphatic group, endogenous insulin production measured as stimulated C peptide has decreased (p<0.05) at 15 months but less than for the phase 2 active and placebo group respectively. No significant change is seen regarding fasting C peptide. Notably, there is a significant decrease (p<0.05) in HbA1C over 15 months without any change in use of external insulin.

TABLE 3

| Change from baseline within groups | | | |
|---|---|---|---|
| | This Example | Phase 2 | Phase 2 placebo |
| C peptide AUC nmol/l/2 h | −0.22 ± 0.25* | −0.38 ± 0.46*** | −0.75 ± 0.61*** |
| Fasting C peptide nmol/l | −0.03 ± 0.11 | −0.12 ± 0.18*** | −0.17 ± 0.20*** |
| HbA1c-% | −1.4 ± 1.9* | 0.3 ± 1.3 | 0.5 ± 1.5 |
| Insulin dose - U/kg body weight/24 h | −0.01 ± 0.22 | 0.15 ± 0.22*** | 0.22 ± 0.29*** |

Change from baseline ± standard deviation. Change in absolute values over 15 months was evaluated using a paired t-test with significance levels denoted as *,  and * where
*p < 0.05;
** P < 0.01;
***p < 0.001

Consequently, when compared to the same placebo group and adjusting for baseline values, intralymphatic treatment with GAD shows substantially better effects on preserving stimulated and fasting C peptide as well as lowering HbA1c and use of external insulin than subcutaneous treatment with GAD.

Notably, a clinically relevant effect is seen with intralymphatic treatment on HbA1C at 15 months without any change in insulin dose. This indicates that the better preserved endogenous insulin production in the intralymphatic group is translated into better blood glucose control, an effect not observed in the subcutaneously treated group.

12.2 Conclusion 15-month results from the trial show a positive and clinically relevant effect on the three prioritized efficacy endpoints—insulin production, long-term blood sugar level (HbA1c) and external insulin requirement. No serious adverse events were reported in the trial, and safety was considered very good and comparable to trials where Diamyd® has been administered under the skin.

After three injections directly into the lymph node with the diabetes vaccine Diamyd® combined with oral vitamin D, the patients' average ability to produce insulin, the single most important efficacy endpoint, decreased by 19% over a 15 month period compared to an expected decrease of between 35% and 50% based on untreated type 1 diabetes patients in the same age group from other trials. Compared with untreated patients, the estimated relative effect of the treatment on preserving the patients' own ability to produce insulin at 15 months is 46-62%. Of the trial's total of twelve patients, three have increased their own insulin production over the 15 months they were followed.

The trial participants' long-term blood glucose levels measured as glycated hemoglobin A (HbA1c) improved over the 15 month period. HbA1c decreased by 18% compared with an expected average increase of 15%. Daily insulin doses increased during the 15-month follow-up period, on average by only 6% compared with an expected increased insulin requirement of 50%. Overall, the clinical course is positive and is observed in all ages and for both genders.

No serious adverse events were observed during the 15 months that trial participants were followed and the treatment was well tolerated by all twelve patients in the trial. The most common adverse reaction was a minor local irritation at the injection site, an adverse reaction observed to the same extent as compared to the trials conducted in more than 1,000 patients where Diamyd® was administered under the skin. Overall, the safety of administering directly into the lymph node is very good and comparable to administering under the skin.

Example 3

The therapy regime of this example has an "orthogonal" action and mitigates T1D autoimmunity in the long term. The immune system is downregulated by etanercept, which in turn downregulates the inflammation around the β cells, at the same time as a β cell autoantigen (GAD) is presented by dendritic cells, whose tolerance inducing capability has been enhanced by treatment with vitamin D.

Study: Open Label trial to evaluate the tolerability of a combination therapy consisting of GAD-alum (Diamyd®), etanercept and vitamin D in children and adolescents newly diagnosed with type 1 diabetes Active ingredients: Recombinant human glutamic acid decarboxylase (rhGAD65), calciferol (vitamin D), etanercept.

Phase of Development: Phase IIa

Objectives:

Evaluate the tolerability of a combination therapy with rhGAD65, vitamin D and etanercept Evaluate how the above mentioned treatments influence the immune system and endogenous insulin secretion Study Design:

The study is a multicenter, open-label, pilot clinical trial. All patients will from day 1 receive 2 000 IU vitamin D per os per day during 15 months, and from days 1-90 receive etanercept (Enbrel) injected subcutaneously 0.8 mg/kg body weight (max 50 mg) once a week, and receive 2 subcutaneous injections of 20 μg Diamyd® in a prime-and-boost regimen on days 30 and 60. The patients will be evaluated for tolerability for 6 months (main study period, 6 visits) and followed for additionally 24 months (extension study period, 3 visits). The total study period is 30 months.

Selection of subjects: Patients must be age 8.00 to 17.99 years old, and diagnosed with type 1 diabetes (T1D) within the previous 100 days at the time of screening. Patients will be eligible for enrolment if fasting C peptide is ≥0.12 nmol/L (0.36 ng/mL) and elevated levels of GAD65 antibodies are present.

Number of subjects planned: Approximately 20 patients will be enrolled.

Description of Treatment Groups:

There is one single treatment group. The patients will be assessed for eligibility at the screening visit (visit 1) 2 to 4 weeks prior to the start of the treatment. On visit 2 (day 1), patients eligible for the study will start the treatment as mentioned above.

Endpoints

Primary Endpoints:

To Evaluate the tolerability of a combination therapy with Diamyd®, vitamin D and etanercept at month 6 (main study period), 9, 15 and 30 (extension study period)

Variables to Evaluate Tolerability:

Reactions at the injection site

Infections

Occurrence of adverse events (AEs)

Occurrence of serious adverse events

Physiological and neurology assessments

Laboratory measurements (biochemistry and haematology), including calcium and vitamin D in serum GAD65AB titer (GADA)

Secondary Endpoints:

To evaluate how the above mentioned treatments influence the immune system and endogenous insulin secretion at month 6 (main study period), 9, 15 and 30 (extension study period)

Variables to Evaluate the Influence on the Immune System:

Inflammatory markers, especially TNF α, IL-1 β, IL-2, IL-17

Th2-deviation of cell-mediated immune response seen e.g. as increased ratio of IL-5, 10, 13 in comparison with IFN gamma, TNF α, IL-1β and IL-17

Increase of T-regulatory cells

Variables to Evaluate the Effect of Endogenous Insulin Secretion:

C peptide (90 minute value and AUCmean 0-120 min) during an MMTT

Proportion of patients with a stimulated maximum C peptide level above 0.2 nmol/L Fasting C peptide Hemoglobin A1c (HbA1c)

Exogenous insulin dose per kg body weight and 24 hours

Sample Size:

No real sample size calculation is done as this is an open-label pilot study just to see if the treatment is tolerable and does not cause negative effects on β cell function and/or immune system.

All variables will be summarized descriptively

Example 4

Title of Study: Effect of GABA or Combination GABA/GAD on the Progression of Type1 Diabetes Mellitus in Children Phase of Development: Pilot study in humans Objectives:

Evaluate the safety and influence of treatment with GABA on preservation of residual insulin secretion in recent-onset type 1 diabetes.

Evaluate the safety and influence of treatment with two doses of GAD-alum (Diamyd®) plus GABA on preservation of residual insulin secretion in recent-onset type 1 diabetes.

Study Design: The study is a 3-arm, randomized, double-blind, placebo-controlled, clinical trial.

Patients will receive either i) oral GABA, dosed per kg, twice daily for 12 months plus 2 subcutaneous injections of 20 μg Diamyd® in a prime-and-boost regimen over a period of 30 days ii) oral GABA, dosed per kg, twice daily for 12 months iii) placebo.

The patients will be followed for a total of 12 months.

Selection of Subjects: Patients must be age 4 to 17 years old, and diagnosed with type 1 diabetes (T1D) within the previous 4 weeks of randomization. Patients will be eligible for enrolment if elevated levels of GAD65 antibodies are present.

Number of subjects planned: Approximately 75 patients will be enrolled.

Description of Treatment Groups:

The patients will be assessed for eligibility prior to randomization. On visit 1 (day 1, baseline), patients eligible for the study will be randomized to 1 of 3 treatment groups:

25 patients will be assigned to receive oral GABA twice daily, dosed per kg, from day 1 through month 12. In addition 2 subcutaneous injections with 20 µg Diamyd® (GAD-alum) will be given at day 1 and month 1, i.e., 1 prime and 1 booster dose (providing a total dose of 40 µg Diamyd®).

25 patients will be assigned to receive oral GABA twice daily, dosed per kg, from day 1 through month 12. In addition 2 subcutaneous injections with placebo Diamyd® will be given at day 1 and month 1

25 patients will be assigned to receive oral placebo GABA twice daily, dosed per kg, from day 1 through month 12. In addition 2 subcutaneous injections with placebo Diamyd® will be given at day 1 and month 1

Primary Endpoint:

Evaluate the effect of GABA and GABA+GAD-alum combination on pancreatic β cell function, as measured by meal stimulated C peptide secretion levels compared to age-matched placebo controls, before and after one year of treatment.

Secondary Endpoints:

Evaluate the effect of GABA and GABA+GAD-alum combination on autoimmune diabetes autoantibodies: GAD-65, ICA512, and Zinc Transporter 8(ZnT8A) and the effect on HbA1c, fasting and stimulated glucose & glucagon levels, fasting C peptide and the amount of daily insulin usage by participants, from baseline through subsequent visits Evaluate the safety of GABA and GABA/GAD-alum combination Safety The safety assessment includes observation of reactions at the injection site, occurrence of adverse events (AEs), laboratory measurements, neurological assessments, and limited physical examinations.

Sample Size:

The sample size for the proposed study is 75 children; 50 in the treatment groups and 25 in the placebo group. For the primary comparison of the 12-month post-baseline C peptide measurements between these groups, assuming an a of 0.05 and a mean (SD) C peptide AUC of 1.0 (0.4) this sample size yields a ~40% power to detect a 25% difference and ~97% power to detect a 50% difference. Adverse events and other data will be summarized descriptively.

Example 5

Name of Active Ingredient: Recombinant Human Glutamic Acid Decarboxylase (rhGAD65)

Title of Study: A double-blind, randomized investigator-initiated study to determine the safety and the effect of Diamyd® on the progression to type 1 diabetes in children with multiple islet cell autoantibodies.

Objectives:

The primary objective is to demonstrate that Diamyd® is safe in children at risk for type 1 diabetes. The subjects will be followed for 5 years.

The secondary objective is to evaluate if Diamyd® may delay or stop the autoimmune process leading to clinical type 1 diabetes in children with ongoing persistent β-cell autoimmunity as indicated by multiple positive islet cell autoantibodies.

Study Design:

The study is a two-arm, randomized, double-blind, placebo-controlled, single center, clinical trial. The study participants will receive 2 subcutaneous injections of either Diamyd® 20 µg or placebo in a prime-and-boost regimen over a period of 30 days. The study participants will be followed for 5 years.

Post Diagnosis Intervention Protocol (PDIP)

Pending study drug shelf life, children diagnosed with clinical type 1 diabetes within the study period may be offered to continue in the trial in a post diagnosis intervention protocol (PDIP) to receive additionally 2 injections of Diamyd® regardless of which treatment group they were randomized to in the prevention part of the study.

Selection of Subjects:

Subjects must be above 4.00 years old and positive for GADA and at least one additional type 1 diabetes-associated autoantibody (IA-2Ab>5, ZnT8R/W/Q/A Ab>72 or IAA>0.8).

Number of Subjects Planned: 50 patients will be enrolled.

Description of Treatment Groups:

The patients will be assessed for eligibility at the screening visit (Visit 0) approximately 30 days prior to the first injection. On visit 1 (day 1), patients eligible for the study will be randomized to 1 of 2 treatment groups:

25 patients will be assigned to receive 2 subcutaneous injections with 20 µg Diamyd® on Days 1 and 30, i.e., 1 prime and 1 booster dose.

25 patients will be assigned to receive 2 subcutaneous injections of placebo, 1 each on days 1 and 30.

Post Diagnosis Intervention Protocol (PDIP)

Within 4 months since diabetes diagnosis, participants will receive one injection of Diamyd® 20 µg on day 1 in the post diagnosis follow-up, followed by a second injection of Diamyd® on day 30, in a prime and boost fashion (a total received dose of 40 µg Diamyd® for participants who pre-diagnosis was randomized to receive placebo and a total received dose of 80 µg Diamyd® for participants who pre-diagnosis was randomized to receive Diamyd®).

Sample Size:

Up to 50 children will be asked to participate in DIA-PREV-IT 2. It is expected that 50% of children with more than one positive islet cell autoantibody will develop type 1 diabetes within 5 years.

Analyses:

Analyses of study data will be conducted to address both safety and efficacy of the treatment.

Example 6

Title of Study: A double-blind, randomized investigator-initiated study to determine the safety and the effect of Diamyd® in combination with vitamin D on the progression to type 1 diabetes in children with multiple islet cell autoantibodies Name of active ingredient: Recombinant human glutamic acid decarboxylase (rhGAD65), calciferol (vitamin D3)

Objectives:

The primary objective is to evaluate if Diamyd®, in children treated with relatively high dose vitamin D, may delay or stop the autoimmune process leading to clinical type 1 diabetes in children with ongoing persistent β cell autoimmunity as indicated by multiple positive islet cell autoantibodies.

The secondary objective is to demonstrate that Diamyd® is safe in children at risk for type 1 diabetes.

Study Design:

The study is a two-arm, randomized, double-blind, placebo-controlled, single center, clinical trial. The study participants will receive 2 subcutaneous injections of either Diamyd® 20 µg or placebo in a prime-and-boost regimen over a period of 30 days. All study participants will be supplemented with vitamin D at a daily dose of 2000 IE during the total study period (regardless of which treatment group they are randomized to). The study participants will be followed for 5 years.

Post Diagnosis Intervention Protocol (PDIP)

Pending study drug shelf life, children diagnosed with clinical type 1 diabetes within the study period may be offered to continue in the trial in a post diagnosis intervention protocol (PDIP) to receive additionally 2 injections of Diamyd® regardless of which treatment group they were randomized to in the prevention part of the study. All children that are enrolled in the PDIP will be discontinued from the original prevention protocol to be followed thoroughly for safety and efficacy according to the PDIP or 15 months following the first injection of Diamyd® in the PDIP Selection of Subjects:

Subjects must be age 4.00 to 17.99 years old and positive GADA and at least one additional type 1 diabetes-associated autoantibody (IA-2A, ZnT8R/W/QA or IAA).

Number of Subjects Planned: Approximately 80 patients will be enrolled.

Description of Treatment Groups:

The patients will be assessed for eligibility at the screening visit (visit 0) approximately 30 days prior to the first injection. On visit 1 (day 1), patients eligible for the study will be randomized to 1 of 2 treatment groups:

Approximately 40 patients will be assigned to receive 2 subcutaneous injections with 20 µg Diamyd® on days 1 and 30, i.e., 1 prime and 1 booster dose.

Approximately 40 patients will be assigned to receive 2 subcutaneous injections of placebo, 1 each on days 1 and 30.

Both treatment groups will be supplemented with vitamin D3 at a daily dose of 2000 IE during the total study period of 5 years.

Post Diagnosis Intervention Protocol (PDIP)

Within 4 months since clinical type 1 diabetes diagnosis, participants will receive one injection of Diamyd® 20 µg on day 1 in the PDIP, followed by a second injection of Diamyd® on day 30, in a prime and boost fashion, regardless of which treatment group they were randomized to in the prevention part of the study (prior to diagnosis)

Endpoints:

Primary Endpoint:

The proportion of subjects diagnosed with clinical type 1 diabetes in the Diamyd® treated group, compared to the placebo treated group at five years after the first injection.

Secondary Endpoints:

To evaluate safety and the change in metabolic status from normal to impaired glucose metabolism in the group of children with normal glucose metabolism at baseline as well as the progression in metabolic status in the children with impaired glucose metabolism at baseline screening, in the non-diabetic children with multiple islet autoantibodies treated with Diamyd® compared to those treated with placebo.

Variables to Evaluate Safety:

Injection site reactions

Occurrence of adverse events (AEs)

Laboratory measurements (biochemistry and haematology including complete blood count (CBC)), including calcium and vitamin D3 in serum Urine analysis Physical examinations, including neurological assessments Epitope-specific GADA titer, isotypes and subtypes as well as antiidiotypic autoantibodies to GADA Metabolic Status:

Change from normal to impaired glucose metabolism, defined as any of a) F-glucose≥6.1 mmol/L b) Maximum p-glucose at 30, 60, 90 minutes≥11.1 mmol/L in the OGTT c) 120 min p-glucose≥7.8 mmol/L on OGTT d) HbA1c≥39 mmol/mol Impaired glucose metabolism has to be confirmed at a second visit. This endpoint will be used in the group of children with normal glucose metabolism at baseline screening Progression of impaired glucose metabolism from one or several of the above variables to additional signs of reduced glucose metabolism, confirmed at a second visit. This endpoint will be used in the group of children with impaired glucose metabolism at baseline.

Exploratory Endpoints:

Proportion of subjects diagnosed with clinical type 1 diabetes at 1, 2, 3 and 4 years of follow-up.

Time from baseline visit to clinical type 1 diabetes diagnosis

Change from baseline in the following key metabolic variables at various time points: HbA1c, First phase insulin response and K-value from IvGTT, AUC p-glucose and C peptide from OGTT, 120 minutes glucose and C peptide after OGTT, fasting C peptide, insulin and glucose Change in other metabolic variables from baseline: AUC C peptide, glucose and insulin from IvGTT, AUC insulin from OGTT, change in max p-glucose on OGTT.

Sample Size:

Up to 80 children will be asked to participate in DIA-PREV-IT 2. It is expected that 50% of the untreated children with multiple autoantibodies will develop type 1 diabetes within 5 years. This frequency has previously been reported equal among relatives to diabetes patients and in the general population. If 20% of the treated children will develop type 1 diabetes within the same period of time, we will have a power of 82% with α=5% with a group of 40+40=80 children. P value <0.05 will be used as significance level.

Analyses:

Analyses of study data will be conducted to address both safety and efficacy of the treatment. A statistical analytic plan (SAP) will be developed before the statistical analyses.

Analyses will be performed by using parametric statistics. If criteria of normality of variables are not met (e.g. Kolmogorov-Smirnov tests) non-parametric statistics of Wilcoxon type will be used. Four-fields tables will be analysed using the Fisher's exact test. Time to diabetes will be analysed using life-table analyses, such as Kaplan-Meier and Cox regression. Analyses of efficacy will be performed as well on per-protocol (PP) as on intention-to-treat (ITT) basis. In ITT the last observation carried forward will be applied.

Adverse events and other safety data will be summarized descriptively.

Example 7

Title of Study: A phase II, 2-Arm, Randomized, Double-Blind, Placebo-Controlled, Multicenter Study of Multiple Increasing Doses of Diamyd®, in Combination with Vitamin D, to Evaluate the Safety, Immune Response and Diabetes Status in Young Adults Newly Diagnosed with Type 1 Diabetes.

Name of Active Ingredients: Recombinant human glutamic acid decarboxylase (rhGAD65), and calciferol (vitamin D)

Objectives:

Primary Objective

To evaluate the safety of administering Diamyd® of multiple increasing doses in combination with vitamin D Secondary Objectives To evaluate the influence of the immune system of administering Diamyd® of multiple increasing doses in combination with vitamin D To compare diabetes status variables between Diamyd® and placebo before and after administering Diamyd® of multiple increasing doses in combination with vitamin D Study Design:

The study is a 2-arm, randomized, double-blind, placebo-controlled, multicenter, clinical trial. Eligible patients will receive vitamin D per os per day during 1 month prior to first Diamyd® injection. From month 1 (baseline) all patients will receive a maintenance dose of vitamin D during additionally 5 months.

Weekly subcutaneous injections of Diamyd® of increasing doses (or placebo) will be administered from month 1 (baseline) over a period of 13 weeks (dose escalation) where after the maximum dose will be administered at 2, 4 and 8 weeks interval (from week 15 through week 27) (maintenance dose). The maintenance dose will then be administered every 8-12 weeks for 1 year. The patients will be evaluated for safety and immunological parameters at month 6 and will then be evaluated for diabetes status variables at months 15 and 30. The total study period is 30 months.

Selection of subjects: Patients must be age 18 to 30 years old, and diagnosed with type 1 diabetes (T1D) within the previous 6 months at the time of screening. Patients will be eligible for enrollment if fasting C peptide is ≥0.12 nmol/L (0.36 ng/mL) and elevated levels of GAD65 antibodies are present.

Number of subjects planned: Approximately 40 patients will be enrolled.

Description of Treatment Groups:

The patients will be assessed for eligibility at the screening visit (day −14-28) 2 to 4 weeks prior to randomization. All eligible patients will from day 1 receive 7000 IU vitamin D per os per day during 1 month days to ensure vitamin D levels are above >70 nM/L prior to first Diamyd®/placebo injection. From month 1 (baseline) all patients will receive a maintenance dose of vitamin D of 2000 IU per day during additionally 5 months.

On day 1, patients eligible for the study will be randomized to 1 of 2 treatment groups:

Approximately 20 patients will be assigned to receive subcutaneous injections of Diamyd® of increasing doses, starting at baseline (month 1) as follows: 0.4; 0.8; 2; 3.2; 4; 6.4; 8; 12; 16; 20; 24, 32, 40 μg, Diamyd® weekly, where after 40 μg Diamyd® will be administered from week 15 through 27 week at 2, 4 and 8 weeks interval. 40 μg Diamyd® will thereafter be administered every 8-12 weeks for 1 year. vitamin D will be administered as described above (from day 1).

Approximately 20 patients will be assigned to receive subcutaneous injections of placebo on the same time schedule as above. vitamin D will be administered as described above (no placebo for vitamin D).

The patients will be followed for three follow-up visits at month 6, month 15, and month 30

Endpoints:

Primary Endpoint:

To evaluate the safety of administering Diamyd® of multiple increasing doses in combination with vitamin D treatment at months 6, 15 and 30.

Variables to Evaluate Safety:

Reactions of the injection site

Occurrence of adverse events (AEs)

Laboratory measurements (biochemistry and haematology)

Urinalysis (microalbuminuria, creatinine)

Physical examinations, including neurological assessments

GAD65AB titer (GADA)

Secondary Endpoints:

To evaluate the influence of the immune system and diabetes status variables between Diamyd® and placebo before and after administering Diamyd® of multiple increasing doses in combination with vitamin D treatment at month 15 and 30.

Variables to Evaluate the Influence on the Immune System:

Inflammatory marker (TNF α, IL-1 β, IL-2, IL-17)

Th2-deviation of cell-mediated immune response (seen as increased ratio of IL-5, 10, 13 in comparison with IFN gamma, TNF α, IL-1 β and IL-17)

Increase of T-regulatory cells

Variables to Evaluate the Effect of Endogenous Insulin Secretion:

Hemoglobin A1c (HbA1c), change between baseline and subsequent visits

Exogenous insulin dose per kg body weight and 24 hours, change between baseline and subsequent visits Number of self-reported episodes of hypoglycemia Fasting C peptide, change between baseline and subsequent visits C peptide AUCmean 0-120 min during MMTT, change between baseline and subsequent visits C peptide measured at 30, 60, 90, and 120 minutes during MMTT Maximum C peptide during MMTT, change between baseline and subsequent visits Proportion of patients with a stimulated maximum C peptide level above 0.2 nmol/L Sample Size:

No real sample size calculation is done as this is a study just to see if the different treatments are safe and do not cause negative effects on β cell function and/or immune system. Adverse events and other safety data will be summarized descriptively. Immunological parameters and diabetes status variables will be summarized descriptively.

The invention claimed is:

1. A method for treatment of type 1 diabetes comprising administering to a subject having a serum vitamin-D level above 50 nanomole/liter a therapeutic composition comprising glutamic acid decarboxylase (GAD) formulated in alum by injection directly into a lymph node of the subject.

2. The method according to claim 1, wherein GAD is administered in an amount of 1-15 µg, 2-10 µg, 2-5 µg, or 4 µg per injection.

3. The method according to claim 1 comprising administering the composition comprising glutamic acid decarboxylase two or more times, each administration being 14 or more days after the administering step before it.

4. The method according to claim 1 comprising administering the composition comprising glutamic acid decarboxylase two or more times, each administration being 30 or more days after the administering step before it.

5. The method according to claim 1 comprising administering the composition comprising glutamic acid decarboxylase three or more times.

6. The method according to claim 1 further comprising administering a cyclooxygenase inhibitor to the subject.

7. The method according to claim 6 wherein the cyclooxygenase inhibitor is selected from the group consisting of Ibuprofen, Dexibuprofen, Naproxen, Fenoprofen, Ketoprofen, Dexketoprofen, Flurbiprofen, Oxaprozin, Loxoprofen, Indomethacin, Tolmetin, Sulindac, Etodolac, Ketorolac, Diclofenac, Aceclofenac, Nabumetone, acetylsalicylic acid, Diflunisal (Dolobid), Salicylic acid, Salsalate (Disalcid), Piroxicam, Meloxicam, Tenoxicam, Droxicam, Lornoxicam, Isoxicam, Mefenamic acid, Meclofenamic acid, Flufenamic acid, Tolfenamic acid, Celecoxib, Rofecoxib, Valdecoxib, Parecoxib, Lumiracoxib, Etoricoxib, and Nimesulide.

8. The method according to claim 1 comprising administering abatacept to the subject.

9. The method according to claim 1 comprising administering a TNF-alpha inhibitor to the subject.

10. The method according to claim 9 wherein the TNF-alpha inhibitor is selected from the group consisting of Adalimumab, Certolizumab, Etanercept, Golimumab and Infliximab.

11. The method according to claim 1 further comprising administering an agent, wherein the agent is selected from the group consisting of vitamin-D or an analog thereof, a tyrosine kinase inhibitor, gamma-amino butyric acid or an analog thereof, and UVB-radiation.

12. The method according to claim 11, wherein the administering of an agent is performed between 7 to 90 days before the administering of the therapeutic composition step.

13. The method according to claim 11, wherein the agent comprises vitamin D or an analog thereof, the administering step is repeated for three to 48 months, and the agent is dosed so that the subject receives 7000-70000 international units (IU) per week or an equivalent amount of the analog.

14. The method according to claim 1, wherein the glutamic acid decarboxylase (GAD) is GAD-65.

15. The method according to claim 1 for increasing or preserving endogenous insulin production, or mitigating decrease of endogenous insulin production.

16. The method according to claim 1 for lowering long term blood glucose levels, as measured by HbA1c.

17. The method according to claim 1 for lowering requirements for external insulin.

* * * * *